(12) United States Patent
Rabinowitz et al.

(10) Patent No.: US 10,522,242 B2
(45) Date of Patent: Dec. 31, 2019

(54) METHODS FOR NON-INVASIVE PRENATAL PLOIDY CALLING

(71) Applicant: Natera, Inc., San Carlos, CA (US)

(72) Inventors: Matthew Rabinowitz, San Francisco, CA (US); Allison Ryan, Redwood City, CA (US); George Gemelos, Portland, OR (US); Milena Banjevic, Los Altos Hills, CA (US); Zachary Demko, San Francisco, CA (US)

(73) Assignee: Natera, Inc., San Carlos, CA (US)

( * ) Notice: Subject to any disclaimer, the term of this patent is extended or adjusted under 35 U.S.C. 154(b) by 420 days.

(21) Appl. No.: 15/343,003

(22) Filed: Nov. 3, 2016

(65) Prior Publication Data

US 2017/0076038 A1    Mar. 16, 2017

Related U.S. Application Data

(63) Continuation of application No. 14/983,128, filed on Dec. 29, 2015, now Pat. No. 10,061,889, which is a continuation of application No. 14/080,656, filed on Nov. 14, 2013, now Pat. No. 9,228,234, which is a continuation of application No. 13/896,293, filed on May 16, 2013, now abandoned, which is a continuation of application No. 13/499,086, filed as application No. PCT/US2010/050824 on Sep. 30, 2010, now abandoned.

(60) Provisional application No. 61/395,850, filed on May 18, 2010, provisional application No. 61/337,931, filed on Feb. 12, 2010, provisional application No. 61/277,876, filed on Sep. 30, 2009.

(51) Int. Cl.
| | |
|---|---|
| *G01N 33/50* | (2006.01) |
| *G16B 30/00* | (2019.01) |
| *G16B 20/00* | (2019.01) |
| *C12Q 1/6827* | (2018.01) |
| *C12Q 1/6874* | (2018.01) |
| *C12Q 1/6876* | (2018.01) |
| *C12Q 1/6883* | (2018.01) |
| *G06N 7/00* | (2006.01) |

(52) U.S. Cl.
CPC .......... *G16B 30/00* (2019.02); *C12Q 1/6827* (2013.01); *C12Q 1/6874* (2013.01); *C12Q 1/6876* (2013.01); *C12Q 1/6883* (2013.01); *G06N 7/005* (2013.01); *G16B 20/00* (2019.02); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 11/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,180,349 B1 | 1/2001 | Ginzinger |
| 6,214,558 B1 | 4/2001 | Shuber et al. |
| 6,258,540 B1 | 7/2001 | Lo et al. |
| 6,300,077 B1 | 10/2001 | Shuber et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,852,487 B1 | 10/2005 | Barany et al. |
| 6,958,211 B2 | 10/2005 | Vingerhoets et al. |
| 6,964,847 B1 | 11/2005 | Englert |

(Continued)

FOREIGN PATENT DOCUMENTS

| | | |
|---|---|---|
| CN | 1650032 A | 8/2005 |
| CN | 1674028 A | 9/2005 |

(Continued)

OTHER PUBLICATIONS

Bianchi, Circulating Fetal DNA: Its Origin and Diagnostic Potential—A Review; Placenta, 2004, 25, Supplement A, Trophoblast Research, vol. 18, S93-S101.*

(Continued)

*Primary Examiner* — Jason M Sims

(57) ABSTRACT

Disclosed herein are methods for determining the copy number of a chromosome in a fetus in the context of non-invasive prenatal diagnosis. In an embodiment, the measured genetic data from a sample of genetic material that contains both fetal DNA and maternal DNA is analyzed, along with the genetic data from the biological parents of the fetus, and the copy number of the chromosome of interest is determined. In an embodiment, the maternal serum is measured using a single-nucleotide polymorphism (SNP) microarray, along with parental genomic data, and the determination of the chromosome copy number is used to make clinical decisions pertaining to the fetus.

26 Claims, 3 Drawing Sheets

(56) References Cited

U.S. PATENT DOCUMENTS

| | | |
|---|---|---|
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 1/2010 | Lo et al. |
| 7,700,325 B2 | 5/2010 | Cantor et al. |
| 7,718,367 B2 | 5/2010 | Lo et al. |
| 7,718,370 B2 | 6/2010 | Dhallan |
| 7,727,720 B2 | 9/2010 | Dhallan |
| 7,805,282 B2 | 11/2010 | Casey |
| 7,838,647 B2 | 11/2010 | Hahn et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,450,063 B2 | 5/2013 | Dube et al. |
| 8,467,976 B2 | 8/2013 | Lo et al. |
| 8,515,679 B2 | 9/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,323,888 B2 | 4/2016 | Rava et al. |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 | 6/2017 | Zimmermann et al. |
| 10,081,839 B2 | 9/2018 | Rabinowitz et al. |
| 10,083,273 B2 | 9/2018 | Rabinowitz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-Brechot |
| 2005/0053950 A1 | 3/2005 | Ubani et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |

(56) References Cited

U.S. PATENT DOCUMENTS

| | | |
|---|---|---|
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz et al. |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0287934 A1 | 9/2014 | Szelinger et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2017/0121716 A1 | 5/2017 | Rodi et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2016/0145682 A1 | 5/2019 | Woodward et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |

FOREIGN PATENT DOCUMENTS

| | | |
|---|---|---|
| CN | 101675169 A | 3/2010 |
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2128169 A1 | 12/2010 |
| EP | 2902500 A1 | 8/2015 |
| EP | 3285193 A1 | 2/2018 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2011/516069 A | 5/2011 |
| RU | 2290078 C1 | 12/2006 |
| WO | 179851 A1 | 10/2001 |
| WO | 200190419 A2 | 11/2001 |
| WO | 2002004672 A2 | 1/2002 |
| WO | 2002055985 A2 | 7/2002 |
| WO | 2002076377 | 10/2002 |
| WO | 2003031646 A1 | 4/2003 |
| WO | 3050532 A1 | 6/2003 |
| WO | 2003062441 A1 | 7/2003 |
| WO | 0190419 A9 | 11/2003 |
| WO | 3102595 A1 | 12/2003 |
| WO | 3106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007/117256 A1 | 10/2007 |
| WO | 2007132167 A2 | 11/2007 |

(56) References Cited

FOREIGN PATENT DOCUMENTS

| | | |
|---|---|---|
| WO | 2007/147076 A2 | 12/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008059578 A1 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/036525 A2 | 3/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | 2010/033652 A1 | 3/2010 |
| WO | 2010075459 | 7/2010 |
| WO | 2011041485 A1 | 4/2011 |
| WO | 2011/057061 A1 | 5/2011 |
| WO | 2011057094 | 5/2011 |
| WO | 2011/090556 A1 | 7/2011 |
| WO | 2011087760 | 7/2011 |
| WO | 2011146632 A1 | 11/2011 |
| WO | 2012/019200 A2 | 2/2012 |
| WO | 2012/028746 A1 | 3/2012 |
| WO | 201283250 | 6/2012 |
| WO | 2012088456 A2 | 6/2012 |
| WO | 20120071621 | 6/2012 |
| WO | 2012108920 A1 | 8/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 20130130848 | 9/2013 |
| WO | 2013/159035 A2 | 10/2013 |
| WO | 2013/181651 A1 | 12/2013 |
| WO | 2014/004726 A1 | 1/2014 |
| WO | 2014/014497 A1 | 1/2014 |
| WO | 20140018080 | 1/2014 |
| WO | 2014/035986 A1 | 3/2014 |
| WO | 2014/122288 A1 | 8/2014 |
| WO | 2014/149134 A2 | 9/2014 |
| WO | 2014/151117 A1 | 9/2014 |
| WO | 2015/100427 A1 | 7/2015 |
| WO | 2015/164432 A1 | 10/2015 |
| WO | 2016/009059 A1 | 1/2016 |
| WO | 2016/065295 A1 | 4/2016 |
| WO | 2016/138080 A1 | 9/2016 |
| WO | 2016/193490 A1 | 12/2016 |
| WO | 2017/058784 A1 | 4/2017 |
| WO | 2017/181146 A1 | 10/2017 |
| WO | 2018/083467 A1 | 5/2018 |
| WO | 2018/106798 A1 | 6/2018 |
| WO | 2018/156418 A1 | 8/2018 |
| WO | 2019/140298 A1 | 7/2019 |

OTHER PUBLICATIONS

Bianchi, British Journal of Haematology, 1999, 105, 574-583; Fetal Cells in the Maternal Circulation: Feasibility for Prenatal Diagnosis.*

Carvalho, B. et al., "Exploration, normalization, and genotype calls of high-density oligonucleotide SNP array data", Biostatistics, vol. 8, No. 2, 2007, 485-499.

Ford, E. et al., "A method for generating highly multiplexed ChIP-seq libraries", BMC Research Notes, vol. 7, No. 312, May 22, 2014, 1-5.

Wapner, R. et al., "First-Trimester Screening for Trisomies 21 and 18", The New England Journal of Medicine, vol. 349, No. 15, Oct. 9, 2003, 1405-1413.

"Random variable", In the Penguin Dictionary of Mathematics. Retrieved from http://www.credoreference.com/entry/penguinmath/random_variable, 2008, 1 page.

Casbon, J. A. et al., "A method for counting PCR template molecules with application to next-generation sequencing", Nucleic Acids Research, vol. 39, No. 12, Apr. 13, 2011, 1-8.

Craig, D. W. et al., "Identification of genetic variants using barcoded multiplexed sequencing", Nature Methods, vol. 5, Oct. 2008, 887-893.

Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.

Fu, G. K. et al., "Counting individual DNA molecules by the stochastic attachment of diverse labels", PNAS, vol. 108, No. 22, May 31, 2011, 9026-9031.

Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

Hollas, B. et al., "A stochastic approach to count RN A molecules using DNA sequencing methods", Lecture Notes in Computer Science, vol. 2812, 2003, 55-62.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Jabara, C. B. et al., "Accurate sampling and deep sequencing of the HIV-1 protease gene using a Primer ID", PNAS, vol. 108, No. 50, Dec. 13, 2011, 20166-20171.

Kinde, I. et al., "Detection and quantification of rare mutations with massively parallel sequencing", PNAS, vol. 108, No. 23, Jun. 7, 2011, 9530-9535.

Kivioja, T. et al., "Counting absolute number of molecules using unique molecular identifiers", Nature Methods, Advance Online Publication, Nov. 20, 2011, 1-5.

McCloskey, M. L. et al., "Encoding PCR Products with Batch-stamps and Barcodes", Biochem Genet., vol. 45, Oct. 23, 2007, 761-767.

Merriam-Webster, , "Medical Definition of Stimulant", http://www.merriam-webster.com/medical/stimulant, Mar. 14, 2016, 7 pages.

Miner, B. E. et al., "Molecular barcodes detect redundancy and contamination in hairpin-bisulfite PCR", Nucleic Acids Research, vol. 32, No. 17, Sep. 30, 2004, 1-4.

Munne, S. et al., "Chromosome Abnormalities in Human Embryos", Textbook of Assisted Reproductive Techniques, 2004, pp. 355-377.

Ragoussis, J. , "Genotyping Technologies for Genetic Research", Annual Review of Genomics and Human Genetics, vol. 10 (1), Sep. 1, 2009, 117-133.

Schmitt, M. W. et al., "Detection of ultra-rare mutations by next-generation sequencing", PNAS, vol. 109, No. 36, Sep. 4, 2012, 14508-14513.

Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.

Taliun, D. et al., "Efficient haplotype block recognition of very long and dense genetic sequences", BMC Bioinformatics, vol. 15 (10), 2014, 1-18.

(56) References Cited

OTHER PUBLICATIONS

U.S. Appl. No. 11/004,274 2006/0052945 U.S. Pat. No. 8,024,128, filed Dec. 3, 2004 Mar. 9, 2006 Sep. 2, 2011, System and Method for Improving Clinical Decisions by Aggregating, Validating and Analysing Genetic and Phenotypic Data.
U.S. Appl. No. 11/496,982 2007/0027636, filed Jul. 31, 2006 Feb. 1, 2007, System and method for using genetic, phentoypic and clinical data to make predictions for clinical or lifestyle decisions.
U.S. Appl. No. 11/603,406 2007/0184467 U.S. Pat. No. 8,532,930, filed Nov. 22, 2006 Aug. 9, 2007 Sep. 10, 2013, Method for Determining the Number of a Chromosome in the Genome of a Target Individual Using Genetic Data From Genetically Related Individuals.
U.S. Appl. No. 11/634,550 2007/0178501, filed Dec. 6, 2006 Aug. 2, 2007, Systems and method for integrating and validating genotypic, phenotypic and medical information into a database according to a standard ontology.
U.S. Appl. No. 12/076,348 2008/0243398 U.S. Pat. No. 8,515,679, filed Mar. 17, 2008 Oct. 2, 2008 Aug. 20, 2013, System and Method for Cleaning Noisy Genetic Data and Determining Chromosome Copy Number.
U.S. Appl. No. 13/793,133 2013/0253369 U.S. Pat. No. 9,424,392, filed Mar. 11, 2013 Sep. 26, 2013 Aug. 23, 2016, System and Method for Cleaning Noisy Genetic Data From Target Individuals Using Genetic Data From Genetically Related Individuals.
U.S. Appl. No. 13/793,186 2013/0252824 U.S. Pat. No. 8,682,592, filed Mar. 11, 2013 Sep. 26, 2013 Mar. 25, 2014, System and Method for Cleaning Noisy Genetic Data From Target Individuals Using Genetic Data From Genetically Related Individuals.
U.S. Appl. No. 13/949,212 2014/0032128, filed Jul. 23, 2013 Jan. 30, 2014, System and Method for Cleaning Noisy Genetic Data and Determining Chromosome Copy Number.
U.S. Appl. No. 14/092,457 2014/0087385 U.S. Pat. No. 9,430,611, filed Nov. 27, 2013 Mar. 27, 2014 Aug. 30, 2016, System and Method for Cleaning Noisy Genetic Data From Target Individuals Using Genetic Data From Genetically Related Individuals.
U.S. Appl. No. 14/156,433 2014/0193816, filed Jan. 14, 2014 Jul. 10, 2014, System and Method for Cleaning Noisy Genetic Data From Target Individuals Using Genetic Data From Genetically Related Individuals.
U.S. Appl. No. 14/286,895 2014/0256569, filed May 23, 2014 Sep. 11, 2014, System and Method for Cleaning Noisy Genetic Data From Target Individuals Using Genetic Data From Genetically Related Individuals.
U.S. Appl. No. 15/187,555, filed Jun. 20, 2016, System and Method for Cleaning Noisy Genetic Data From Target Individuals Using Genetic Data From Genetically Related Individuals.
U.S. Appl. No. 15/191,197, filed Jun. 23, 2016, System and Method for Cleaning Noisy Genetic Data From Target Individuals Using Genetic Data From Genetically Related Individuals.
U.S. Appl. No. 15/293,257, filed Oct. 13, 2016, System and Method for Cleaning Noisy Genetic Data From Target Individuals Using Genetic Data From Genetically Related Individuals.
U.S. Appl. No. 15/413,200, field Jan. 23, 2017, System and Method for Cleaning Noisy Genetic Data and Determining Chromosome Copy Number.
U.S. Appl. No. 15/446,778, filed Mar. 1, 2017, System and Method for Cleaning Noisy Genetic Data and Determining Chromosome Copy Number.
U.S. Appl. No. 12/918,445 2011-0033862, filed Oct. 7, 2010 Feb. 10, 2011, Methods for Cell Genotyping.
U.S. Appl. No. 12/994,260 2011/0092763, filed Dec. 20, 2010 Apr. 21, 2011, Methods for Embryo Characterization and Comparison.
U.S. Appl. No. 13/057,350 2011-0178719, filed Mar. 29, 2011 Jul. 21, 2011, Methods for Allele Calling and Ploidy Calling.
U.S. Appl. No. 13/846,111 2013/0225422, filed Mar. 18, 2013 Aug. 29, 2013, Methods for Allele Calling and Ploidy Calling.
U.S. Appl. No. 13/110,685 2011/0288780 U.S. Pat. No. 8,825,412, filed May 18, 2011 Nov. 24, 2011 Sep. 2, 2014, Methods for Non-Invasive Prenatal Ploidy Calling.
U.S. Appl. No. 13/300,235 2012/0270212, filed Nov. 18, 2011 Oct. 25, 2012, Methods for Non-Invasive Prenatal Ploidy Calling.
U.S. Appl. No. 13/335,043 2012/0122701, filed Dec. 22, 2011 May 17, 2012, Methods for Non-Invasive Prenatal Paternity Testing.
U.S. Appl. No. 13/499,086 2012-0185176, filed Mar. 29, 2012 Jul. 19, 2012, Methods for Non-Invasive Prenatal Ploidy Calling.
U.S. Appl. No. 13/683,604 2013/0123120, filed Nov. 21, 2012 May 16, 2013, Highly Multiplex PCR Methods and Compositions.
U.S. Appl. No. 13/780,022 2013/0196862, filed Feb. 28, 2013 Aug. 1, 2013, Informatics Enhanced Analysis of Fetal Samples Subject to Maternal Contamination.
U.S. Appl. No. 13/791,397 2013/0178373 U.S. Pat. No. 9,163,282, filed Mar. 8, 2013 Jul. 11, 2013 Oct. 20, 2015, Methods for Non-Invasive Prenatal Ploidy Calling.
U.S. Appl. No. 13/846,160 2013/0261004, filed Mar. 18, 2013 Oct. 3, 2013, Methods for Non-Invasive Prenatal Paternity Testing.
U.S. Appl. No. 13/896,293 2013/0274116, filed May 16, 2013 Oct. 17, 2013, Methods for Non-Invasive Prenatal Ploidy Calling.
U.S. Appl. No. 13/968,302 2014/0051585, filed Aug. 15, 2013 Feb. 20, 2014, Mehtods and Compositions for Reducing Genetic Library Contamination.
U.S. Appl. No. 14/044,434 2014/0094373, filed Oct. 2, 2013 Apr. 3, 2014, Highly Multiplex PCR Methods and Composition.
U.S. Appl. No. 14/080,656 2014/0154682 U.S. Pat. No. 9,228,234, filed Nov. 14, 2013 Jun. 5, 2014 Jan. 5, 2016, Methods for Non-Invasive Prenatal Ploidy Calling.
U.S. Appl. No. 14/100,928 2014/0100134 U.S. Pat. No. 8,949,036, filed Dec. 9, 2013 Apr. 1, 2014 Feb. 3, 2015, Methods for Non-Invasive Prenatal Ploidy Calling.
U.S. Appl. No. 14/171,587 2014/0141981, filed Feb. 3, 2014 May 22, 2014, Highly Multiplex PCR Methods and Compositions.
U.S. Appl. No. 14/179,399 2014/0162269, filed Feb. 12, 2014 Jun. 12, 2014, Methods for Non-Invasive Prenatal Ploidy Calling.
U.S. Appl. No. 14/225,356 2014/0206552, filed Mar. 25, 2014 Jul. 24, 2014, Methods for Preimplantation Genetic Dianosis by Sequencing.
U.S. Appl. No. 14/446,232 2014/0336060 U.S. Pat. No. 9,334,541, filed Jul. 29, 2014 Nov. 13, 2014 May 10, 2016, Methods for Non-Invasive Prenatal Ploidy Calling.
U.S. Appl. No. 14/532,666 2015/0051087, filed Nov. 4, 2014 Feb. 19, 2015, Methods for Non-Invasive Prenatal Ploidy Calling.
U.S. Appl. No. 14/546,321 2015/0072872, filed Nov. 18, 2014 Mar. 12, 2013, Methods for Non-Invasive Prenatal Ploidy Calling.
U.S. Appl. No. 14/866,223, filed Sep. 25, 2015, Methods for Non-Invasive Prenatal Ploidy Calling.
U.S. Appl. No. 14/877,925 2017/0051355, filed Oct. 7, 2015 Feb. 23, 2017, Highly Multiplex Pcr Methods and Compositions.
U.S. Appl. No. 14/983,128, filed Dec. 29, 2015, Methods for Non-Invasive Prenatal Ploidy Calling.
U.S. Appl. No. 15/243,915 2016-0357904, filed Aug. 21, 2016 Dec. 8, 2016, Methods for Non-Invasive Prenatal Ploidy Calling.
U.S. Appl. No. 15/252,795, filed Aug. 31, 20116, Methods for Non-Invasive Prenatal Ploidy Calling.
U.S. Appl. No. 15/273,332 2017-0011166, filed Sep. 22, 2016 Jan. 13, 2017, Methods for Non-Invasive Prenatal Ploidy Calling.
U.S. Appl. No. 15/343,003, filed Nov. 3, 2016, Methods for Non-Invasive Prenatal Ploidy Calling.
U.S. Appl. No. 15/586,013, filed May 3, 2017, Methods for Non-Invasive Prenatal Ploidy Calling.
U.S. Appl. No. 13/970,436 2014/0100126, filed Aug. 19, 2013 Apr. 10, 2014, Methods for Non-Invasive Prenatal Testing Using Parental Mosaicism Data.
U.S. Appl. No. 15/433,950, filed Feb. 15, 2017, Methods for Non-Invasive Prenatal Testing Using Prental Mosaicism Data.
U.S. Appl. No. 13/793,316 2014/0065621, filed Mar. 11, 2013 Mar. 6, 2014, Mathods for Increasing Fetal Fraction in Maternal Blood.
U.S. Appl. No. 14/498,629 2015/0147815, filed Sep. 26, 2014 May 28, 2015, Cell Free Dna Dignostic Testing Standards.
U.S. Appl. No. 14/996,097 2016/0244838, filed Jan. 14, 2016 Aug. 25, 2016, Cell Free Dna Diagnostic Testing Standards.
U.S. Appl. No. 14/732,632, filed Nov. 12, 20104, Systems and Methods for Detection of Aneuploidy.

(56) References Cited

OTHER PUBLICATIONS

U.S. Appl. No. 14/538,998, filed Nov. 24, 2014, Methods for Simultaneous Amplification of Target Loci.
U.S. Appl. No. 14/538,982 2015/0322507, filed Nov. 24, 2014 Nov. 12, 2015, Methods for Simultaneous Amplification of Target Loci.
U.S. Appl. No. 14/692,703, filed Apr. 21, 2015, Detecting Mutations and Ploidy in Chromosomal Segments.
U.S. Appl. No. 14/882,763, filed Oct. 14, 2015, Detecting Cancer Mutations and Aneuploidy in Chromosomal Segments.
U.S. Appl. No. 14/918,544, filed Oct. 20, 2015, Methods for Simultaneous Amplification of Target Loci.
U.S. Appl. No. 15/336,630, filed Oct. 27, 2016, Methods for Simultaneous Amplification of Target Loci.
U.S. Appl. No. 15/186,774, filed Jun. 20, 2016, Systems and Methods for Determining Aneuploidy Risk Using Sample Fetal Fraction.
U.S. Appl. No. 15/372,279, filed Dec. 7, 2016, Compositions and Methods for Identifying Nucleic Acid Molecules.
"Blast of AAAAAAAAATTTAAAAAAAAATTT(http://blast.ncbi.nlm.nih.gov/Blast.cgi, downloaded May 4, 2015)".
"CompetitivePCR Guide,", TaKaRa Biomedicals, Lit. # L0126 Rev. Aug. 1999, 9 pgs.
"Db SNP rs2056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in U.S. Appl. No. 14/04,4434".
"European Application No. 014198110, European Search Report dated Apr. 28, 2015, 3 pages."
"Finishing the Euchromatic Sequence of the Human Genome", Nature vol. 431,(Oct. 21, 2004),931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
"How Many Carbs in a Potato? [Online]", Retrieved from theInternet<http://www.newhealthguide.org/How-Many-Carbs-In-A-Potato.html>, Nov. 1, 2014, 3 pgs.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.
"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_C01.
"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"NucleicAcids, Linkers and Primers: Random Primers", New England BioLabs 1998/99Catalog, 1998, 121 and 284.
"Primer3, information sheet, Sourceforge.net. [retrieved on Nov. 12, 2012]. Retrieved from the Internet: <URL: http://primer3.sourceforge.net/>", 2009, 1 pg.
"www.fatsecret.com" (printed from internet Nov. 1, 2014).
International Application Serial No. PCT/US14/51926, International Search Report and Written Opinion dated Dec. 9, 2014, 5 pgs.
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Agarwal, Ashwin et al., "Commercial Landscape of Noninvasive Prenatal Testing in the United States", Prenatal Diagnosis,33, 2013, 521-531.
Alkan, Can et al., "Personalized Copy Number and Segmental Duplication Maps Using Next-Generation Sequencing", Nature Genetics, 41, 10, 2009, 1061-1068.
Allaire, F. R., "Mate selection by selection index theory", Theoretical Applied Genetics, 57(6), 1980, 267-272.
Allawi, Hatim T. et al., "Thermodynamics of internal C•T Mismatches in DNA", Nucleic Acids Research, 26 (11), 1998, 2694-2701.
Aoki, Yasuhiro, "Statistical and Probabilistic Bases of Forensic DNA Testing", The Journal of the Iwate Medical Association, 2002, vol. 54, p. 81-94.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Bada, Michael A. et al., "Computational Modeling of Structural Experimental Data", Methods in Enzymology,317, 2000, 470-491.
Beaumont, Mark A et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 1533.
Benn, P. et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/5greatpregnancyfoods/, Apr. 15, 2008).
Bianchi, D. W. et al., "Fetal gender and aneuploidy detection using fetal cells maternal blood: analysis of NIFTY I data", Prenat Diagn 2002; 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O., "The Unified Medical Language System (UMLS): Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.

(56) References Cited

OTHER PUBLICATIONS

Cairns, Paul et al., "Homozygous Deletions of 9p21 in Primary Human Bladder Tumors Detected by Comparative Multiplex Polymerase Chain Reaction", Cancer Research, 54, 1994, 1422-1424.

Caliendo, Angela, "Multiplex PCR and Emerging Technologies for the Detection of Respiratory Pathogens", Clinical Infectious Diseases, 52(4), 2011, S326-S330.

Carnevale, Alessandra et al., "Attitudes of Mexican Geneticists Towards Prenatal Diagnosis and Selective Abortion", American Journal of Medical Genetics, 75, 1998, 426-431.

Chakraborty, R. et al., "Paternity Exclusion by DNA Markers: Effects of Paternal Mutations", Journal of Forensic Sciences, vol. 41, No. 4, Jul. 1996, 671-677.

Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.

Chetty, Shilpa et al., "Uptake of Noninvasive Prenatal Testing (NIPT) in Women Following Positive Aneuploidy Screening", Prenatal Diagnosis,33, 2013, 542-546.

Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.

Chiu, Rossa W. et al., "Effects of Blood-Processing Protocols on Fetal and Total DNA Quantification in Maternal Plasma", Clinical Chemistry, 47(9), 2001, 1607-1613.

Chiu, Rossa W.K et al., "Maternal Plasma DNA Analysis with Massively Parallel Sequencing by Litigation for Noninvasive Prenatal Diagnosis of Trisomy 21", Clinical Chemistry, 56, 3, 2010, 459-463.

Chiu, Rossa W.K et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.

Chiu, Rossa W.K. et al., "Non-Invasive Prenatal Diagnosis by Single Molecule Counting Technologies", Trends in Genetics, 25 (7), 2009, 324-331.

Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.

Chu, Tianjiao. et al., "A Novel Approach Toward the Challenge of Accurately Quantifying Fetal DNA in Maternal Plasma", Prenatal Diagnosis,30, 2010, 1226-1229.

Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.

Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.

Cossu, Gianfranco et al., "Rh D/d Genotyping by Quantitative Polymerase Chain Reaction and Capillary Zone Electrophoresis", Electrophoresis, 17, 1996, 1911-1915.

Coyle, J. F. et al., "Standards for detailed clinical models as the basis for medical data exchange and decision support", International Journal of Medical Informatics, 69(2-3), 2003, 157-174.

Cross, Jillian et al., "Resolution of trisomic mosaicism in prenatal diagnosis: estimated performance of a 50K SNP microarray", Prenat Diagn 2007; 27, 2007, 1197-1204.

D'Aquila, Richard et al., "Maximizing sensitivity and specificity of PCR by pre-amplification heating", Nucleic Acids Research, 19(13), 1991, p. 3749.

Daruwala, Raoul-Sam et al., "A Versatile Statistical Analysis Algorithm to Detect Genome Copy Number Variation", PNAS, 101(46), 2004, 16292-16297.

De Vries, et al., "Diagnostic genome profiling in mental retardation", Am J Hum Genet, 77, published online Aug. 30, 2005, 2005, 606-616.

Deangelis, M. et al., "Solid-phase Reversible Immobilization for the Isolation of PCR Products", Nucleic Acids Research, 23 (22), 1995, 4742-4743.

Devaney, S. et al., "Noninvasive Fetal Sex Determination Using Cell-Free Fetal DNA: A Systematic Review and Meta-analysis", JAMA, 306 (6), 2011, 627-636.

Dhallan, et al., "Methods to Increase the Percentage of Free Fetal DNA Recovered from the Maternal Circulation", JAMA, 291(9), 2004, 1114-1119.

Dhallan, Ravinder et al., "A non-invasive test for prenatal diagnosis based on fetal DNA present in maternal blood: a preliminary study", The Lancet, 369, 2007, 474-481.

Dieffenbach, C W. et al., "General concepts for PCR primer design", Genome Research. PCR methods and Applications vol. 3, 1993, S30-S37.

Ding, C et al., "Direct molecular haplotyping of long-range genomic DNA with M1-PCR", PNAS 100(13), 2003, 7449-7453.

Dohm, J. et al., "Substantial Biases in Ultra-Short Read Data Sets From High-Throughput DNA Sequencing", Nucleic Acids Research, 36 (16), e105, 2008, 10 pgs.

Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res.,11, 2001, 1473-1483.

Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.

Donoso, P. et al., "Current Value of Preimplantation Genetic Aneuploidy Screening in IVF", Human Reproduction Update, 13(1), 2007, 15-25.

Echeverri, et al., "Caffeine's Vascular Mechanisms of Action", International Journal of Vascular Medicine vol. 2010(2010), 10 pages, Aug. 25, 2010.

Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.

Eichler, H., "Mild Course of Fetal Rh D Haemolytic Disease due to Maternal Alloimmunisation to Paternal HLA Class I and II Antigens", Vox Sang, 68, 1995, 243-247.

Ellison, Aaron M., "Bayesian Inference in Ecology", Ecology Letters, 2004, vol. 7, p. 509-520.

Ellonen, P. et al., "Development of SNP Microarray for Supplementary Paternity Testing", International Congress Series,1261, 2004, 12-14.

EP06838311.6, "European Communication and Extended European Search Report", dated Dec. 30, 2008, 8 pgs.

EP08742125.1, "European Communication pursuant to Article 94(3) EPC and Examination Report", dated Feb. 12, 2010, 5 pgs.

Fan, et al., "Whole-genome molecular haplotyping of single cells", Nature Biotechnology, vol. 29, No. 1, Jan. 1, 2011, 51-57.

Fan, Christina H. et al., "Non-Invasive Prenatal Measurement of the Fetal Genome", Nature, doi:10.1038/nature11251, 2012, 26 pgs.

Fan, Christina H et al., "Noninvasive Diagnosis of Fetal Aneuploidy by Shotgun Sequencing DNA from Maternal Blood", PNAS, 105, 42, 2008, 16266-16271.

Fan, Jian-Bing et al., "Highly Parallel Genomic Assay", Nature Reviews, 7, 2006, 632-644.

Fazio, Gennaro. et al., "Identification of RAPD Markers Linked to Fusarium Crown and Root Rot Resistance (Frl) in Tomato", Euphytica 105, 1999, 205-210.

Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.

Fiorentino, F. et al., "Strategies and Clinical Outcome of 250 Cycles of Preimplantation Genetic Diagnosis for Single Gene Disorders", Human Reproduction, 21, 3, 2006, 670-684.

(56) References Cited

OTHER PUBLICATIONS

Fiorentino, Francesco et al., "Short Tandem Repeats Haplotyping of the Hla Region in Preimplantation HLA Matching", European Journal of Human Genetics, 13, 2005, 953-958.

Forejt, et al., "Segmental trisomy of mouse chromosome 17: introducing an alternative model of Down's syndrome", Genomics, 4(6), 2003, 647-652.

Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.

Fredriksson, et al., "Multiplex amplification of all coding sequences within 10 cancer genes by Gene-Collector", Nucleic Acids Research, 2007, vol. 35, No. 7 e47, 1-6.

Freeman, Jennifer L. et al., "Copy Number Variation: New Insights in Genome Diversity", Genome Research, 16, 2006, 949-961.

Frost, Mackenzie S et al., "Differential Effects of Chronic Pulsatile Versus Chronic Constant Maternal Hyperglycemia on Fetal Pancreatic B-Cells", Journal of Pregnancy, 2012 Article ID 812094, 2012, 8.

Ganshirt-Ahlert, D. et al., "Ratio of Fetal to Maternal DNA is Less Than 1 in 5000 at different Gestational Ages in Maternal Blood", Clinical Genetics,38, 1990, 38-43.

Ganshirt-Ahlert, D. et al., "Fetal DNA in Uterine Vein Blood", Obstetrics & Gynecology, 80 (4), 1992, 601-603.

Ganshirt-Ahlert, Dorothee et al., "Three Cases of 45,X/46,XYnf Mosaicism", Human Genetics, 76, 1987, 153-156.

Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.

Ghanta, Sujana. et al., "Non-Invasive Prenatal Detection of Trisomy 21 Using Tandem Single Nucleotide Polymorphisms", PLoS ONE, 5 (10), 2010, 10 pgs.

Gjertson, David W. et al., "Assessing Probability of Paternity and the Product Rule in DNA Systems", Genetica, 96, 1995, 89-98.

Greenwalt, T. et al., "The Quantification of Fetomaternal Hemorrhage by an Enzyme-Linked Antibody Test with Glutaraldehyde Fixation", Vox Sang, 63, 1992, 268-271.

Guerra, J., "Terminal Contributions for Duplex Oligonucleotide Thermodynamic Properties in the Context of Nearest Neighbor Models", Biopolymers, 95(3), (2010), 2011, 194-201.

Guetta, Esther et al., "Analysis of Fetal Blood Cells in the Maternal Circulation: Challenges, Ongoing Efforts, and Potential Solutions", Stem Cells and Development, 13, 2004, 93-99.

Guichoux, et al., "Current Trends in Microsatellite Genotyping", Molecular Ecology Resources, 11, 2011, 591-911.

Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].

Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.

Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.

Hardenbol, P., "Multiplexed Genotyping With Sequence-Tagged Molecular Inversion Probes", Nature Biotechnology, 21 (6), 2003, 673-678.

Hardenbol, Paul et al., "Highly multiplexed molecular inversion probe genotyping: Over 10,000 targeted SNPs genotyped in a singled tube assay", Genome Research, 15, 2005, 269-275.

Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.

Harper, J. C. et al., "Recent Advances and Future Developments in PGD", Prenatal Diagnosis, 19, 1999, 1193-1199.

Harton, G.L. et al., "Preimplantation Genetic Testing for Marfan Syndrome", Molecular Human Reproduction, 2 (9), 1996, 713-715.

Hayden, et al., "Multiplex-Ready PCR: A new method for multiplexed SSR and SNP genotyping", BMC Genomics 2008, 9(80), 1-12.

Hellani, A. et al., "Clinical Application of Multiple Displacement Amplification in Preimplantation Genetic Diagnosis", Reproductive BioMedicine Online, 10 (3), 2005, 376-380.

Hellani, Ali et al., "Multiple displacement amplification on single cell and possible PGD applications", Molecular Human Reproduction, 10(11), 2004, 847-852.

Hojsgaard, S. et al., "BIFROST—Block recursive models induced from relevant knowledge, observations, and statistical techniques", Computational Statistics & Data Analysis, 19(2), 1995, 155-175.

Holleley, et al., "Multiplex Manager 1.0: a Cross-Platform Computer Program that Plans and Optimizes Multiplex PCR", BioTechniques46:511-517 (Jun. 2009), 511-517.

Hollox, E. et al., "Extensive Normal Copy Number Variation of a β-Defensin Antimicrobial-Gene Cluster", Am. J. Hum. Genet., 73, 2003, 591-600.

Homer, et al., "Resolving Individuals Contributing Trace Amounts of DNA to Highly Complex Mixtures Using High-Density SNP Genotyping Microarrays", PLOS Genetics, 4(8), 2008, 9 pgs.

Hoogendoorn, Bastiaan et al., "Genotyping Single Nucleotide Polymorphisms by Primer Extension and High Performance Liquid Chromatography", Hum Genet, 104, 1999, 89-93.

Hospital, F et al., "A General Algorithm to Compute Multilocus Genotype Frequencies Under Various Mating Systems" vol. 12, No. 6, Jan. 1, 1996 (Jan. 1, 1996), pp. 455-462.

Howie, et al., "Fast and accurate genotype imputation in genome-wide association studies through pre-phasing", Nature Genetics, vol. 44, No. 8, Jul. 22, 2012, 955-959.

Hu, Dong Gui et al., "Aneuploidy Detection in Single Cells Using DNA Array-Based Comparative Genomic Hybridization", Molecular Human Reproduction, 10(4), 2004, 283-289.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina Catalog, "Paired-End Sample Preparation Guide, Illumina Catalog# PE-930-1 001, Part# 1005063 Rev. E", 2011, 1-40.

Ishii, et al., "Optimization of Annealing Temperature to Reduce Bias Caused by a Primer Mismatch in Multitemplate PCR", Applied and Environmental Microbiology, Aug. 2001, p. 3753-3755.

Johnson, D.S. et al., "Comprehensive Analysis of Karyotypic Mosaicism Between Trophectoderm and Inner Cell Mass", Molecular Human Reproduction, 16(12), 2010, 944-949.

Johnson D.S, et al., "Preclinical Validation of a Microarray Method for Full Molecular Karyotyping of Blastomeres in a 24-h Protocol", Human Reproduction, 25 (4), 2010, 1066-1075.

Kaplinski, Lauris et al., "MultiPLX: Automatic Grouping and Evaluation of PCR Primers", Bioinformatics, 21(8), 2005, 1701-1702.

Kazakov, V.I et al., "Extracellular DNA in the Blood of Pregnant Women", sitologia, 37, 3, 1995, 8.

Kijak, G. et al., "Discrepant Results in the Interpretation of HIV-1 Drug-Resistance Genotypic Data Among Widely Used Algorithms", HIV Medicine, 4, 2003, 72-78.

Kinnings, S. L. et al., "Factors affecting levels of circulating cell-free fetal DNA in maternal plasma and their implications for noninvasive prenatal testing", Prenatal Diagnosis, vol. 35, 2015, 816-822.

Konfortov, Bernard A. et al., "An Efficient Method for Multi-Locus Molecular Haplotyping", Nucleic Acids Research, 35(1), e6, 2007, 8 pgs.

Krjutskov, K et al., "Development of a single tube 640-plex genotyping method for detection of nucleic acid variations on microarrays", Nucleic Acids Research, vol. 36, No. 12, May 23, 2008 (May 23, 2008), pp. e75-e75.

(56) References Cited

OTHER PUBLICATIONS

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Lambert-Messerlian, G. et al., "Adjustment of Serum Markers in First Trimester Screening", Journal of Medical Screening, 16 (2), 2009, 102-103.
Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, Rebecca J et al., "Detection of Chromosomal Alterations in the Circulation of Cancer Patients with Whole-Genome Sequencing", Science Translational Medicine, 4, 162, 2012, 12.
Li, Yind. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Li B, "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katarina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4390-4395.
Lo, Dennis Y. et al., "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Dennis Y. et al., "Plasma placental RNA allelic ratio permits noninvasive prenatal chromosomal aneuploidy detection", Nature Medicine, 13(2), 2007, 218-223.
Lo, Dennis Y.M. et al., "Maternal Plasma DNA Sequencing Reveals the Genome-Wide Genetic and Mutational Profile of the Fetus", Science Translational Medicine, 2, 61, 2010, 13.
Lo, Dennis Y.M. et al., "Presence of Fetal DNA in Maternal Plasma and Serum", The Lancet, 350, 1997, 485-487.
Lo, Dennis Y.M. et al., "Quantitative Analysis of Fetal DNA in Maternal Plasma and Serum: Implications for Noninvasive Prenatal Diagnosis", Am. J. Hum. Genet., 62, 1998, 768-775.
Lo, Y.M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M. D. et al., "Prenatal Determination of Fetal RhD Status by Analysis of Peripheral Blood of Rhesus Negative Mothers", The Lancet, 341, 1993, 1147-1148.
Lo, Y-M.D et al., "Detection of Single-Copy Fetal DNA Sequence from Maternal Blood", The Lancet, 335, 1990, 1463-1464.
Lo, Y. et al., "Detection of Fetal RhD Sequence from Peripheral Blood of Sensitized RhD-Negative Pregnant Women", British Journal of Haematology, 87, 1994, 658-660.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Markoulatos, P. et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).
May, Rober M. et al., "How Many Species Are There on Earth?", Science, 241, 1988, 1441-1449.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetrics, 2013, 5 pgs.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Morand, et al., "Hesperidin contributes to the vascular protective effects of orange juice: a randomized crossover study in healthy volunteers", Am J Clin Nutr. Jan. 2011; 93(1 ):73-80. Epub Nov. 10, 2010.
Munne, S. et al., "Chromosome abnormalities in human embryos", Human Reproduction update, 4 (6), 842-855.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.

(56) References Cited

OTHER PUBLICATIONS

Nicolaides, K.H. et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
O'Malley, R. et al., "An adapter ligation-mediated PCR method for high-throughput mapping of T-DNA inserts in the *Arabidopsis* genome", Nat. Protoc. 2, 2910-2917 (2007).
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, Glenn et al., "DNA Sequencing of Maternal Plasma Reliably Identifies Trisomy 18 and Trisomy 13 as Well as Down Syndrome: An International Collaborative Study", Genetics in Medicine, 2012, 10.
Palomaki, Glenn E. et al., "DNA Sequencing of Maternal Plasma to Detect Down Syndrome: an International Clinical Validation Study", Genetics in Medicine (pre-print version), 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.
PCT/US2006/045281, "International Preliminary Report on Patentability", dated May 27, 2008, 1 pg.
PCT/US2006/045281, "International Search Report and Written Opinion", dated Sep. 28, 2007, 7 pgs.
PCT/US2008/003547, "International Search Report", dated Apr. 15, 2009, 5 pgs.
PCT/US2009/034506, "International Search Report", dated Jul. 8, 2009, 2 pgs.
PCT/US2009/045335, "International Search Report", dated Jul. 27, 2009, 1 pg.
PCT/US2009/052730, "International Search Report", dated Sep. 28, 2009, 1 pg.
PCT/US2010/050824, "International Search Report", dated Nov. 15, 2010, 2 pgs.
PCT/US2011/037018, "International Search Report", dated Sep. 27, 2011, 2 pgs.
PCT/US2011/061506, "International Search Report", dated Mar. 16, 2012, 1 pgs.
PCT/US2011/066938, "International Search Report", dated Jun. 20, 2012, 1 pg.
PCT/US2012066339, "International Search Report", dated Mar. 5, 2013, 1 pg.
PCT/US2013/028378, "International Search Report and Written Opinion", dated May 28, 2013, 11 pgs.
PCT/US2013/57924, "International Search Report and Written Opinion", dated Feb. 18, 2014, 8 pgs.
PCT/US2014/051926, "International Search Report", dated Dec. 9, 2014, 3 pgs.
PCT/US2014/51926, "Written Opinion", dated Dec. 9, 2014, 5 pgs.
PCT/US2015/026957, "International Preliminary Report on Patentability dated Nov. 3, 2016", Nov. 3, 2016, 3 pages.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends in Genetics, 10, 6, 1994, 204-209.
Perkel, Jeffrey M., "Overcoming the Challenges of Multiplex PCR", Biocompare Editorial Article, Null, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Porreca, Gregory J. et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005 (Jun. 16, 2005), pp. 3455-3464.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterlity, Elsevier Science Inc, 97(2), 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Renwick, Pamela et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet<http://www.youandyourfamily.com/article.php?story=Eating+by+Trimester>, 2014, 3.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.

(56) References Cited

OTHER PUBLICATIONS

Rozen, Steve et al., "Primer3 on the WWW for General Users and for Biologis Programmers", Methods in Molecular Biology, 132: Bioinformatics Methods and Protocols, 1999, 365-386.

Russell, L M., "X Chromosome Loss and Ageing", Cytogenetic and Genome Res., 116, 2007, 181-185.

Ryan, et al., "The importance of phase information for human genomics", Nature Reviews Genetics, vol. 12, No. 3, Mar. 1, 2011.

Ryan, Allison et al., "Informatics-Based, Highly Accurate, Noninvasive Prenatal Paternity Testing", Genetics in Medicine (advance online publication), 2012, 5 pgs.

Rychlik, et al., "Optimization of the annealing temperature for DNA amplification in vitro", Nucleic Acids Research, 18(21), 1990, 6409-6412.

Samango-Sprouse, C. et al., "SNP-Based Non-Invasive Prenatal Testing Detects Sex Chromosome Aneuploidies with High Accuracy", Prenatal Diagnosis, 33, 2013, 1-7.

Sander, Chris, "Genetic Medicine and the Future of Health Care", Science, 287(5460), 2000, 1977-1978.

Santalucia, J. et al., "The Thermodynamics of DNA Structural Motifs", Annu. Rev. Biophys. Biomol. Struct., 33, 2004, 415-440.

Santalucia, John J.R et al., "Improved Nearest-Neighbor Parameters for Predicting DNA Duplex Stability", Biochemistry, 35, 1996, 3555-3562.

Sasabe, Yutaka, "Genetic Diagnosis of Gametes and Embryos Resulting from Art", Japanese Journal of Fertility and Sterility, 2001, vol. 46, No. 1, p. 43-46.

Schoumans, J et al., "Detection of chromosomal imbalances in children with idiopathic mental retardation by array based comparative genomic hybridisation (array-CGH)", JMed Genet, 42, 2005, 699-705.

Sebat, Jonathan et al., "Strong Association of De Novo Copy Number Mutations with Autism", Science, 316, 2007, 445-449.

Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.

Sermon, Karen et al., "Preimplantation genetic diagnosis", The Lancet, Lancet Limited. 363(9421), 2000, 1633-1641.

Servin, B. et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.

Shaw-Smith, et al., "Microarray Based Comparative Genomic Hybridisation (array-CGH) Detects Submicroscopic Chromosomal Deletions and Duplications in Patients with Learning Disability/ Mental Retardation and Dysmorphic Features", J. Med. Genet., 41, 2004, 241-248.

Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.

Shen, Zhiyong, "MPprimer: a program for reliable multiplex PCR primer design", BMC Bioinformatics 2010, 11:143, 1-7.

Sherlock, J. et al., "Assessment of Diagnostic Quantitative Fluorescent Multiplex Polymerase Chain Reaction Assays Performed on Single Cells", Annals of Human Genetics,62, 1, 1998, 9-23.

Simpson, J. et al., "Fetal Cells in Maternal Blood: Overview and Historical Perspective", Annals New York Academy of Sciences, 731, 1994, 1-8.

Sint, Daniela et al., "Advances in Multiplex PCR: Balaning Primer Efficiencies and Improving Detection Success", Methods in Ecology and Evolution, 3, 2012, 898-905.

Slater, Howard et al., "High-Resolution Identification of Chromosomal Abnormalities Using Oligonucleotide Arrays Containing 116,204 SNPs", Am. J. Hum. Genet., 77, 5, 2005, 709-726.

Snijders, Antoine et al., "Assembly of Microarrays for Genome-Wide Measurement of DNA Copy Number", Nature Genetic, 29, 2001, 263-264.

Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.

Sparks, Andrew B. et al., "Selective Analysis of Cell-Free DNA in Maternal Blood for Evaluation of Fetal Trisomy", Prenatal Diagnosis, 32, 2012, 1-7.

Spiro, Alexander et al., "A Bead-Based Method for Multiplexed Identification and Quantitation of DNASequences Using Flow Cytometry", Applied and Environmental Microbiology, 66, 10, 2000, 4258-4265.

Spits, C. et al., "Optimization and Evaluation of Single-Cell Whole Genome Multiple Displacement Amplification", Human Mutation, 27(5), 496-503, 2006.

Srinivasan, et al., "Noninvasive Detection of Fetal Subchromosome Abnormalities via Deep Sequencing of Maternal Plasma", The American Journal of Human Genetics 92, 167-176, Feb. 7, 2013.

Stephens, Mathews. et al., "A Comparison of Bayesian Methods for Haplotype Reconstruction from Population Genotype Data", Am. J. Hum. Genet.,73, 2003, 1162-1169.

Stevens, Robert et al., "Ontology-Based Knowledge Representation for Bioinformatics", Briefings in Bioinformatics, 1, 4, 2000, 398-414.

Steyerberg, E.W. et al., "Application of Shrinkage Techniques in Logistic Regression Analysis: A Case Study", Statistica Neerlandica, 55(1), 2001, 76-88.

Strom, C. et al., "Three births after preimplantation genetic diagnosis for cystic fibrosis with sequential first and second polar body analysis", American Journal of Obstetrics and Gynecology, 178 (6), 1998, 1298-1306.

Strom, Charles M. et al., "Neonatal Outcome of Preimplantation Genetic Diagnosis by Polar Body Removal: The First 109 Infants", Pediatrics, 106( 4), 2000, 650-653.

Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.

Su, S.Y. et al., "'Inferring combined CNV/SNP haplotypes from genotype data'", Bioinformatics, vol. 26, No. 11,1, Jun. 1, 2010, 1437-1445.

Sun, Guihua et al., "SNPs in human miRNA genes affect biogenesis and function", RNA, 15(9), 2009, 1640-1651.

Sweet-Kind Singer, J. A. et al., "Log-penalized linear regression", IEEE International Symposium on Information Theory, 2003. Proceedings, 2003, 286.

Tamura, et al., "Sibling Incest and formulation of paternity probability: case report", Legal Medicine, 2000, vol. 2, p. 189-196.

Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.

Tang, N. et al., "Detection of Fetal-Derived Paternally Inherited X-Chromosome Polymorphisms in Maternal Plasma", Clinical Chemistry, 45 (11), 1999, 2033-2035.

Thomas, M.R. et al., "The Time of Appearance and Disappearance of Fetal DNA from the Maternal Circulation", Prenatal Diagnosis, 15, 1995, 641-646.

Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.

Tong, Yu K. et al., "Noninvasive Prenatal Detection of Trisomy 21 by Epigenetic-Genetic Chromosome-Dosage Approach", Clinical Chemistry, 56(1), 2010, 90-98.

Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.

Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.

Turner, E. et al., "Massively Parallel Exon Capture and Library-Free Resequencing Across 16 Genomes", Nature Methods, 6 (5), 2009, 315-316.

(56) References Cited

OTHER PUBLICATIONS

Vallone, Peter, "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Wells, D, "Microarray for Analysis and Diagnosis of Human Embryos", 12th International Congress on Prenatal Diagnosis and Therapy, Budapest, Hungary, 2004, 9-17.
Wells, Dagan, "Advances in Preimplantation Genetic Diagnosis", European Journal of Obstetrics and Gynecology and Reproductive Biology, 115S, 2004, S97-S101.
Wells, Dagan, "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L., "Preimplantation Genetic Diagnosis and Chromosome Analysis of Blastomeres Using Comparative Genomic Hybridization", Human Reproduction Update, 11 (1), 2005, 33-41.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Zhang, Rui et al., "Quantifying RNA allelic ratios by microfluidic multiplex PCR and sequencing", Nature Methods, 11(1), 2014, 51-56.
Zhao, Xiaojun et al., "An Integrated View of Copy Number and Allelic Alterations in the Cancer Genome Using Single Nucleotide Polymorphism Arrays", Cancer Research,64, 2004, 3060-3071.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
U.S. Appl. No. 11/496,982 2007/0027636, filed Jul. 31, 2006 Feb. 1, 2007, System and method for using genetic, phenotypic and clinical data to make predictions for clinical or lifestyle decisions.
U.S. Appl. No. 11/634,550 2007/0178501, filed Dec. 6, 2006 Aug. 2, 2007, System and method for integrating and validating genotypic, phenotypic and medical information into a database according to a standard ontology.
U.S. Appl. No. 12/076,348 2008/0243398 U.S. Pat. No. 8,515,679, filed Mar. 17, 2008 Oct. 2, 2008 Aug. 20, 2013, System and Method for Cleaning Noisy Genetic Data Determining Chromosome Copy Number.
U.S. Appl. No. 13/793,133 2013/0255369 U.S. Pat. No. 9,424,392, filed Mar. 11, 2013 Sep. 26, 2013 Aug. 23, 2016, System and Method for Cleaning Noisy Genetic Data From Target Individuals Using Genetic Data From Genetically Related Individuals.
U.S. Appl. No. 14/092,457 2014/0087385 U.S. Pat. No. 9,436,611, filed Nov. 27, 2013 Mar. 27, 2014 Aug. 30, 2016, System and Method for Cleaning Noisy Genetic Data From Target Individuals Using Genetic Data From Genetically Related Individuals.
U.S. Appl. No. 14/156,433 2014/0193816, filed Jan. 4, 2014 Jul. 10, 2014, System and Method for Cleaning Noisy Genetic Data From Target Individuals Using Genetic Data From Genetically Related Individuals.
U.S. Appl. No. 14/286,895 2014/0256569, filed Mar. 23, 2014 Sep. 11, 2013, System and Method for Cleaning Noisy Genetic Data From Target Individuals Using Genetic Data From Genetically Related Individuals.
U.S. Appl. No. 15/187,555 2016-0298188, filed Jul. 20, 2016 Oct. 13, 2016, System and Method for Cleaning Noisy Genetic Data From Target Individuals Using Genetic Data From Genetically Related Individuals.
U.S. Appl. No. 15/191,197 2016-0369345, filed Jun. 23, 2016 Dec. 22, 2016, System and Method for Cleaning Noisy Genetic Data From Target Individuals Using Genetic Data From Genetically Related Individuals.
U.S. Appl. No. 15/293,257 2017-0029893 U.S. Pat. No. 9,695,477, filed Oct. 13, 2016 Feb. 2, 2017 Jul. 4, 2017, System and Method for Cleaning Noisy Genetic Data From Target Individuals Using Genetic Data From Genetically Related Individuals.
U.S. Appl. No. 15/413,200 2017-0175187, filed Jan. 23, 2017 Jun. 22, 2017, System and Method for Cleaning Noisy Genetic Data and Determining Chromosome Copy Number.
U.S. Appl. No. 15/446,778 2017-0166971, filed Mar. 1, 2017 Jun. 15, 2017, System and Method for Cleaning Noisy Genetic Data and Determining Chromosome Copy Number.
U.S. Appl. No. 15/676,233, filed Aug. 14, 2017, System and Method for Cleaning Noisy Genetic Data and Determining Chromosome Copy Number.
U.S. Appl. No. 15/676,759, filed Aug. 14, 2017, System and Method for Cleaning Noisy Genetic Data and Determining Chromosome Copy Number.
U.S. Appl. No. 15/688,604, filed Aug. 28, 2017, System and Method for Cleaning Noisy Genetic Data and Determining Chromosome Copy Number.
U.S. Appl. No. 15/881,263, filed Jan. 26, 2018, System and Method for Cleaning Noisy Genetic Data and Determining Chromosome Copy Number.
U.S. Appl. No. 15/887,746, filed Feb. 2, 2018, System and Method for Cleaning Noisy Genetic Data and Determining Chromosome Copy Number.
U.S. Appl. No. 15/881,384, filed Jan. 26, 2018, System and Method for Cleaning Noisy Genetic Data and Determining Chromosome Copy Number.
U.S. Appl. No. 15/881,488, filed Jan. 26, 2018, System and Method for Cleaning Noisy Genetic Data and Determining Chromosome Copy Number.
U.S. Appl. No. 13/846,111 2013/0225422 U.S. Pat. No. 9,639,657, filed Mar. 18, 2013 Aug. 29, 2013 May 2, 2017, Methods for Allele Calling and Ploidy Calling.

(56) References Cited

OTHER PUBLICATIONS

U.S. Appl. No. 13/968,302 2014/0051585, filed Aug. 15, 2013 Feb. 20, 2014, Methods and Compositions for Reducing Genetic Library Contamination.
U.S. Appl. No. 14/044,434 2014/0094373, filed Oct. 2, 2013 Apr. 3, 2014, Highly Multiplex PCR Methods and Compositions.
U.S. Appl. No. 14/225,356 2014/0206552, filed Mar. 25, 2014 Jul. 24, 2014, Methods for Preimplantation Genetic Diagnosis by Sequencing.
U.S. Appl. No. 14/546,321 2015/0072872, filed Nov. 18, 2014 Mar. 12, 2015, Methods for Non-Invasive Prenatal Ploidy Calling.
U.S. Appl. No. 14/866,223 2016-0024564, filed Sep. 25, 2015 Jan. 28, 2016, Methods for Non-Invasive Prenatal Ploidy Calling.
U.S. Appl. No. 14/983,128 2016-0171152, filed Dec. 29, 2015 Jun. 16, 2016, Methods for Non-Invasive Prenatal Ploidy Calling.
U.S. Appl. No. 15/243,915 2016-0357904, filed Aug. 22, 2016 Dec. 8, 2016, Methods for Non-Invasive Prenatal Ploidy Calling.
U.S. Appl. No. 15/252,795 2016-0369346, filed Aug. 31, 2016 Dec. 22, 2016, Methods for Non-Invasive Prenatal Ploidy Calling.
U.S. Appl. No. 15/343,003 2017-0076038, filed Nov. 3, 2016 Mar. 16, 2017, Methods for Non-Invasive Prenatal Ploidy Calling.
U.S. Appl. No. 15/586,013 2017-0242960-A1, filed May 3, 2017 Aug. 24, 2017, Methods for Non-Invasive Prenatal Ploidy Calling.
U.S. Appl. No. 15/724,020, filed Oct. 3, 2017, Methoods for Non-Invasive Prenatal Ploidy Calling.
U.S. Appl. No. 15/727,428, filed Oct. 6, 2017, Methods for Non-Invasive Prenatal Ploidy Calliing.
U.S. Appl. No. 15/805,871, filed Nov. 7, 2017, Methods for Non-Invasive Prenatal Ploidy Calling.
U.S. Appl. No. 15/806,047, filed Nov. 7, 2017, Methods for Non-Invasive Prenatal Ploidy Calling.
U.S. Appl. No. 13/970,436 2014/0100126, filed Aug. 19, 2013 Apr. 10, 2014, Method for Non-Invasive Prenatal Testing Using Parental Mosaicism Data.
U.S. Appl. No. 15/433,950 2017-0177786, filed Feb. 15, 2017 Jun. 22, 2017, Method for Non-Invasive Prenatal Testing Using Parental Mosaicism Data.
U.S. Appl. No. 13/793,316 2014/0065621, field Mar. 11, 2013 Mar. 6, 2014, Methods for Increasing Fetal Fraction in Maternal Blood.
U.S. Appl. No. 14/498,629 2015/0147815 U.S. Pat. No. 9,499,870, filed Sep. 26, 2014 May 28, 2015 Nov. 22, 2016, Cell Free Dna Diagnostic Testing Standards.
U.S. Appl. No. 14/732,632, filed Nov. 12, 2014, Systems and Methods for Detection of Aneuploidy.
U.S. Appl. No. 15/887,864, filed Feb. 2, 2018, Systems and Methods for Detection of Aneuploidy.
U.S. Appl. No. 15/887,914, filed Feb. 2, 2018, Systems and Methods for Detection of Aneuploidy.
U.S. Appl. No. 14/538,982 20015/0322507 U.S. Pat. No. 9,677,118, filed Nov. 24, 2014 Nov. 12, 2015 Jun. 13, 2017, Methods for Simultaneous Amplification of Target Loci.
U.S. Appl. No. 14/692,703 2017-0107576, filed Apr. 21, 2015 Apr. 20, 2017, Detecting Mutations and Ploidy in Chromosome Segments.
U.S. Appl. No. 14/882,763 2016-0333416, filed Oct. 14, 2015 Nov. 17, 2015, Detecting Cancer Mutations and Aneuploidy in Chromosome Segments.
U.S. Appl. No. 14/918,544 2016-0369333, filed Oct. 20, 2015 Dec. 22, 2016, Methods for Simultaneous Amplification of Target Loci.
U.S. Appl. No. 15/336,630 2017-0145474, filed Oct. 27, 2016 May 25, 2017, Methods for Simultaneous Amplification of Target Loci.
U.S. Appl. No. 15/573,800, filed May 10, 2016, Methods and Compositions for Determining Ploidy.
U.S. Appl. No. 15/186,774 2016-0371428, filed Jun. 20, 2016 Dec. 22, 2016, Systems and Methods for Determining Aneuploidy Risk Using Sample Fetal Fraction.
U.S. Appl. No. 15/716,058, filed Sep. 26, 2017, Compositions and Methods for Identifying Nucleic Acid Molecules.
U.S. Appl. No. 15/716,331, filed Sep. 26, 2017, Compositions and Methods for Identifying Nucleic Acid Molecules.

Abbosh, C. et al., "Phylogenetic ctDNA analysis depicts early-stage lung cancer evolution", Nature, vol. 545, May 25, 2017, 446-451.
Butler, J. et al., "The Development of Reduced Size STR Amplicons as Tools for Analysis of Degraded DNA*", Journal of Forensic Sciences, vol. 48, No. 5, 2003, 1054-1064.
De Bruin, E. et al., "Spatial and temporal diversity in genomic instability processes defines lung cancer evolution", Science, vol. 346, No. 6206, Oct. 10, 2014, 251-256.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Hawkins, T. et al., "Whole genome amplification—applications and advances", Current Opinion in Biotechnology, 13, 2002, 65-67.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Rogaeva, E. et al., "The Solved and Unsolved Mysteries of the Genetics of Early-Onset Alzheimer's Disease", NeuroMolecular Medicine, vol. 2, 2002, 1-10.
Sahota, A., "Evaluation of Seven PCR-Based Assays for the Analysis of Microchimerism", Clinical Biochemistry, vol. 31, No. 8., 1998, 641-645.
Ten Bosch, J., "Keeping Up With the Next Generation Massively Parallel Sequencing in Clinical Diagnostics", Journal of Molecular Diagnostics, vol. 10, No. 6, 2008, 484-492.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.
Wright, C. et al., "The use of cell-free fetal nucleic acids in maternal blood for non-invasive prenatal diagnosis", Human Reproduction Update, vol. 15, No. 1, 2009, 139-151.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Alaeddini, R. et al., "Forensic implications of genetic analyses from degraded DNA—A review", Forensic Science International: Genetics, vol. 4, 2010, 148-157.
Deutsch, S. et al., "Detection of aneuploidies by paralogous sequence quantification", J Med Genet, vol. 41, 2004, 908-915.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Illumina, "Patent Owner Illumina's Preliminary Response to Petition", Oct. 17, 2018, 75 pgs.
Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, "Plaintiff/Counterclaim—Defendant Illumina, Inc.'s Patent L.R. 3-3 Contentions for U.S. Patent Preliminary Invalidity Contentions for U.S. Pat. No. 8,682,592", Oct. 9, 2018, 81 pages.

(56) References Cited

OTHER PUBLICATIONS

Lo, Y., "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.

Lu, I. et al., "Establishment of a system based on universal multiplex-PCR for screening genetically modified crops", Anal. Bioanal. Chem, vol. 396, Oct. 24, 2009, 2055-2064.

Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.

Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.

Minkoff, E. et al., "Stem Cells, Cell Division, and Cancer", Biology Today Third Edition, Chapter 12, 2004, 10 pages.

Natera, Inc., "Defendant Natera, Inc.'s Invalidity Contentions Under Patent L.R. 3-3; Document Production Accompanying Invalidity Contentions Under Patent L.R. 3-4", Aug. 20, 2018, 17 pages.

Natera, Inc., "Exhibit 8 EHRICH Invalidity Chart", Aug. 20, 2018, 16 pages.

Natera, Inc., "Petitioner Reply Per Board Order of Nov. 2, 2018 (Paper No. 10)", Nov. 9, 2018, 8 pgs.

Shen, R. et al., "High-throughput SNP genotyping on universal bead arrays", Mutation Research, vol. 573, Feb. 11, 2005, 70-82.

Wang, D. G. et al., "Large-Scale Identification, Mapping, and Genotyping of Single-Nucleotide Polymorphisms in the Human Genome", Science, vol. 280, May 15, 1998, 1077-1082.

Wang, T.L. et al., "Digital karyotyping", PNAS, vol. 99, No. 25, Dec. 10, 2002, 16156-16161.

Zimmermann, B., "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.

Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.

Riley, D. E., "DNA Testing: An Introduction for Non-Scientists An Illustrated Explanation", Scientific Testimony: An Online Journal, http://www.scientific.org/tutorials/articles/riley/riley.html, Apr. 6, 2005, 22 pages.

Tu, J. et al., "Pair-barcode high-throughput sequencing for large-scale multiplexed sample analysis", BMC Genomics, vol. 13, No. 43, Jan. 25, 2012, 1-9.

Cansar, "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Choi, M. et al., "Genetic diagnosis by whole exome capture and massively parallel DNA sequencing", PNAS, vol. 106, No. 45, Nov. 10, 2009, 19096-19101.

Garcia-Murillas, I. et al., "Mutation tracking in circulating tumor DNA predicts relapse in early breast cancer", Science Translational Medicine, vol. 7, No. 302, Aug. 26, 2015, 1-2.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T., "Next generation sequencing technologies", Drug Discovery Today: Technologies, vol. 2, No. 3, 2005, 255-260.

Kim, H. et al., "Whole-genome and multisector exome sequencing of primary and post-treatment glioblastoma reveals patterns of tumor evolution", Genome Research, vol. 25, No. 3, Feb. 3, 2015, 316-327.

Leary, R. J. et al., "Development of Personalized Tumor Biomarkers Using Massively Parallel Sequencing", Science Translational Medicine, vol. 2, No. 20, Feb. 24, 2010, 1-8.

Ma, Xiaotu et al., "Rise and fall of subclones from diagnosis to relapse in pediatric B-acute lymphoblastic leukaemia", Nature Communications, vol. 6, Mar. 19, 2015, 1-12.

Margulies, M. et al., "Genome sequencing in microfabricated high-density picolitre reactors", Nature, vol. 437, Sep. 15, 2005, 376-380.

Margulies, M. et al., "Genome sequencing in microfabricated high-density picolitre reactors plus Supplemental Methods", Nature, vol. 437, Sep. 15, 2005, 40 pgs.

McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.

Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.

Popova, T. et al., "Genome Alteration Print (GAP): a tool to visualize and mine complex cancer genomic profiles obtained by SNP arrays", Genome Biology, vol. 10, R128, Nov. 11, 2009, 1-14.

Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.

Samango Sprouse, C. et al., "SNP-based non-invasive prenatal testing detects sex chromosome aneuploidies with high accuracy", Prenatal Diagnosis, vol. 33, 2013, 643-649.

Anker, P. et al., "Detection of circulating tumour DNA in the blood (plasma/serum) of cancer patients", Cancer and Metastasis Reviews, vol. 18, 1999, 65-73.

Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.

Bianchi, D. W. et al., "Genome-Wide Fetal Aneuploidy Detection by Maternal Plasma DNA Sequencing", Obstetrics & Gynecology, vol. 119, No. 5, May 2012, 890-901.

Chan, K.C. et al., "Size Distributions of Maternal and Fetal DNA in Maternal Plasma", Clinical Chemistry, vol. 50, No. 1, 2004, 88-92.

Chen, X. Q. et al., "Microsatallite alterations in plasma DNA of small cell lung cancer patients", Nature Medicine, vol. 2, No. 9, Sep. 1996, 1033-1035.

Dodge, Y., "Bayes' Theorem", The Concise Encyclopedia of Statistics, 2008, 30-31.

Geiss, G. K. et al., "Direct multiplexed measurement of gene expression with color-coded probe pairs", Nature Biotechnology, vol. 26, No. 3, Feb. 17, 2008, 317-325.

Gunderson, K. L. et al., "A genome-wide scalable SNP genotyping assay using microarray technology", Nature Genetics, vol. 37, No. 5, May 2005, 549-554.

Jenkins, S. et al., "High-throughput SNP genotyping", Comparative and Functional Genomics, vol. 3, Dec. 5, 2001, 57-66.

Kwok, P. Y., "High-throughput genotyping assay approaches", Pharmacogenomics, vol. 1, No. 1, 2000, 1-5.

Lander, E. S. et al., "Initial sequencing and analysis of the human genome", Nature, vol. 409, Feb. 15, 2001, 860-921.

Levsky, J. M. et al., "Fluorescence in situ hybridization: past, present and future", Journal of Cell Science, vol. 116, No. 14, 2003, 2833-2838.

Palomaki, G. E. et al., "DNA sequencing of maternal plasma to detect Down syndrome: An international clinical validation study", Genetics in Medicine, vol. 13, No. 1, Nov. 2011, 913-920.

Quinn, G. P. et al., "Experimental Design and Data Analysis for Biologists", Graphical Exploration of Data, 2002, 64-67.

(56) References Cited

OTHER PUBLICATIONS

Tebbutt, S. J. et al., "Microarray genotyping resource to determine population stratification in genetic association studies of complex disease", BioTechniques, vol. 37, Dec. 2004, 977-985.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Ballif, B. C. et al., "Detection of Low-Level Mosaicism by Array CGH in Routine Diagnostic Specimens", American Journal of Medical Genetics Part A, vol. 140A, 2006, pp. 2757-2767.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Burnham, P. et al., "Myriad Applications of Circulating Cell-Free DNA in Precision Organ Transplant Monitoring", Annals of the American Thoracic Society, vol. 14, Supplement 3, Sep. 2017, pp. S237-S241.
Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, pp. 1679-1686.
Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, pp. 1263-1275.
Coombes, R. C., "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.
Donaghue, C. et al., "Detection of mosaicism for primary trisomies in prenatal samples by QF-PCR and karyotype analysis", Prenatal Diagnosis, vol. 25, 2005, pp. 65-72.
Kunishima, S. et al., "First description of somatic mosaicism in MYH9 disorders", British Journal of Haematology, vol. 128, 2005, pp. 360-365.
Lo, Y-M D., "Non-invasive prenatal diagnosis using fetal cells in maternal blood", J. Clin. Pathol., vol. 47, 1994, pp. 1060-1065.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-Spy 2 Trial", Cancer Research, vol. 79, No. 4 Supplement, Feb. 15, 2019.
Mardis, E. R., "The impact of next-generation sequencing technology on genetics", Trends in Genetics, vol. 24, No. 3, Feb. 11, 2008, pp. 133-141.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
NG, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T., "A high-plex PCR approach for massively parallel sequencing", BioTechniques, vol. 55, No. 2, Aug. 2013, pp. 69-74.
Papadopoulou, E. et al., "Cell-Free DNA and RNA in Plasma as a New Molecular Marker for Prostate Cancer", Oncology Research, vol. 14, 2004, pp. 439-445.
Poirier, K. et al., "Maternal mosaicism for mutations in the ARX gene in a family with X linked mental retardation", Human Genetics, vol. 118, Aug. 3, 2005, pp. 45-48.
Poon, L. L. et al., "Differential DNA Methylation between Fetus and Mother as a Strategy for Detecting Fetal DNA in Maternal Plasma", Clinical Chemistry, vol. 48, No. 1, 2002, pp. 35-41.
Reinert, T. et al., "Analysis of circulating tumour DNA to monitor disease burden following colorectal cancer surgery", Gut, vol. 65, 2016, pp. 625-634.
Riva, F., "Patient-Specific Circulating Tumor DNA Detection during Neoadjuvant Chemotherapy in Triple-Negative Breast Cancer", Clinical Chemistry, vol. 63, No. 3, 2017, pp. 691-699.
Saker, A. et al., "Genetic characterisation of circulating fetal cells allows non-invasive prenatal diagnosis of cystic fibrosis", Prenatal Diagnosis, vol. 26, Jul. 11, 2006, pp. 906-916.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, pp. S178-S179.
Wikipedia, "Buffy coat", Retrieved from "https://en.wikipedia.orgJw/index.php?title=Buffy_coat&oldid=900992886 ", Jun. 9, 2019, 2 pages.
Alberts, B. et al., "Chapter 20: Germ Cells and Fertilization", Molecular Biology of the Cell, Fourth Edition, 2002, pp. 1127-1156.
Alberts, B. et al., "Chapter 4: DNA and Chromosomes", Molecular Biology of the Cell, Fourth Edition, 2002, pp. 191-234.
Antonarakis, S. E. et al., "Chromosome 21 and Down Syndrome: From Genomics to Pathophysiology", Nature Reviews Genetics, vol. 5, Oct 2004, pp. 725-738.
Beroud, C. et al., "Prenatal diagnosis of spinal muscular atrophy by genetic analysis of circulating fetal cells", The Lancet, vol. 361, Mar. 22, 2003, pp. 1013-1014.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, pp. 236-242.
Dietmaier, W. et al., "Multiple Mutation Analyses in Single Tumor Cells with Improved Whole Genome Amplification", American Journal of Pathology, vol. 154, No. 1, Jan 1999, pp. 83-95.
Everitt, B. S., "Medical Statistics From A to Z", 2003, 3 pages.
Hartwell, L. H. et al., "Chapter 11: The Direct Detection of Genotype Distinguishes Individual Genomes", Genetics: From Genes to Genomes, Second Edition, 2004, pp. 371-414.
Hartwell, L. H. et al., "Chapter 13: Chromosomal Rearrangements and Changes in Chromosome Number Reshape Eukaryotic Genomes", Genetics: From Genes to Genomes, Second Edition, 2004, pp. 441-486.
Hattori, M. et al., "The DNA sequence of human chromosome 21", Nature, vol. 405, May 18, 2000, pp. 311-319.
Illumina, "Petition for Inter Partes Review of U.S. Pat. No. 8,682,592", Jun. 13, 2019, 91 pages.
Illumina, Inc., "Declaration of David Peters, Ph.D. In Support of Petition for Inter Partes Review of U.S. Pat. No. 8,682,592", Jun. 13, 2019, 136 pages.
Illumina, Inc. V. Natera, Inc., "Order Re: Claim Construction", Jan. 30, 2019, 16 pages.
Kamat, A. A. et al., "Quantification of total plasma cell-free DNA in ovarian cancer using real-time PCR", Ann N.Y. Acad Sci., vol. 1075, Sep. 2006, pp. 230-234.
Munne, S. et al., "Improved implantation after preimplantation genetic diagnosis of aneuploidy", Reproductive BioMedicine Online, vol. 7., No. 1., May 15, 2003, pp. 91-97.
Natera, Inc., "Declaration of Sandra L. Haberny", May 16, 2019, 3 pages.
Natera, Inc., "Exhibits A-H to Haberny Declaration", May 16, 2019, 192 pages.
Natera, Inc., "Motion to Dismiss", May 16, 2019, 2 pages.
Natera, Inc., "Natera Inc.'s First Amended Answer, Affirmative Defenses and Counterclaims", Aug. 16, 2018, 28 pages.
Natera, Inc., "Natera, Inc.'s Supplemental Objections and Response to Plaintiff Illumina, Inc.'s Interrogatory No. 8", Mar. 20, 2019, 29 pages.
Natera, Inc., "Opening Brief in Support of Motion to Dismiss", May 16, 2019, 26 pages.
Pastinen, T. et al., "Minisequencing: A Specific Tool for DNA Analysis and Diagnostics on Oligonucleotide Arrays", Genome Research, vol. 7, 1997, pp. 606-614.
Peters, D., "List of Materials Considered by David Peters, Ph.D.", Jun. 13, 2019, 2 pages.
Sham, P. et al., "DNA Pooling: A Tool for Large-Scale Association Studies", Nature Reviews Genetics, vol. 3, Nov. 2002, pp. 862-871.

(56) References Cited

OTHER PUBLICATIONS

Snyder, T. M. et al., "Universal noninvasive detection of solid organ transplant rejection", PNAS, vol. 108, No. 15, Apr. 12, 2011, pp. 6229-6234.
The International Hapmap Consort, "The International HapMap Project", Nature, vol. 426, Dec. 18, 2003, pp. 789-796.
Tiersch, T. R. et al., "Reference Standards for Flow Cytometry and Application in Comparative Studies of Nuclear DNA Content", Cytometry, vol. 10, Mar. 21, 1989, pp. 706-710.
Weiss, C. A., "Chapter 8: Confidence Intervals for One Population Mean", Introductory Statistics, Sixth Edition, 2002, pp. 340-381.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Zhang, L. et al., "Whole genome amplification from a single cell: Implications for genetic analysis", Proc. Nat'l. Acad. Sci. USA, vol. 89, Jul. 1992, pp. 5847-5851.

\* cited by examiner

METHODS FOR NON-INVASIVE PRENATAL PLOIDY CALLING

RELATED APPLICATIONS

This application is a continuation of U.S. Utility application Ser. No. 14/983,128, filed Dec. 29, 2015, which is a continuation of U.S. Utility application Ser. No. 14/080,656, filed Nov. 14, 2013, which is a continuation of U.S. Utility application Ser. No. 13/896,293, filed May 16, 2013, which is a continuation of U.S. Utility application Ser. No. 13/499,086, filed Mar. 29, 2012, which is a national phase filing under 35 U.S.C. § 371 of International Application No. PCT/US10/50824, filed Sep. 30, 2010, which claims the benefit of the following U.S. Provisional Patent Applications: Ser. No. 61/277,876, filed Sep. 30, 2009; Ser. No. 61/337,931, filed Feb. 12, 2010; and Ser. No. 61/395,850, filed May 18, 2010; all the disclosures thereof are incorporated by reference herein in their entirety.

BACKGROUND

A human being normally has two sets of 23 chromosomes in every somatic cell, with one copy coming from each parent. Aneuploidy, a state where a cell has the wrong number of chromosomes, is responsible for a significant percentage of children born with genetic conditions. Detection of chromosomal abnormalities can identify individuals, including fetuses or embryos, with conditions such as Down syndrome, Edwards syndrome, Klinefelters syndrome, and Turner syndrome, among others. Since chromosomal abnormalities are generally undesirable, the detection of such a chromosomal abnormality in a fetus may provide the basis for the decision to terminate a pregnancy.

Prenatal diagnosis can alert physicians and parents to abnormalities in growing fetuses. Some currently available methods, such as amniocentesis and chorionic villus sampling (CVS), are able to diagnose genetic defects with high accuracy; however, they may carry a risk of spontaneous abortion. Other methods can indirectly estimate a risk of certain genetic defects non-invasively, for example from hormone levels in maternal blood and/or from ultrasound data, however their accuracies are much lower. It has recently been discovered that cell-free fetal DNA and intact fetal cells can enter maternal blood circulation. This provides an opportunity to directly measure genetic information about a fetus, specifically the aneuploidy state of the fetus, in a manner which is non-invasive, for example from a maternal blood draw.

SUMMARY

Methods for non-invasive prenatal ploidy calling are disclosed herein. In an embodiment of the present disclosure, methods are disclosed for the determination of the ploidy state of a target individual where the measured genetic material of the target is contaminated with genetic material of the mother, by using the knowledge of the maternal genetic data. This is in contrast to methods that are able to determine the ploidy state of a target individual from genetic data that is noisy due to poor measurements; the contamination in this data is random. This is also in contrast to methods that are able to determine the ploidy state of a target individual from genetic data that is difficult to interpret because of contamination by DNA from unrelated individuals; the contamination in that data is genetically random. In an embodiment, the methods disclosed herein are able to determine the ploidy state of a target individual when the difficulty of interpretation is due to contamination of DNA from a parent; the contamination in this data is at least half identical to the target data, and is therefore difficult to correct for. In order to achieve this end, in an embodiment a method of the present disclosure uses the knowledge of the contaminating maternal genotype to create a model of the expected genetic measurements given a mixture of the maternal and the target genetic material, wherein the target genetic data is not known a priori. This step is not necessary where the uncertainty in the genetic data is due to random noise.

According to aspects illustrated herein, there is provided a method that enables the determination of the ploidy state of a target individual using genetic material from the target individual when the target individual's genetic material is contaminated by other genetic material. In an embodiment, the target individual is a fetus, and the target individual's genetic data comprises free floating DNA found in maternal blood, and the contaminating genetic material comprises free floating maternal DNA also found in maternal blood. In an embodiment, the target individual is a fetus, and the target individual's genetic data comprises DNA found in fetal cells found in maternal blood, and the contaminating genetic material comprises DNA found in maternal cells also found in maternal blood. In an embodiment, the target individual is a fetus, and the determination of the ploidy state is done in the context of non-invasive prenatal diagnosis, and where a clinical decision is made based on the ploidy state determination. In an embodiment, genetic data from one or both parents of the target individual is used in the determination of the ploidy state of the target. In an embodiment, the chromosomes of interest include chromosomes 13, 18, 21, X and Y. In an embodiment, the determination is transformed into a report which may be sent to a relevant healthcare practitioner. In an embodiment, the series of steps outlined above result in a transformation of the genetic matter of a pregnant mother and the father into an actionable decision that results in a pregnancy being continued or terminated. In an embodiment, the ploidy state determination is used to make a clinical decision. In an embodiment the clinical decision may be to terminate a pregnancy where the fetus is found to have a genetic abnormality.

While the disclosure focuses on genetic data from human subjects, and more specifically on developing fetuses, as well as related individuals, it should be noted that the methods disclosed apply to the genetic data of a range of organisms, in a range of contexts. The techniques described for making ploidy determination are most relevant in the context of prenatal diagnosis in conjunction with amniocentesis, chorion villus biopsy, fetal tissue sampling, and non-invasive prenatal diagnosis, where a small quantity of fetal genetic material is isolated from maternal blood, for example prenatal serum screens, the triple test, the quad test. The use of this method may facilitate diagnoses focusing on inheritable diseases, chromosome copy number predictions, increased likelihoods of defects or abnormalities, as well as making predictions of susceptibility to various disease- and non-disease phenotypes for individuals to enhance clinical and lifestyle decisions.

In an embodiment of the present disclosure, the fetal or embryonic genomic data, with or without the use of genetic data from related individuals, can be used to detect if the cell is aneuploid, that is, where the wrong number of one or more autosomal chromosomes are present in an individual, and/or if the wrong number of sexual chromosomes are present in the individual. The genetic data can also be used to detect for uniparental disomy, a condition in which two of a given chromosome are present, both of which originate from one parent. This is done by creating a set of hypotheses about the potential states of the DNA, and testing to see which hypothesis has the highest probability of being true given the measured data.

In an embodiment of the present disclosure, the small amount of genetic material of a fetus, which may be mixed with maternal genetic material, may be transformed through amplification into a large amount of genetic material that encodes similar or identical genetic data. The genetic data contained molecularly in the large amount of genetic material may be transformed into raw genetic data in the form of digital signals, optionally stored in computer memory, by way of a genotyping method. The raw genetic data may be transformed, by way of the PARENTAL SUPPORT™ method, into copy number calls for one or a number of chromosomes, also optionally stored in computer memory. The copy number call may be transformed into a report for a physician, who may then act on the information in the report.

In an embodiment of the present disclosure, the direct measurements of genetic material, amplified or unamplified, present at a plurality of loci, can be used to detect for monosomy, uniparental disomy, matched trisomy, unmatched trisomy, tetrasomy, and other aneuploidy states. One embodiment of the present disclosure takes advantage of the fact that under some conditions, the average level of amplification and measurement signal output is invariant across the chromosomes, and thus the average amount of genetic material measured at a set of neighboring loci will be proportional to the number of homologous chromosomes present, and the ploidy state may be called in a statistically significant fashion. In another embodiment, different alleles have a statistically different characteristic amplification profiles given a certain parent context and a certain ploidy state; these characteristic differences can be used to determine the ploidy state of the chromosome.

In an embodiment of the present disclosure, calculated, phased, reconstructed and/or determined genetic data from the target individual and/or from one or more related individuals may be used as input for a ploidy calling aspect of the present disclosure.

In an embodiment, a method for determining a copy number of a chromosome of interest in a target individual, using genotypic measurements made on genetic material from the target individual, wherein the genetic material of the target individual is mixed with genetic material from the mother of the target individual, comprises obtaining genotypic data for a set of SNPs of the parents of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and the genetic data of the parents of the target individual; and using the determined probabilities of each hypothesis to determine the most likely copy number of the chromosome of interest in the target individual.

In an embodiment, the target individual is a fetus. In an embodiment, the copy number determination is used to make a clinical decision. In an embodiment, the target individual is a fetus, and the clinical decision is to terminate a pregnancy where the fetus is found to have a genetic abnormality, or to not terminate the pregnancy where the fetus is not found to have a genetic abnormality. In an embodiment, the set of SNPs comprises a plurality of SNPs from the chromosome of interest, and a plurality of SNPs from at least one chromosome that is expected to be disomic on the target individual.

In an embodiment, the step of determining, on the computer, the probability of each of the hypotheses comprises using the genotypic data of the parents to determine parental contexts for each of the SNPs; grouping the genotypic measurements of the mixed sample into the parental contexts; using the grouped genotypic measurements from at least one chromosome that is expected to be disomic to determine a platform response; using the grouped genotypic measurements from at least one chromosome that is expected to be disomic to determine a ratio of fetal to maternal DNA in the mixed sample; using the determined platform response and the determined ratio to predict an expected distribution of SNP measurements for each set of SNPs in each parental context under each hypothesis; and calculating the probabilities that each of the hypotheses is true given the platform response, and given the ratio, and given the grouped genotypic measurements of the mixed sample, and given the predicted expected distributions, for each parental context, for each hypothesis.

In an embodiment, the chromosome of interest is selected from the group consisting of chromosome 13, chromosome 18, chromosome 21, the X chromosome, the Y chromosome, and combinations thereof. In an embodiment, the method is used to determine the copy number of a number of chromosomes in the target individual, where the number is selected from the group consisting of one, two, three, four, five, six, seven, eight, nine, ten, eleven, twelve, thirteen, fourteen, fifteen, sixteen, seventeen, eighteen, nineteen, twenty, twenty one, twenty two, and twenty three.

In an embodiment, the mixed sample is maternal blood, maternal plasma or some other substance taken from a pregnant mother. In an embodiment, the target individual's genetic material is free floating DNA found in maternal blood or serum. In an embodiment, the target individual's genetic material is nuclear DNA found in one or more cells from the target individual. In an embodiment, a confidence is computed for the chromosome copy number determination. In an embodiment, the ratio of fetal to maternal DNA in the mixed sample is determined for individual chromosomes.

In an embodiment, the step of obtaining of genotypic data, and/or the step of making genotypic measurements is done by measuring genetic material using techniques selected from the group consisting of padlock probes, circularizing probes, genotyping microarrays, SNP genotyping assays, chip based microarrays, bead based microarrays, other SNP microarrays, other genotyping methods, Sanger DNA sequencing, pyrosequencing, high throughput sequencing, reversible dye terminator sequencing, sequencing by ligation, sequencing by hybridization, other methods of DNA sequencing, other high throughput genotyping platforms, fluorescent in situ hybridization (FISH), comparative genomic hybridization (CGH), array CGH, and multiples or combinations thereof. In an embodiment, the step of measuring genetic material is done on genetic material that is amplified, prior to being measured, using a technique that is selected from the group consisting of Polymerase Chain Reaction (PCR), ligand mediated PCR, degenerative oligonucleotide primer PCR, Multiple Displacement Amplification (MDA), allele-specific PCR, allele-specific amplification techniques, bridge amplification, padlock probes, circularizing probes, and combinations thereof.

In an embodiment, the step of determining the copy number of the chromosome of interest is performed for the purpose of screening for a chromosomal condition where the chromosomal condition is selected from the group consisting of nullsomy, monosomy, disomy, uniparental disomy, euploidy, trisomy, matched trisomy, unmatched trisomy, maternal trisomy, paternal trisomy, tetrasomy, matched tetrasomy, unmatched tetrasomy, other aneuploidy, unbalanced translocation, balanced translocation, recombination, deletion, insertion, mosaicism, and combinations thereof.

In an embodiment, the method is used for the purpose of paternity testing.

In an embodiment, a method for determining a copy number of a chromosome of interest in a target individual, using genotypic measurements made on genetic material from the target individual, wherein the genetic material of the target individual is mixed with genetic material from the mother of the target individual, comprises obtaining genotypic data for a set of SNPs of the mother of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and the genetic data of the parents of the target individual; and using the determined probabilities of each hypothesis to determine the most likely copy number of the chromosome of interest in the target individual.

It will be recognized by a person of ordinary skill in the art, given the benefit of this disclosure, that various aspects and embodiments of this disclosure may be implemented in combination or separately.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3 is from chromosome 21 of the same sample as in FIG. 2, and the correct hypothesis is H210.

Figure 1A:
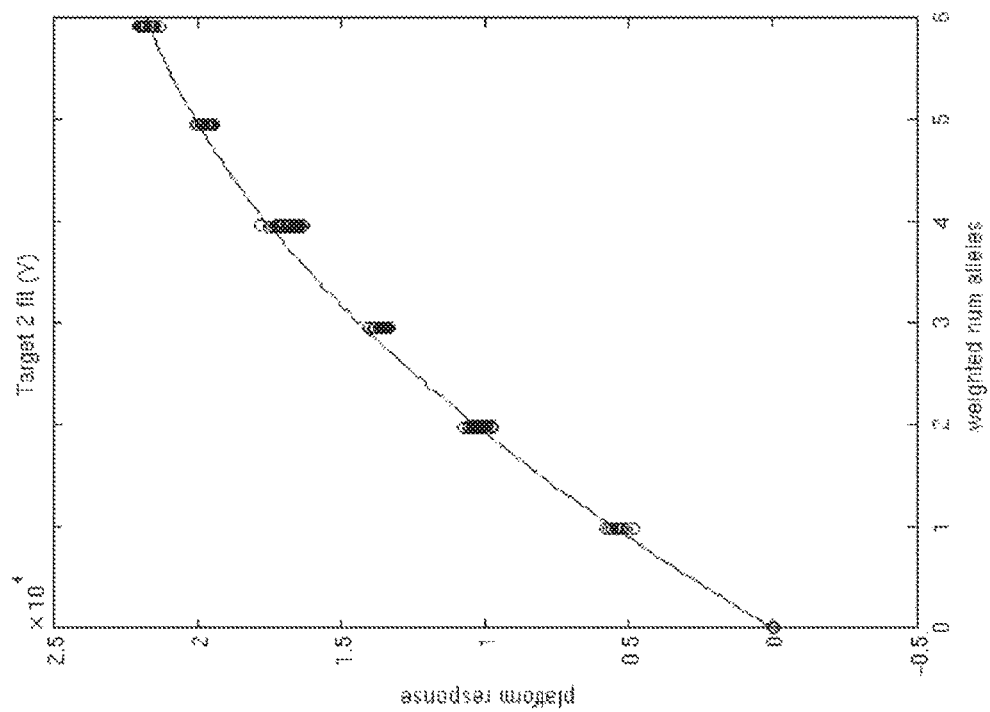
FIGS. 1A and 1B show a model fit for both X (left plot, FIG. 1A) and Y (right plot, FIG. 1B) channels in a sample with 40 percent DNA from the target individual.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In an embodiment of the present disclosure, the ploidy state of a target individual can be determined for one, some, or all chromosomes, in the individual. In one embodiment of the invention, the genetic material of the target individual is used to make the ploidy determination, and where the genetic material of the target individual is contaminated with genetic material of the mother of the target individual. In one embodiment of the invention, genetic data of one or both parents of the target individual, optionally including genetic data from other relatives of the target individual is used in the ploidy determination.

Copy number calling is the concept of determining the number and identity of chromosomes in an individual, either on a per cell basis, or in a bulk manner. In one embodiment of the invention, the amount of genetic material contained in a single cell, a small group of cells, or a sample of DNA may be used as a proxy for the number of chromosomes in the target individual. The present disclosure allows the determination of aneuploidy from the genetic material contained in a small sample of cells, or a small sample of DNA, provided the genome of at least one or both parents are available. Some aspects of the present disclosure use the concept of parental context, where the parental contexts describe, for a given SNP, the possible set of alleles that a child may have inherited from the parents. For each set of SNPs that belong to a given parental context, a specific statistical distribution of SNP measurements is expected, and that distribution will vary depending on the parental context and on the ploidy state of the chromosome segment on which the SNP is found. By analyzing the actual distributions of the SNPs in different parental contexts, and comparing them with the expected distribution of those SNPs for different ploidy state hypotheses, it is possible to calculate which ploidy state is most likely to be correct. This may be particularly useful in the case of prenatal diagnosis, wherein a limited amount of DNA is available, and where the determination of the ploidy state of a target, such as a fetus, has a high clinical impact.

A number of informatics techniques that may be appropriate to use in conjunction with the invention described in this disclosure are described in the following three references: U.S. Publication No. 2007/0184467, published on Aug. 9, 2007, U.S. Publication No. 2008/0243398, published on Oct. 2, 2008 and PCT Publication No. WO/2010/017214, published on Feb. 11, 2010. These references are referred to herein as Rabinowitz 2006, 2008 and 2009, respectively, and the methods described in these references, along with the methods described in this disclosure, may be collectively referred to as PARENTAL SUPPORT™.

DNA measurements, whether obtained by sequencing techniques, genotyping arrays, or any other technique, contain a degree of error. The relative confidence in a given DNA measurement is affected by many factors, including the amplification method, the technology used to measure the DNA, the protocol used, the amount of DNA used, the integrity of the DNA used, the operator, and the freshness of the reagents, just to name a few. One way to increase the accuracy of the measurements is to use informatics based techniques to infer the correct genetic state of the DNA in the target based on the knowledge of the genetic state of related individuals. Since related individuals are expected to share certain aspect of their genetic state, when the genetic data from a plurality of related individuals is considered together, it is possible to identify likely errors and omissions in the measurements, and increase the accuracy of the knowledge of the genetic states of all the related individuals. In addition, a confidence may be computed for each call made.

For the purposes of this disclosure, a computer readable medium is a medium that stores computer data in machine readable form. By way of example, and not limitation, a computer readable medium can comprise computer storage media as well as communication media, methods or signals. Computer storage media, also called computer memory, includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology; CD-ROM, DVD, or other optical storage; cassettes, tape, disk, or other magnetic storage devices; or any other medium which can be used to tangibly store the desired information and which can be accessed by the computer.

Various implementations of the systems and techniques described here can be realized in digital electronic circuitry, integrated circuitry, specially designed ASICs (application-specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications or code) may include machine instructions for a programmable processor, and may be implemented in any form of programming language, including high-level procedural and/or object-oriented programming languages, and/or in assembly/machine languages. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Definitions

SNP (Single Nucleotide Polymorphism) refers to a single nucleotide that may differ between the genomes of two members of the same species. The usage of the term should not imply any limit on the frequency with which each variant occurs. The term SNP may include other allelic variations that occur over a number of nucleotides.

To call a SNP refers to the act of making a decision about the true state of a particular base pair, taking into account the direct and indirect evidence.

Sequence refers to a DNA sequence or a genetic sequence. It may refer to the primary, physical structure of the DNA molecule or strand in an individual.

Allele refers to the genes that occupy a particular locus.

To call an allele refers to the act of determining the genetic state at a particular locus of DNA. This may involve calling a SNP, a plurality of SNPs, or determining whether or not an insertion or deletion is present at that locus, or determining the number of insertions that may be present at that locus, or determining whether some other genetic variant, such as a single tandem repeats (STRs), or how many of that variant, are present at that locus.

Locus refers to a specific location of a gene or DNA sequence on a chromosome.

Ploidy calling, also 'chromosome copy number calling,' 'copy number calling,' 'ploidy state determination,' or 'copy number determination,' is the act of determining the quantity and possibly also the chromosomal identity of one or more chromosomes present in a cell.

Calling a hypothesis, refers to determining which hypothesis has the greatest likelihood of being true. The act of calling may be that point at which a decision is made about which hypothesis will be outputted as the call.

Confidence refers to the statistical likelihood that the called SNP, allele, set of alleles, or determined number of chromosomes copies or chromosome segment copies correctly represents the real genetic state of the individual.

Aneuploidy refers to the state where the wrong number of chromosomes are present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. When referring to a single autosomal chromosome, it may refer to the case where more or less than two homologous chromosomes are present. When referring to the sex chromosome, it may refer to the case there more or less than two of either X or Y chromosomes, or exactly two Y chromosomes, are present.

Ploidy State is the quantity and chromosomal identity of one or more chromosomes in a cell. It may refer to the total number and identity of each chromosome typically found in each cell of a given individual. It may refer to the number and identity of chromosome(s) for a particular chromosome number for a given individual.

Chromosomal identity refers to the referent chromosome number. Normal humans have 22 types of numbered autosomal chromosomes, and two types of sex chromosomes. It may also refer to the parental origin of the chromosome. It may also refer to a specific chromosome inherited from the parent, i.e. the chromosome that the parent inherited from his/her father, or the chromosome that the parent inherited from his/her mother. It may also refer to other identifying features of a chromosome. The identity of a chromosome may refer to the actual identity of a particular chromosome, or the identities of the chromosomes of a particular chromosome number, in each cell of a particular individual. For example, the chromosomal identity could be: 'chromosome 21' or it refer to a particular chromosome 21 with a particular genetic state, that is, for example, 'inherited from the mother, and homologous but not identical to two other chromosome 21s found in a particular female with Down syndrome.'

Chromosomal number refers to the cardinal number commonly assigned to a given chromosome, of which humans have 22 pairs of autosomal chromosomes and one pair of sex chromosomes, for a total of 23. The chromosome number may be a number from 1 to 23, and in the case of chromosome 23, it may be referred to as X or Y. It may refer to a class of chromosomes, for example, a child with Down syndrome may be found to have three chromosome 21s.

The State of the Genetic Material or simply 'genetic state' refers to the actual identity of a set of SNPs on the DNA, it may refer to the phased haplotypes of the genetic material, and it may refer to the sequence of the DNA, including insertions, deletions, repeats and mutations in an individual. It may also refer to the actual ploidy state of one or more chromosomes, chromosomal segments, or set of chromosomal segments in an individual.

Genetic abnormality refers to a genetic state that is highly correlated with a phenotypic abnormality. Aneuploidy is an example of a genetic abnormality. A genetic state that results in the death of a fetus or young child is a phenotypic abnormality.

Genotypic measurements, (or 'genetic measurements') a type of genotypic data, such as numerical, digital, pictorial or figurative representations of genotypic data that are obtained by using a genotyping technique to ascertain certain base pair sequences and/or identities, qualities or other characteristics of genetic material, chiefly, DNA. Genetic measurements may contain errors or omissions.

Genetic Data refers to data that describes a genetic state. The genetic data may take the form of genetic measurements, it may be encoded in an analog or digital fashion, it may be encoded on a computer, or it may take the form of a physical molecular genetic sequence.

Measuring genetic material refers to the act of transforming genetic data from a physical manifestation, for example, a specific base pair sequence, into a figurative representation of the genetic data, for example the representation of the genetic sequence stored digitally on a computer.

Mosaicism refers to a set of cells in an embryo, or other individual that are heterogeneous with respect to their ploidy state.

Homologous Chromosomes are chromosomes that contain the same set of genes that may normally pair up during meiosis.

Identical Chromosomes are chromosomes that contain the same set of genes, and for each gene they have the same set of alleles that are identical, or nearly identical.

Allele Drop Out or 'ADO' refers to the situation where one of the base pairs in a set of base pairs from homologous chromosomes at a given allele is not detected. ADO may refer to LDO.

Locus Drop Out or 'LDO' refers to the situation where both base pairs in a set of base pairs from homologous chromosomes at a given allele are not detected.

Homozygous refers to having similar alleles or SNPs at corresponding chromosomal loci.

Heterozygous refers to having dissimilar alleles or SNPs at corresponding chromosomal loci.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or also a segment or section of a chromosome.

Copies refer to the number of copies of a chromosome segment and may refer to identical copies, or it may refer to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype is a combination of alleles at multiple loci that are transmitted together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated. A haplotype may also be referred to as a 'strand', referring go to the fact that haplotypes are physically connected on one strand of DNA.

Haplotypic Data also called 'phased data' or 'ordered genetic data;' refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where the haplotype been determined.

Genetic data 'in', 'of', 'at', 'from' or 'on' an individual, (also 'genotypic data') refers to the data describing aspects of the genome of an individual. It may refer to one or a set of loci, partial or entire sequences, partial or entire chromosomes, or the entire genome.

Hypothesis refers to a set of possible ploidy states at a given set of chromosomes, or a set of possible allelic states at a given set of loci. The set of possibilities may contain one or more elements.

Copy number hypothesis, also 'ploidy state hypothesis,' refers to a hypothesis concerning how many copies of a particular chromosome are in an individual on per cell basis. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Target Individual refers to the individual whose genetic state is being determined. In one context, only a limited amount of DNA is available from the target individual. In one context, the target individual is a fetus. In some embodiments, there may be more than one target individual. In some embodiments, each child, embryo, fetus or sperm that originated from a pair of parents may be considered target individuals.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling or a grandparent.

Parent refers to the genetic mother or father of an individual. An individual will typically have exactly two parents, one mother and one father. A parent may be considered to be an individual.

Parental context, (also 'context'), refers to the genetic state of a given SNP, on each of the two relevant homologous chromosomes for each of the two parents of the target.

Isolation refers to a physical separation of the target genetic material from other contaminating genetic material or biological material. It may also refer to a partial isolation, where the target of isolation is separated from some or most, but not all of the contaminating material. For example, isolating fetal DNA may refer to isolating a fraction of fetal DNA that is preferentially enriched in fetal DNA as compared to the original sample.

Clinical Decision refers to any decision to take an action, or not to take an action, that has an outcome that affects the health or survival of an individual. In the context of prenatal diagnosis, a clinical decision may refer to a decision to abort or not abort a fetus. A clinical decision may refer to a decision to conduct further testing, or to take mitigating actions.

Platform response refers to the mathematical characterization of the input/output characteristics of a genetic measurement platform, and may be used as a measure of the statistically predictable measurement differences.

Informatics based method refers to a method designed to determine the ploidy state at one or more chromosomes or the allelic state at one or more alleles by statistically inferring the most likely state, rather than by directly physically measuring the state. In one embodiment of the present disclosure, the informatics based technique may be one disclosed in this patent. In one embodiment of the present disclosure it may be PARENTAL SUPPORT™.

Channel Intensity refers to the strength of the fluorescent or other signal associated with a given allele, base pair or other genetic marker that is output from a method that is used to measure genetic data. It may refer to a set of outputs from a device for measuring DNA. In one embodiment, it may refer to the set of outputs from a genotyping array.

Parental Context

The parental context refers to the genetic state of a given SNP, on each of the two relevant chromosomes for each of the two parents of the target. Note that in one embodiment, the parental context does not refer to the allelic state of the target, rather, it refers to the allelic state of the parents. The parental context for a given SNP may consist of four base pairs, two paternal and two maternal; they may be the same or different from one another. In this disclosure, it may be written as "$m_1 m_2 | f_1 f_2$", where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1 f_2 | m_1 m_2$". Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given allele, the mother's genotype was T on one chromosome, and G on the homologous chromosome, and the father's genotype at that allele is G on both of the homologous chromosomes, one may say that the target individual's allele has the parental context of AB|BB; in some contexts, it may be equally correct to say that the target individual's allele has the parental context of AB|AA, or BA|AA. Note that, in theory, any of the four possible alleles could occur at a given allele, and thus it is possible, for example, for the mother to have a genotype of AT, and the father to have a genotype of GC at a given allele. However, empirical data indicate that in most cases only two of the four possible base pairs are observed at a given allele. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous at the SNP, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. It is also possible for the genetic data from one parent to be phased, while the genetic data from the other parent to be unphased, in which case there would be twelve parental contexts. Every SNP allele on a chromosome, excluding some SNPs on the sex chromosomes, has one of these parental contexts. Note that some of these contexts may behave the same was other contexts, and one could lump those context together; this could be functionally equivalent to using the full number of contexts. Alternately, one could choose to ignore certain contexts for the purposes of analysis.

Once the parental contexts have been determined, the SNPs from each parental context may be grouped together, such that the SNP measurements from the target genetic sample may be treated statistically, as a group, and compared with expected behavior for various hypotheses. Grouping the SNPs by context simply refers to creating subsets of SNPs that are differentiated by parental context, where each subset may be treated in a bulk manner. Grouping the SNPs is beneficial because the expected bulk behavior of a set of SNPs depends its parental context.

The concept of parental contexts may be useful in the context of copy ploidy determination. When genotyped, the SNPs within a first parental context may be expected to statistically behave similarly when measured for a given ploidy state. In contrast, some sets of SNPs from a second parental context may be expected to statistically behave differently from those in the first parental context in certain circumstances, such as for certain ploidy states, and the difference in behavior may be characteristic of one or a set of particular ploidy states. There are many statistical techniques that could be used to analyze the measured responses at the various loci within the various parental contexts.

Hypotheses

A hypothesis may refer to a possible genetic state. It may refer to a possible ploidy state. A set of hypotheses refers to a set of possible genetic states. In some embodiments, a set of hypotheses may be designed such that one hypothesis from the set will correspond to the actual genetic state of any given individual. In some embodiments, a set of hypotheses may be designed such that every reasonably possible genetic state may be described by at least one hypothesis from the set. In some embodiments of the present disclosure, one aspect of the method is to determine which hypothesis corresponds to the actual genetic state of the individual in question.

In an embodiment of the present disclosure, one step involves creating a hypothesis. In some embodiments it may be a copy number hypothesis. In some embodiments it may involve a hypothesis concerning which segments of a chromosome from each of the related individuals correspond genetically to which segments, if any, of the other related individuals. Creating a hypothesis may refer to the act of setting the limits of the parameters such that the entire set of possible genetic states that are under consideration are encompassed by those parameters. Creating a hypothesis may refer to the act of setting the limits of the parameters such that a limited set of possible genetic states that are under consideration are encompassed by those parameters. Creating a set of hypotheses may refer to estimating and/or describing the statistically expected bounds of measured values that correspond to each of the hypotheses. Creating a set of hypotheses may refer to a knowledgeable person listing those possible ploidy states that may be reasonably likely under the circumstances. In one embodiment, it may refer to estimating the profile of SNP measurements of a target individual as measured on a high throughput SNP array for a set of parental contexts.

A 'copy number hypothesis', also called a 'ploidy hypothesis', or a 'ploidy state hypothesis', may refer to a hypothesis concerning a possible ploidy state for a given chromosome, or section of a chromosome, in the target individual. It may also refer to the ploidy state at more than one of the chromosomes in the individual. A set of copy number hypotheses may refer to a set of hypotheses where each hypothesis corresponds to a different possible ploidy state in an individual over one chromosome, or it may refer to a combination of single-chromosome hypotheses over more than one chromosomes, where the number of different chromosomes could vary, in humans, from 2 to 23. A normal individual contains one of each chromosome from each parent. However, due to errors in meiosis and mitosis, it is possible for an individual to have 0, 1, 2, or more of a given chromosome from each parent. In practice, it is rare to see more that two of a given chromosomes from a parent. In this disclosure, the embodiments only consider the possible hypotheses where 0, 1, or 2 copies of a given chromosome come from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2), and these may also be written H00, H01, H02, H10, H11, H12, H20, H21, H22. The different hypotheses correspond to different ploidy states. For example, (1,1) refers to a normal disomic chromosome; (2,1) refers to a maternal trisomy, and (0,1) refers to a monosomy. In some embodiments, the hypothesis may be written as $(m, f_x, f_y)$, to take into account the sex chromosome, where $f_x$ refers to an X-chromosome or autosomal chromosome inherited from the father, and $f_y$ refers to a Y-chromosome inherited from the father. When this notation is used for autosomal chromosomes the $f_y$ may simply act as a placeholder. Thus a euploid embryo that is H101 at chromosome 23 would be a male, and if it were H110 at chromosome 23, it would be a female. For example, H000 represents the nullsomy hypothesis; H100, H010 and H001 represent the monosomy hypotheses; H110 and H101 represent the normal disomy hypotheses; H200, H020, H002, and H011 represent uniparental disomy hypotheses; and H210, H120, and H111 represent the trisomy hypotheses; and H220, H211, and H202 represent some of the possible tetrasomy hypotheses.

In some embodiments, the trisomy case, where two chromosomes are inherited from one parent and one chromosome is inherited from the other parent may be further differentiated into two cases: one where the two chromosomes are identical (matched copy error), and one where the two chromosomes are homologous but not identical (unmatched copy error).

In some embodiments, where the parental data is phased, and thus each allele may be specified as being part of either of two haplotypes, there are sixteen possible hypotheses. In an embodiment where only one parent is phased, there may be twelve hypotheses. It is possible to use other sets of hypotheses. In an embodiment, some hypotheses that are considered to be unlikely may be discounted.

In some embodiments of the present disclosure, the ploidy hypothesis may refer to a hypothesis concerning which chromosome from other related individuals correspond to a chromosome found in the target individual's genome. In some embodiments, the method uses the knowledge that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

Once the set of hypotheses have been defined, when the algorithms operate on the input genetic data, they may output a determined statistical probability for each of the hypotheses under consideration. The probabilities of the various hypotheses may be determined by mathematically calculating, for each of the various hypotheses, the value of the probability, as stated by one or more of the expert techniques, algorithms, and/or methods described elsewhere in this disclosure, related disclosures, and/or encompassed by the PARENTAL SUPPORT™ technique, using the relevant genetic data as input. The calculation may produce an exact value, it may give an estimate, it may include an error term, it may include a confidence, and it may represent a statistical likelihood.

Once the probabilities of the different hypotheses are calculated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

In some embodiments, if the probability for a given hypothesis is greater than the probability for any of the other hypotheses, then that hypothesis may be determined to be the most likely. In some embodiments, a hypothesis may be determined to be the most likely, and the ploidy state, or other genetic state, may be called if the normalized probability is greater than a threshold. In one embodiment, this may mean that the number and identity of the chromosomes that are associated with that hypothesis may be called as the ploidy state. In one embodiment, this may mean that the identity of the alleles that are associated with that hypothesis may be called as the allelic state, and/or the genetic state. In some embodiments, the threshold may be between about 50% and about 80%. In some embodiments the threshold may be between about 80% and about 90%. In some embodiments the threshold may be between about 90% and about 95%. In some embodiments the threshold may be between about 95% and about 99%. In some embodiments the threshold may be between about 99% and about 99.9%. In some embodiments the threshold may be above about 99.9%.

Parental Support

Some embodiments of the disclosed invention may be used in combination with the PARENTAL SUPPORT™ (PS) method, other embodiments of which are described in three patent applications: Rabinowitz 2006, 2008 and 2009. In some embodiments, the methods disclosed herein may be considered as part of the PARENTAL SUPPORT™ method. In some embodiments, The PARENTAL SUPPORT™ method is a collection of methods that may be used to determine the genetic data, with high accuracy, of one or a small number of cells, specifically to determine disease-related alleles, other alleles of interest, and/or the ploidy state of one or more chromosomes on the cell(s). PARENTAL SUPPORT™ may refer to any of these methods. PARENTAL SUPPORT™ is an example of an informatics based method.

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possibly of one or more related individuals, in order to reconstruct, in silico, on a computer, the genotype at a plurality of alleles, and/or the ploidy state of an embryo or of any target cell(s), and the target DNA at the location of key loci with a high degree of confidence. The PARENTAL SUPPORT™ method can reconstruct not only single-nucleotide polymorphisms that were measured poorly, but also insertions and deletions, and SNPs or whole regions of DNA that were not measured at all. Furthermore, the PARENTAL SUPPORT™ method can both measure multiple disease-linked loci as well as screen for aneuploidy, from a single cell, or from the same small amount of DNA. In some embodiments, the PARENTAL SUPPORT™ method may be used to characterize one or more cells from embryos biopsied during an IVF cycle to determine the genetic condition of the one or more cells. In some embodiments, the PARENTAL SUPPORT™ method may be used to determine the ploidy state of a fetus from free floating fetal DNA and/or fetal cells that may be found in maternal blood, or from some other source.

In an embodiment, the PARENTAL SUPPORT™ method allows the cleaning of noisy genetic data. This may be done by inferring the correct genetic alleles in the target genome (embryo or fetus) using the genotype of related individuals (parents) as a reference. PARENTAL SUPPORT™ may be particularly relevant where only a small quantity of genetic material is available (e.g. PGD or NIPGD) and where direct measurements of the genotypes are inherently noisy due to the limited amounts of genetic material. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

One aspect of the PARENTAL SUPPORT™ technology is a chromosome copy number calling algorithm that in some embodiments uses parental genotype contexts. To call the chromosome copy number, the algorithm may use the phenomenon of locus dropout (LDO) combined with distributions of expected embryonic genotypes. During whole genome amplification, LDO necessarily occurs. LDO rate is concordant with the copy number of the genetic material from which it is derived, i.e., fewer chromosome copies result in higher LDO, and vice versa. As such, it follows that loci with certain contexts of parental genotypes behave in a characteristic fashion in the embryo, related to the probability of allelic contributions to the embryo. For example, if both parents have homozygous BB states, then the embryo should never have AB or AA states. In this case, measurements on the A detection channel are expected to have a distribution determined by background noise and various interference signals, but no valid genotypes. Conversely, if both parents have homozygous AA states, then the embryo should never have AB or BB states, and measurements on the A channel are expected to have the maximum intensity possible given the rate of LDO in a particular whole genome amplification reaction. When the underlying copy number state of the embryo differs from disomy, loci corresponding to the specific parental contexts behave in a predictable fashion, based on the additional allelic content that is contributed by, or is missing from, one of the parents. This allows the ploidy state at each chromosome, or chromosome segment, to be determined. The details of embodiments of this method are described elsewhere in this disclosure.

Platform Response

There are many methods that may be used to measure genetic data. None of the methods currently known in the art are able to measure the genetic data with 100% accuracy; rather there are always errors, and/or statistical bias, in the data. It may be expected that the method of measurement will introduce certain statistically predictable biases into the measurement. It may be expected that certain sets of DNA, amplified by certain methods, and measured with certain techniques may result in measurements that are qualitatively and quantitatively different from other sets of DNA, that are amplified by other methods, and/or measured with different techniques. In some cases these errors may be due to the method of measurement. In some cases this error may be due to the state of the DNA. In some cases this bias may be due to the tendency of some types of DNA to respond differently to a given genetic measurement method. In some cases, the measurements may differ in ways that correlate with the number of cells used. In some cases, the measurements may differ based on the measurement technique, for example, which sequencing technique or array genotyping technique is used. In some cases different chromosomes may amplify to different extents. In some cases, certain alleles may be more or less likely to amplify. In some cases, the error, bias, or differential response may be due to a combination of factors. In many or all of these cases, the statistical predictability of these measurement differences, termed the 'platform response', may be used to correct for these factors, and can result in data for which the accuracy is maximized, and where each measurement is associated with an appropriate confidence.

The platform response may be described as a mathematical characterization of the input/output characteristics of a genetic measurement platform, such as TAQMAN, the AFFYMETRIX GENECHIP or the ILLUMINA INFINIUM BEADARRAY. The platform response may be specific to a particular platform, to a particular model of genotyping machine, to a particular genotyping machine, or even to a particular scientist using a particular genotyping machine. The input to the channel is the amplified genetic material with any annealed, fluorescently tagged genetic material. The channel output could be allele calls (qualitative) or raw numerical measurements (quantitative), depending on the context. For example, in the case in which the platform's raw numeric output is reduced to qualitative genotype calls, the platform response may consist of an error transition matrix that describes the conditional probability of seeing a particular output genotype call given a particular true genotype input. In one embodiment, in which the platform's output is left as raw numeric measurements, the platform response may be a conditional probability density function that describes the probability of the numerical outputs given a particular true genotype input.

In some embodiments of the present disclosure, the knowledge of the platform response may be used to statistically correct for the bias. In some embodiments of the present disclosure, the knowledge of the platform response may be used to increase the accuracy of the genetic data. This may be done by performing a statistical operation on the data that acts in the opposite manner as the biasing tendency of the measuring process. It may involve attaching the appropriate confidence to a given datum, such that when combined with other data, the hypothesis found to be most likely is indeed most likely to correspond to the actual genetic state of the individual in question.

In some embodiments of the present disclosure, a statistical method may be used to remove the bias in the data due to the tendency for certain maternal or paternal alleles to amplify in a disproportionate manner to the other alleles. In some embodiments of the present disclosure, a statistical method may be used to remove the bias in the data due to the tendency for certain probes to amplify certain SNPs in a manner that is disproportionate to other SNPs.

Imagine the two dimensional space where the x-coordinate is the x channel intensity and the y-coordinate is the y channel intensity. In this space, one may expect that the context means should fall on the line defined by the means for contexts BB|BB and AA|AA. In some cases, it may be observed that the average contexts means do not fall on this line, but are biased in a statistical manner; this may be termed "off line bias". In some embodiments of the present disclosure, a statistical method may be used to correct for the off line bias in the data.

In some cases splayed dots on the context means plot could be caused by translocation. If a translocation occurs, then one may expect to see abnormalities on the endpoints of the chromosome only. Therefore, if the chromosome is broken up into segments, and the context mean plots of each segment are plotted, then those segments that lie on the of a translocation may be expected to respond like a true trisomy or monosomy, while the remaining segments look disomic. In some embodiments of the present disclosure, a statistical method may be used to determine if translocation has occurred on a given chromosome by looking at the context means of different segments of the chromosome.

Ploidy Determination when Genetic Material of the Target Individual is Contaminated In an embodiment of the method, it is possible to determine the ploidy state of a fetus in a non-invasive manner by measuring fetal DNA contained in maternal blood. Note that this may be complicated considerably by the fact that the amount of fetal DNA available in maternal blood may be small. The amount of fetal free floating DNA found in serum is typically less than 50%, and often less than 20%, and the background maternal free floating DNA makes measurements on the fetal DNA very noisy and difficult to interpret. The number of fetal cells in maternal blood is often less than 1 cell in 100,000, and can be as low as 1 cell in a million, or lower. This method overcomes the difficulties described here, as well as other difficulties known in the art. The method may be applicable in cases where the amount of target DNA is in any proportion with the non-target DNA; for example, the target DNA could make up anywhere between 0.01% and 99.99% of the DNA present.

The first step of the method is to make genomic measurements on the mother and optionally the father, such that the diploid genetic data is known at a large number of alleles for one or both parents. The number of alleles may range from 100 to 100,000,000. In an embodiment, the number of alleles ranges from 500 to 100,000 per chromosome targeted. In an embodiment, the number of alleles ranges from 1,000 to 20,000 per chromosome targeted. In an embodiment of the invention, the alleles are SNPs known to be polymorphic in the human population. Once the parental genotypes are known at a set of SNPs, the SNPs may be subdivided into a number of sets of SNPs where each set corresponds to the set of SNPs in a particular parental context.

One may next determine the platform response of the system using the genetic measurements of certain contexts. One also may determine the ratio of target DNA to maternal DNA in the sample, using the genetic measurements of certain contexts. One also may also determine the observed ADO given the observed genetic measurements.

The next step is to create a number of hypotheses, one for each hypothetical ploidy state of interest on a chromosome of interest, and determine the expected statistical distribution of genotypic measurements for that hypothetical child, given expected ADO rates, and given the expected platform response. For example, at chromosome 21, several hypothetical child genotypes may be envisioned, for example, one for a child that is disomic at chromosome 21 (H110), and a one for a child that has maternal trisomy at chromosome 21 (H210). Note that for autosomal chromosomes, (Hαβγ) denotes the hypothesis where α copies of a maternally derived chromosome are present, β copies of a paternally derived chromosome are present, and γ is placeholder set to 0; in the case of the sex chromosome, (Hαβγ) denotes the hypothesis where α copies of a maternally derived chromosome are present, β indicates the number of paternally derived X chromosomes that are present, and γ indicates the number of paternally derived Y chromosomes that are present.

Note that the hypothetical genotypes are not necessarily SNP-by-SNP genotypes, rather they may be expected statistical distributions of SNPs within a given parental context. For example, imagine looking only at the parental context AA|AB, meaning the set of SNPs from the target individual where the mother is homozygous and the father is heterozygous. The H110 child is expected to have an equal chance of a SNP being AA or AB within that parental context, and thus, one would expect to see, approximately, a 3:1 A:B ratio for the SNPs that are in the AA|AB parental context. The H210 child is expected to have an equal chance of being AAA or AAB within that parental context, and thus, one would expect to see approximately, a 5:1 A:B ratio for the SNPs that are in the AA|AB parental context. By observing the measured channel intensities for the various nucleotides it may be possible to determine which actual genetic state is most likely for that chromosome: disomy or trisomy.

Below is described certain aspects of an embodiment of the invention in more firm, mathematical terms. This section discusses how one can take the parental genetic measurements, and the genetic measurements from the mixed sample of fetal and maternal genetic material, in the form of output from the genotyping platform, and transform those measurements into a copy number call.

Variable Definitions y=the average measured intensity from SNPs in a given context on a particular chromosome, on a particular channel x=the statistically expected number of allele copies present per locus, for the channel being measured, for SNPs in the context.

$\Delta$=the fraction of fetal DNA in the sample n=the fraction of SNPs that are A for a given genotype v=a term denoting observational noise, which is a random variable with an unknown distribution.

One may state that $x \sim (1-\Delta)n_{mother} + \Delta n_{fetus}$, and also that $y=f(x)+v$, that is, the distribution of the measurements of a set of SNPs within a given parental context will be some function of the number of expected alleles in the sample and the platform response, plus a noise factor.

In one embodiment of the invention, f(x) may be assumed to be a second order polynomial, that is, $f(x) \sim f_1 x^2 + f_2 x + f_3$. In another embodiment, f(x) may be assumed to be a first order polynomial, that is, $f(x) \sim f_1 x + f_2$. In another embodiment, f(x) may be assumed to be an exponential equation, or other algebraic equation, or some combination thereof. Assume that v is Gaussian distributed with 0 mean, and a standard deviation=V.

It should be understood that f(x) could be assumed to be any number of functions such as a first order polynomial, a third order polynomial, any other polynomial, any exponential, or any other algebraic or other relationship between x and y. It should also be understood that v could be any number of distributions, including a Gaussian, a Rayleigh distribution, a Pearson distribution, or a Bernoulli distribution.

At this point, x is known in terms of $\Delta$ and n, and $f_1$, $f_2$, $f_3$, $\Delta$, and the distribution of v, parameterized by V, is unknown. For a given sample, a genotypic measurement, y, is made of the sample for a number of SNPs, for each context, for each channel, over a number of chromosomes, including the chromosome(s) of interest, whose ploidy state is to be determined, as well as at least one chromosome that may be expected to be disomic. Each set of y's are then combined into a vector. Note that the set of chromosomes whose ploidy state is to be determined and the at least one chromosome that may be expected to be disomic may overlap.

For example, in the human, there are a set of chromosomes that can result in a live birth even when aneuploid, most commonly, chromosome 13, 18, 21, X and Y. It is also known for live children to be born with aneuploidy at chromosomes 4, 5, 7, 8, 9, 11, 15, 16, 22. Note that other aneuploidy states, such as translocations and uniparental disomy, at any chromosome may give rise to born children with chromosomal abnormalities. One of the chromosomes which is infrequently found to be aneuploid in gestating fetuses with a heartbeat, such as 1, 2, or 3 may be used as a reference diploid chromosome. Alternately, one of the chromosomes that is targeted for aneuploidy testing may be used as a reference, since it is unlikely that more than one gross chromosomal abnormality exists in a gestating fetus. In one embodiment of the invention, the chromosomes targeted for aneuploidy detection include 13, 18, 21, X and Y.

Given the measured y, or $y_m$, for the chromosome that is expected to be disomic, and given the expected number of A's measured in the sample, $x_{(H110)}$, one may then find a maximum likelihood estimate for $f_1$, $f_2$, $f_3$, v and $\Delta$. The maximum likelihood estimate may be performed using a non-linear gradient descent method. Once $f_1$, $f_2$, $f_3$, v and A have been estimated, distributions may be made for the predicted value of y, $y_p$, for the various ploidy state hypotheses, for example $y_{predicted(H110)}$ and $y_{predicted(H210)}$.

The observed $y_m$ can be compared against the distributions for $y_p$ and the likelihood of each hypothesis can be determined, which is the probability of observing $y_m$ according to the predicted model. The hypothesis with the highest likelihood corresponds to the most likely ploidy state of the fetus. A confidence in the ploidy call may be calculated from the different likelihoods of the various hypotheses.

For a particular chromosome, assume that the likelihoods $p(y_m|H110)$, $p(y_m|H210)$ and $p(y_m|H120)$ have been calculated. Also assume that the prior probability of each hypothesis is known from statistical population study. For example, p(H110) is the overall probability of disomy on this chromosome for the population of interest. If $p(y_m|H110)$ is the highest likelihood, then the confidence on disomy is calculated using Bayes rule as confidence=$p(y_m|H110)$ p(H110)/ $(p(y_m|H110)$ p(H110)+$p(y_m|H210)$ p(H210)+$p(y_m|H120)$ p(H120)).

Overview of the Method

In an embodiment, the present disclosure presents a method by which one may determine the ploidy state of a gestating fetus, at one or more chromosome, in a non-invasive manner, using genetic information determined from fetal DNA found in maternal blood, and genetic data from the mother and the father. The fetal DNA may be purified, partially purified, or not purified; genetic measurements may be made on DNA that originated from more than one individual. Informatics type methods can infer genetic information of the target individual, such as the ploidy state, from the bulk genotypic measurements at a set of alleles. The set of alleles may contain various subsets of alleles, wherein one or more subsets may correspond to alleles that are found on the target individual but not found on the non-target individuals, and one or more other subsets may correspond to alleles that are found on the non-target individual and are not found on the target individual. The set of alleles may also contain subsets of alleles where the allele is found on the target and the non-target in differing expected ratios. The method may involve comparing ratios of measured output intensities for various subsets of alleles to expected ratios given various potential ploidy states. The platform response may be determined, and a correction for the bias of the system may be incorporated into the method. The ploidy determination may be made with a computed confidence. The ploidy determination may be linked to a clinical action. That clinical action may be to terminate or not terminate a pregnancy. An embodiment of the invention involves the case where the target individual is a fetus, and the non-target individual is the biological mother of the fetus.

In a basic explanation, the method works as follows. A simple version of idea is to attempt to quantify the amount of fetal DNA at SNPs where the fetus has an allele that the mother does not. First, the genotypic data of the parents are measured using a method that produces data for a set of SNPs. Then the SNPs are sorted into parental contexts. The SNPs found in contexts where the mother is heterozygous, AB, are considered to be less informative, since the contaminating DNA in maternal blood will have a large amount of both alleles. The SNPs found in contexts where the mother and father have the same set of alleles are also considered to be less informative, since the background and the fetal signal are the same. The simple method focuses on the contexts where the father has an allele that the mother does not, for example: AA|AB and AA|BB (and BB|AB and BB|BB, though these are the same, by symmetry.) In the case of the AA|BB context, the fetus is expected to be AB, and therefore the B allele should appear in fetal DNA. In the case of the AA|AB context, the fetus is expected to be AA half the time, and AB half the time, meaning the B allele should appear in fetal DNA half the time.

Once the appropriate contexts have been selected, and the SNPs have been grouped by parental context, for example, the mother AA contexts, then the appropriate SNPs are identified where the B SNP has been measured, indicating that the fetus is AB, along with the quantities of DNA measured for each of those SNPs. Now the intensities of the measurements of the SNPs for a chromosome assumed to be disomic are compared to the intensities of the measurements of the SNPs for the chromosome of interest are compared, adjusted appropriately for platform response. If the intensities of the SNPs for each of the two chromosomes are about equal, then the chromosome of interest is considered to be disomic, and if the intensities on the chromosome is about 50% greater than the intensities on the assumed disomic chromosome, then the chromosome of interest is considered to be paternal trisomic.

Note that this is a basic explanation of a simple version of the method. In an embodiment, some or all of the contexts may be used, including those of greater and lesser informativeness. In an embodiment, some or all of the SNPs may be used. For those contexts and SNPs that are more informative, for example, the SNPs in the AA|BB context, the measurements may have greater weight in the overall calculation. For those contexts and SNPs that are less informative, for example, the SNPs in the AA|AA context, the measurements may have lesser weight in the overall calculation. The explanation above focuses on measuring the number of paternal chromosomes. A similar method may be used to determine the number of maternal chromosomes, with appropriate adjustments made. For example, the expected ratios of SNP intensities for the disomy and trisomy hypothesis will be different, because the background maternal genotypic data and the fetal genotypic data will be similar or identical. For example, in a case where the mixed sample contains 20% fetal DNA and 80% maternal DNA, looking at the AA|BB context, for a disomy, one would expect a ratio of 90:10 for the A:B measurements (80% A plus 20% 1:1 A:B), for a maternal trisomy one would expect a ratio closer to 93.3:6.7 (80% A plus 20% 2:1 A:B), and for a paternal trisomy one would expect a ratio closer to 86.7:13.3 (80% A plus 20% 1:2 A:B).

Note that this method may be used equally well with more or less genotypic information from the parents. For example, if the father's genotype is unknown, the method may consider all contexts where the mother is homozygous (AA) to be more informative, and the chance of the fetus having a B SNPs may be calculated roughly from known SNP heterozygosities in the population. At the same time, if the father's genotype is phased, that is, the haplotypes are known, copy number accuracies may be increased, since there will be strong correlations between expected contexts. For example, imagine three correlated SNPs on a chromosome where the contexts are AA|AB, AA|BA, AA|AB (the father is phased.) If the B allele is detected in maternal blood for the first SNP, there is a much higher probability of detecting a B for the third allele, as opposed to the second allele, since a euploid fetus inherits only one haplotype from each parent. At the same time, if the mother's genotype is phased, accuracies are similarly increased, since there will be more expected correlations between expected fetal contributions to the relative SNP intensities.

Using each of the parent contexts, and chromosomes known to be euploid, it is possible to estimate, by a set of simultaneous equations, the amount of DNA in the maternal blood from the mother and the amount of DNA in the maternal blood from the fetus. These simultaneous equations are made possible by the knowledge of the alleles present on the mother, and optionally, the father. In an embodiment, the genetic data from both the mother and the father is used. In particular, alleles present on the father and not present on the mother provide a direct measurement of fetal DNA. One may then look at the particular chromosomes of interest, such as chromosome 21, and see whether the measurements on this chromosome under each parental context are consistent with a particular hypothesis, such as $H_{mp}$ where m represents the number of maternal chromosomes and p represents the number of paternal chromosomes e.g. $H_{11}$ representing euploid, or $H_{21}$ and $H_{12}$ representing maternal and paternal trisomy respectively.

In some embodiments of the invention the method may be employed with knowledge of the maternal genotype, and without knowledge of the paternal genotype. In this case, one could infer father contexts by looking at the SNP data for those measurements on the mixed sample that cannot be explained by mother data. One would begin identify the SNPs where mother is homozygous (AA), and then look at the SNP data from the mixed sample for B alleles. For those SNPs it is possible to infer that the father was AB or BB, and the fetus is AB. Likewise, for SNPs where the mother is AA, and no B was measured in the mixed sample, it is possible to infer that the fetus is AA with a certain probability, where the probability is correlated to the ADO and LDO rates. It is also possible to use parental data with a certain degree of uncertainty attached to the measurements. The methods described herein can be adapted to determine the ploidy state of the fetus given greater or lesser amounts of genetic information from the parents.

Some Assumptions

Note that these assumptions do not need to be true for this method to function as intended, rather they represent the idealized case for which this derivation is designed.

The expected amount of genetic material in the maternal blood from the mother is constant across all loci.

The expected amount of genetic material present in the maternal blood from the fetus is constant across all loci assuming the chromosomes are euploid.

The chromosomes that are non-viable (excluding 13, 18, 21, X, Y) are all euploid in the fetus. In one embodiment, only some of the non-viable chromosomes on the fetus need be euploid.

General Problem Formulation:

One may write $y_{ijk}=g_{ijk}(x_{ijk})+v_{ijk}$ where $x_{ijk}$ is the quantity of DNA on the allele k=1 or 2 (1 represents allele A and 2 represents allele B), j=1 . . . 23 denotes chromosome number and i=1 . . . N denotes the locus number on the chromosome, $g_{ijk}$ is platform response for particular locus and allele ijk, and $v_{ijk}$ is independent noise on the measurement for that locus and allele. The amount of genetic material is given by $x_{ijk}=am_{ijk}+\Delta c_{ijk}$ where a is the amplification factor (or net effect of leakage, diffusion, amplification etc.) of the genetic material present on each of the maternal chromosomes, $m_{ijk}$ (either 0,1,2) is the copy number of the particular allele on the maternal chromosomes, $\Delta$ is the amplification factor of the genetic material present on each of the child chromosomes, and $c_{ijk}$ is the copy number (either 0,1,2,3) of the particular allele on the child chromosomes. Note that for the first simplified explanation, a and $\Delta$ are assumed to be independent of locus and allele i.e. independent of i, j, and k. Thus it can be stated:

$$y_{ijk}=g_{ijk}(am_{ijk}+\Delta c_{ijk})+v_{ijk}.$$

Approach Using an Affine Model that is Uniform Across all Loci:

One may model g with an affine model, and for simplicity assume that the model is the same for each locus and allele, although it will be obvious after reading this disclosure how to modify the approach when the affine model is dependent on i,j,k. Assume the platform response model is $$g_{ijk}(x_{ijk})=b+am_{ijk}+\Delta c_{ijk}$$

where the amplification factors a and $\Delta$ are used without loss of generality, and a y-axis intercept b is added which defines the noise level when there is no genetic material. The goal is to estimate a and $\Delta$. It is also possible to estimate b independently, but in this section, the noise level is assumed to be roughly constant across loci, and only the set of equations based on parent contexts are used to estimate a and $\Delta$. The measurement at each locus is given by $$y_{ijk}=b+am_{ijk}+\Delta c_{ijk}+v_{ijk}$$

Assuming that the noise $v_{ijk}$ is independent and identically distributed (i.i.d.) for each of the measurements within a particular parent context, T, one can sum the signals within that parent context. The parent contexts are represented in terms of alleles A and B, where the first two alleles represent the mother and the second two alleles represent the father: T∈{AA|BB, BB|AA, AB|AB, AA|AA, BB|BB, AA|AB, AB|AA, AB|BB, BB|AB}. For each context T, there is a set of loci i,j where the parent DNA conforms to that context, represented i,j∈T. Hence:

$$y_{T,k} = \frac{1}{N_T}\sum_{i,j\in T} y_{i,j,k} = b + a\overline{m_{k,T}} + \Delta\overline{c_{k,T}} + \overline{v_{k,T}}$$

Where $\overline{m_{k,T}}$, $\overline{c_{k,T}}$ and $\overline{v_{k,T}}$ represent the means of the respective values over all the loci conforming to the parent context T, or over all i, j∈T. The mean or expected values $\overline{c_{k,T}}$ will depend on the ploidy status of the child. The table below describes the mean or expected values $\overline{m_{k,T}}$ and $\overline{c_{k,T}}$ for k=1(allele A) or 2(allele B) and all the parent contexts T. The expected values are calculated assuming different hypotheses on the child, for example: euploidy and maternal trisomy. The hypotheses are denoted by the notation $H_{mf}$, where m refers to the number of chromosomes from the mother and f refers to the number of chromosomes from the father e.g. $H_{11}$ is euploid, $H_{21}$ is maternal trisomy. Note that there is symmetry between some of the states by switching A and B, but all states are included for clarity:

| Context | AA/BB | BB/AA | AB/AB | AA/AA | BB/BB | AA/AB | AB/AA | AB/BB | BB/AB |
|---|---|---|---|---|---|---|---|---|---|
| $\overline{m_{A,T}}$ | 2 | 0 | 1 | 2 | 0 | 2 | 1 | 1 | 0 |
| $\overline{m_{B,T}}$ | 0 | 2 | 1 | 0 | 2 | 0 | 1 | 1 | 2 |
| $\overline{c_{A,T}}|H_{11}$ | 1 | 1 | 1 | 2 | 0 | 1.5 | 1.5 | 0.5 | 0.5 |
| $\overline{c_{B,T}}|H_{11}$ | 1 | 1 | 1 | 0 | 2 | 0.5 | 0.5 | 1.5 | 1.5 |
| $\overline{c_{A,T}}|H_{21}$ | 2 | 1 | 1.5 | 3 | 0 | 2.5 | 2 | 1 | 0.5 |
| $\overline{c_{B,T}}|H_{21}$ | 1 | 2 | 1.5 | 0 | 3 | 0.5 | 1 | 2 | 2.5 |

This describes a set of equations describing all the expected values $y_{T,k}$, which may be cast in matrix form, as follows:

$$Y=B+A_H P+v$$

Where $$Y=[y_{AA|BB},y_{BB|AA},y_{AB|BB},y_{AA|AA},y_{BB|BB},y_{AA|AB},\\ 1y_{AB|AA},y_{AB|BB},y_{BB|AB},y_{AA|BB},2y_{BB|AA},2y_{AB|AB},\\ 2y_{AA|AA},2y_{BB|BB},2y_{AA|AB},2y_{AB|AA},2y_{AB|BB},2y_{BB|AB},\\ 2]^T$$

$$P = \begin{bmatrix} \alpha \\ \Delta \end{bmatrix}$$

is the matrix of parameters to estimate $B=b\vec{1}$ where $\vec{1}$ is the 18×1 matrix of ones
$v=[\overline{v_{A,AA|BB}} \ldots \overline{v_{B,BB|AB}}]^T$ is the 18×1 matrix of noise terms and $A_H$ is the matrix encapsulating the data in the table, where the values are different for each hypothesis H on the ploidy state of the child. Below are examples of the Matrix $A_H$ for the ploidy hypotheses $H_{11}$ and $H_{21}$ $$A_{H_{11}} = \begin{bmatrix} 2.0 & 1.0 \\ 0 & 1.0 \\ 1.0 & 1.0 \\ 2.0 & 2.0 \\ 0 & 0 \\ 2.0 & 1.5 \\ 1.0 & 1.5 \\ 1.0 & 0.5 \\ 0 & 0.5 \\ 0 & 1.0 \\ 2.0 & 1.0 \\ 1.0 & 1.0 \\ 0 & 0 \\ 2.0 & 2.0 \\ 0 & 0.5 \\ 1.0 & 0.5 \\ 1.0 & 1.5 \\ 2.0 & 1.5 \end{bmatrix} \quad A_{H_{21}} = \begin{bmatrix} 2.0 & 2.0 \\ 0 & 1.0 \\ 1.0 & 1.5 \\ 2.0 & 3.0 \\ 0 & 0 \\ 2.0 & 2.5 \\ 1.0 & 2.0 \\ 1.0 & 1.0 \\ 0 & 0.5 \\ 0 & 1.0 \\ 2.0 & 2.0 \\ 1.0 & 1.5 \\ 0 & 0 \\ 2.0 & 3.0 \\ 0 & 0.5 \\ 1.0 & 1.0 \\ 1.0 & 2.0 \\ 2.0 & 2.5 \end{bmatrix}$$

In order to estimate a and Δ, or matrix P, the data across all chromosomes that may be assumed to be euploidy on the child sample are aggregated. This would include some or all of the chromosomes j=1 . . . 23 that have been measured, except those that are uncertain and thus under test. In one embodiment, the uncertain chromosomes include j=13, 18, 21, X and Y. In one embodiment, one could also apply a concordance test for the results on the individual chromosomes in order to detect mosaic aneuploidy on the non-viable chromosomes. In order to clarify notation, define Y' as Y measured over all the euploid chromosomes, and Y'" as Y measured over a particular chromosome under test, such as chromosome 21, which may be aneuploid. Apply the matrix $A_{H_{11}}$ to the euploid data in order to estimate the parameters:

$$\hat{P}=\text{argmin}_P \|Y'-B-A_{H_{11}}P\|_2=(A_{H_{11}}{}^T A_{H_{11}})^{-1} A_{H_{11}}{}^T \tilde{Y}$$

where $\tilde{Y}=Y'-B$ i.e. the measured data with the bias removed. The least-squares solution above is only the maximum-likelihood solution if each of the terms in the noise matrix v has a similar variance. In some cases, this is not the case, most simply because the number of loci $N'_T$ used to compute the mean measurement for each context T may be different for each context. As above, $N_T'$ refers to the number of loci used on the chromosomes known to be euploid, and C' denotes the covariance matrix for mean measurements on the chromosomes known to be euploid. There are many approaches to estimating the covariance C' of the noise matrix v, which may be assumed to be distributed as v~N(0,C'). Given the covariance matrix, the maximum-likelihood estimate of P is $$\hat{P}=\text{argmin}_P\|C'^{-1/2}(Y'-B-A_{H_{11}}P)\|_2=(A_{H_{11}}{}^T C'^{-1} A_{H_{11}})^{-1} A_{H_{11}}{}^T C'^{-1}\tilde{Y}$$

One simple approach to estimating the covariance matrix is to assume that all the terms of v are independent (i.e. no off-diagonal terms) and invoke the Central Limit Theorem so that the variance of each term of v scales as $1/N'_T$ and then find the 18×18 matrix $$C' = \begin{bmatrix} 1/N'_{AA|BB} & \cdots & 0 \\ \vdots & \ddots & \vdots \\ 0 & \cdots & 1/N'_{BB|AB} \end{bmatrix}$$

Once P' has been estimated, these parameters are used to determine the most likely hypothesis on the chromosome under study, such as chromosome 21. In other words, the following hypothesis may be chosen:

$$H^*=\text{argmin}_H\|C''^{-1/2}(Y''-B-A_H\hat{P})\|_2$$

Having found H* one can then estimate the degree of confidence in the determination of H*. Assume, for example, that there are two hypotheses under consideration: $H_{11}$ (euploid) and $H_{21}$ (maternal trisomy). Assume that $H^*=H_{11}$. The distance measures corresponding to each of the hypotheses may be computed as follows:

$$d_{11}=\|C''^{-1/2}(Y''-B-A_{H_{11}}\hat{P})\|_2$$

$$d_{21}=\|C''^{-1/2}(Y''-B-A_{H_{21}}\hat{P})\|_2$$

It can be shown that the square of these distance measures are roughly distributed as a Chi-Squared random variable with 18 degrees of freedom. Let $\chi_{18}$ represent the corresponding probability density function for such a variable. One may then find the ratio in the probabilities $p_H$ of each of the hypotheses according to:

$$\frac{p_{H_{11}}}{p_{H_{21}}} = \frac{\chi_{18}(d_{11}^2)}{\chi_{18}(d_{21}^2)}$$

The probabilities of each hypothesis may be calculated by adding the equation $p_{H_{11}}+p_{H_{21}}=1$. The confidence that the chromosome is in fact euploid is given by $p_{H_{11}}$.

In some embodiments, it is possible to modify the above approach for different biases b on each of the channels representing alleles A and B. The bias matrix B is redefined as follows:

$$B = \begin{bmatrix} b_A \vec{1} \\ b_B \vec{1} \end{bmatrix}$$

where $\vec{1}$ is a 9×1 matrix of ones. As discussed above, the parameters $b_A$ and $b_B$ can either be assumed based on a-priori measurements, or can be included in the matrix P and actively estimated (i.e. there is sufficient rank in the equations over all the contexts to do so).

In one embodiment, in the general formulation, where $y_{ijk}=g_{ijk}(am_{ijk}+\Delta c_{ijk})+v_{ijk}$, one can directly measure or calibrate the function for every locus and allele, so that the function (which is monotonic for the vast majority of $g_{ijk}$ genotyping platforms) can be inverted. One can then use the function inverse to recast the measurements in terms of the quantity of genetic material so that the system of equations is linear i.e. $y'_{ijk}=g_{ijk}{}^{-1}(y_{ijk})=am_{ijk}+\Delta c_{ijk}+v'_{ijk}$. This approach is particularly good when $g_{ijk}$ is an affine function so that the inversion does not produce amplification or biasing of the noise in $v'_{ijk}$.

In some embodiments, the modified noise term $v'_{ijk}=g_{ijk}{}^{-1}(v_{ijk})$ may be amplified or biased by the function inversion. Another embodiment which may be more optimal from a noise perspective is to linearize the measurements around an operating point i.e.:

$$y_{ijk}=g_{ijk}(am_{ijk}+\Delta c_{ijk})+v_{ijk}$$

may be recast as:

$$y_{ijk}\approx g_{ijk}(am_{ijk})+g_{ijk}'(am_{ijk})\Delta c_{ijk}+v_{ijk}$$

in the case where the fraction of free-floating DNA in the maternal blood from the child is small, Δ<<a, and the expansion is a reasonable approximation. Alternatively, for a platform response such as that of the ILLUMINA BEADARRAY, which is monotonically increasing and for which the second derivative is typically negative, one can improve the linearization estimate according to $y_{ijk}\approx g_{ijk}(am_{ijk})+0.5(g_{ijk}'(am_{ijk})+g_{ijk}'(am_{ijk}+\Delta c_{ijk}))\Delta c_{ijk}+v_{ijk}$. The resulting set of equations may be solved iteratively for a and using a method such as Newton-Raphson optimization.

In some embodiments, one may measure at the total amount of DNA on the test chromosome (mother plus fetus) and compare with the amount of DNA on all other chromosomes, based on the assumption that amount of DNA should be constant across all chromosomes. In order to estimate confidence bounds meaningfully, one may look at standard deviation across other chromosome signals that should be euploid to estimate the signal variance and generate a confidence bound. In order to calibrate out the amplification biases amongst different chromosomes, one may find a regression function linking each chromosome's mean signal level to every other chromosomes mean signal level, combine the signal from all chromosome by weighting based on variance of the regression fit, and look to see whether the test chromosome of interest is within the acceptable range as defined by the other chromosomes.

In some embodiments, this method may be used in conjunction with other methods previously disclosed by Gene Security Network, especially those methods that are part of PARENTAL SUPPORT™, and are mentioned elsewhere in this disclosure, such that one may phase the parents so that it is known what is contained on each individual maternal and paternal chromosome. By considering the odds ratio of each of the alleles at heterozygous loci, one may determine which haplotype of the mother is present on the child. Then one can compare the signal level of the measurable maternal haplotype to the paternal haplotype that is present (without background noise from the mother) and see when that ratio of 1:1 is not satisfied due to aneuploidy which causes an imbalance between maternal and paternal alleles.

This list of possible variations on the method is not meant to be exhaustive. Other variation may also be employed. Note that in this disclosure, for the purposes of calculation, certain assumptions may have been made about parameters, characteristics of the data, variables, etc. In these cases, other assumptions may be made that do not change the essence of the invention.

Modeling

In one embodiment, the raw data may be produced by a microarray which measures the response from each possible allele on a selection of SNPs. In an embodiment, the microarray may be an ILLUMINA SNP microarray, or an AFFYMETRIX SNP microarray. In other embodiments other sources of data may also be used, such as a sufficiently large number of TAQMAN probes or a non-SNP based array. The raw genetic data may from other sources as well, such as DNA sequencing.

In this embodiment, a SNP is typically expected to be one of two nucleotides. For example, it may be expected to be either a G or C, and may be measured for the G or C response; alternately, at a SNP which could have A or T it may be measured for the A and T response. Since only two alleles are possible at each SNP, the measurements may be aggregated without regard for whether the SNP is A/T or C/G. Instead, this disclosure may refer to responses on the x and y channels, and generic alleles A or B. Thus the possible genotypes in this example are AA, AB and BB for all SNPs. There are other ways of grouping the allele calls that will not affect the essence of the invention.

Measurements may be initially aggregated over SNPs from the same parent context based on unordered parent genotypes. Each context may be defined by the number of A and number of B alleles from each parent: $[a_m \, b_m \, a_f \, b_f]$ where $a_m + b_m = 2$ and $a_f + b_f = 2$. For example, all SNPs where the mother's genotype is AA and the father's genotype is BB are members of the AA|BB context. The combination of 3 possible genotypes over 2 parents means that the measurements from a single chromosome would consist of 18 context means, 9 on each channel. Consider a copy number hypothesis for the child of the form $(n_m, n_f)$ where $n_m$ is the number of mother copies and $n_f$ is the number of father copies of the chromosome. Let the expected number of As (averaged over SNPs) in the child be $k_x$ and the expected number of Bs be $k_y$ (for a particular context, conditioned on a hypothesis). The expected number of alleles depends on the context and the hypothesis.

$$k_x = 0.5 a_m n_m + 0.5 a_f n_f$$

$$k_y = 0.5 b_m n_m + 0.5 b_f n_f \quad (1)$$

The amount of DNA measured at a SNP will depend on the number of alleles present at that SNP in the maternal and fetal chromosomes, and the overall concentrations of DNA present in the sample from the mother and fetus. The factor $\alpha$ reflects the overall concentration of DNA in the sample, and the ratio of mother to child is 1 to $\delta$.

For SNPs in contexts where the parents are homozygous, the genotypes of a disomic child is known. For example, if one parent's genotype is AA and the other's is BB, the child genotype must be AB. In contrast, SNPs where a parent is heterozygous will have unknown child genotype. Consider the context AB|BB, where the child may inherit either an A or a B from the mother. The most general assumption is that the child will inherit the A and the B with equal probability, and so approximately half of the child genotypes in this context will be AB and half will be BB. Other assumptions may be made regarding the likelihood of a child inheriting a given allele from a given parent. Although the genotype of each child SNP is not known, the average values of $k_x$ and $k_y$ are thus known for SNPs in each context, and so the equations below refers to these averages.

In the example where the parent context is AB|BB, the average number of As in the child SNPs is 0.5 and the average number of Bs is 1.5. The quantities $x_x$ and $x_y$ refer to the average amount of DNA present for SNPs in a particular context, where $x_x$ is the DNA that will be measured on the x channel (allele A) and $x_y$ is the DNA that will be measured on the y channel (allele B).

$$x_x = \alpha(m_x + \delta k_x)$$

$$x_y = \alpha(m_y + \delta k_y) \quad (2)$$

The quantity of DNA may be measured through the platform responses on the x and y channels. SNPs in the same context may be aggregated to produce measurements $y_x, y_y$ which are the context mean responses on the x and y channels. Assume that SNPs are i.i.d.

Extensive analysis (for the whole chromosome mean algorithm, as part of PARENTAL SUPPORT™) has found systematic differences in amplification between chromosomes. Let $y_c$ and $y_1$ be the means from the same context and same sample, from chromosome c and chromosome 1 respectively. The expected value of $y_c/y_1$ is defined as $\beta_c$ and may be calculated from a large set of training data. The training data consists of hundreds of blastomeres which have been analyzed under a consistent laboratory protocol. The chromosome weights $\beta$ depend on microarray type (because different arrays measure different SNPs) and the type of lysis buffer used, but otherwise may be consistent between samples. Therefore, the expected number of As or Bs may be weighted by $\beta$ to account for this effect, resulting in a chromosome-weighted number of alleles $\hat{m}$ or $\hat{k}$:

$$\hat{m}_{xc} = m_{xc} \beta_{xc}$$

$$\hat{m}_{yc} = \underline{m_{yc}} \beta_{yc}$$

$$\hat{k}_{xc} = \underline{k_{xc}} \beta_{xc}$$

$$\hat{k}_{yc} = \underline{k_{yc}} \beta_{yc}$$

By accounting for chromosome variation using a weighted number of alleles, the platform response model $f_x(x_x), f_y(x_y)$ may be considered consistent across chromosomes. However, the bias b may be observed to vary by chromosome and channel and the measurement noise $v$ will vary on each measurement. The bias of a particular chromosome and channel is the mean of the noise-only context, and is therefore a known (directly measured) quantity. The noise-only contexts are AA|AA for the y channel and BB|BB for the x-channel, because in these cases the expected number of the measured allele is zero. Thus, the measurement gives a baseline for the platform response in the absence of the signal which it measures. The scalar noise covariance associated with each context mean measurement may be assumed to be proportional to 1 n where n is the number of SNPs included. This corresponds to the assumption of i.i.d. SNPs within each context. The noise components may be assumed independent and normally distributed.

$$y_x = f_x(x_x) + b_x + v_x$$

$$y_y = f_y(x_y) + b_y + v_y$$

Quadratic Platform Response

In one embodiment, a linear platform response model (affine relationship between amount of DNA and measured signal) may be used. In another embodiment, a quadratic platform response $f(x) = f_1 x^2 + f_2 x$ may be used. In some embodiments, a quadratic platform response may be used where $f_1$ and $f_2$ are specific to each sample and measurement channel and x is the quantity of DNA. Other platform response models may be employed, including higher order algorithmic or exponential relationships. Substituting from (2) for the quantity of DNA results in the following model for the x and y channel responses on chromosome c from context i.

$$\underline{y_{xci}} = f_{1x}\alpha^2\hat{m}^2_{xci} + f_{1x}\alpha^2\delta^2\hat{k}^2_{xci} + 2f_{1x}\alpha^2\delta\hat{m}_{xci}\hat{k}_{\underline{xci}} + f_{2x}\alpha\hat{m}_{xci} + f_{2x}\alpha\delta\hat{k}_{\underline{xci}} + \underline{b_{xc}} + \underline{v_{xci}}$$

$$\underline{y_{yci}} = f_{1y}\alpha^2\hat{m}^2_{yci} + f_{1y}\alpha^2\delta^2\hat{k}^2_{yci} + 2f_{1y}\alpha^2\delta\hat{m}_{\underline{yci}}\hat{k}_{\underline{yci}} + f_{2y}\alpha\hat{m}_{\underline{yci}} + f_{2y}\alpha\delta\hat{k}_{\underline{yci}} + \underline{b_{yc}} + \underline{v_{yci}} \quad (3)$$

Without loss of generality, the DNA concentration a and platform responses $f_{1x}, f_{2x}, f_{1y}, f_{2y}$ may be combined to form the set of 5 parameters for the sample. Note that when the model includes terms of the form $p_1 x \delta^2$, $p_1 x \delta$ and $p_2 x \delta$, and so the parameter estimate cannot be solved exactly using linear methods.

$$\underline{y_{xci}} = p_{1x}\hat{m}^2_{xci} + p_{1x}\delta^2\hat{k}^2_{xci} + 2p_{1x}\delta\hat{m}_{xci}\hat{k}_{\underline{xci}} + p_{2x}\hat{m}_{xci} + p_{2x}\delta\hat{k}_{xci} + \underline{b_{xc}} + \underline{v_{xci}} \quad (5)$$

$$= g_{xci}(p) + \underline{b_{xc}} + \underline{y_{xci}}$$

$$\underline{y_{yci}} = p_{1y}\hat{m}^2_{yci} + p_{1y}\delta^2\hat{k}^2_{yci} + 2p_{1y}\delta\hat{m}_{yci}\hat{k}_{\underline{yci}} + f_{2y}\hat{m}_{\underline{yci}} + f_{2y}\delta\hat{k}_{\underline{yci}} + \underline{b_{yc}} + \underline{v_{yci}}$$

$$= g_{\underline{yci}}(p) + \underline{b_{yc}} + \underline{y_{yci}}$$

$$p = \begin{bmatrix} p_{1x} \\ p_{2x} \\ p_{1y} \\ p_{2y} \\ \delta \end{bmatrix} = \begin{bmatrix} f_{1x}\alpha^2 \\ f_{2x}\alpha^2 \\ f_{1y}\alpha^2 \\ f_{2y}\alpha^2 \\ \delta \end{bmatrix}$$

In this description, this set of parameters p may be assumed to be common to all chromosomes and parent genotype contexts for a single sample, and so the model for a single chromosome c and context i can be written in the following condensed form based on the non-linear platform response function g.

$$\begin{bmatrix} y_{xci} \\ y_{yci} \end{bmatrix} = \begin{bmatrix} g_{xci}(p) \\ g_{yci}(p) \end{bmatrix} + \begin{bmatrix} b_{xc} \\ b_{yc} \end{bmatrix} + \begin{bmatrix} v_{xci} \\ v_{yci} \end{bmatrix}$$

$$y_{ci} = g_{ci}(p) + b_c + v_{ci}$$

The set of N measurements from a sample can be combined to form a vector equation in p.

$$\begin{bmatrix} y_1 \\ \vdots \\ y_N \end{bmatrix} = \begin{bmatrix} g_1(p) \\ \vdots \\ g_N(p) \end{bmatrix} + \begin{bmatrix} b_1 \\ \vdots \\ b_N \end{bmatrix} + \begin{bmatrix} v_1 \\ \vdots \\ v_N \end{bmatrix}$$

$$y = g(p) + b + v$$

In other embodiments, the parameters may be different for different chromosomes, or for different samples.

Linearized Quadratic Platform Response

Consider the linearization of the quadratic platform response at $x = x_0$:

$$f(x) \approx f_1 x_0^2 + f_2 x_0 + (2f_1 x_0 + f_2)(x - x_0)$$

Substitution of the mother's contribution $\alpha\hat{m}$ for the nominal DNA quantity $x_0$ results in the following model.

$$\underline{y_{xci}} = f_{1x}\alpha^2\hat{m}^2_{xci} + 2f_{1x}\alpha^2\delta\hat{m}_{xci}\hat{k}_{\underline{xci}} + f_{2x}\alpha\hat{m}_{xci} + f_{2x}\alpha\delta\hat{k}_{xci}$$

$$\underline{y_{yci}} = f_{1y}\alpha^2\hat{m}^2_{yci} + 2f_{1y}\alpha^2\delta\hat{m}_{\underline{yci}}\hat{k}_{\underline{yci}} + f_{2y}\alpha\hat{m}_{\underline{yci}} + f_{2y}\alpha\delta\hat{k}_{\underline{yci}}$$

Although the platform response is linearized, the model is still non-linear in the set of unknown model parameters defined in (5). In one embodiment, a linear estimation method can be implemented by constructing an augmented parameter set which eliminates the non-linear terms by adding extra degrees of freedom. This augmented parameter set has 8 degrees of freedom. In another embodiment, it is possible to attempt this type of linear solution for the full quadratic model. The four parameters for the X channel are shown, and those for the Y channel are defined similarly.

$$q_x = \begin{bmatrix} q_{1x} \\ q_{2x} \\ q_{3x} \\ q_{4x} \end{bmatrix} = \begin{bmatrix} f_{1x}\alpha^2 \\ f_{2x}\alpha^2 \\ f_{1x}\alpha^2\delta \\ f_{2x}\alpha\delta \end{bmatrix} \quad (6)$$

Using this set of parameters, the linearized model for a chromosome c and context i can be written in matrix form.

$$\underline{A_{xci}} = \begin{bmatrix} \hat{m}^2_{xci} & \hat{m}_{xci} & 2\hat{m}_{xci}\hat{k}_{\underline{xci}} & \hat{k}_{xci} \end{bmatrix}$$

$$\underline{A_{yci}} = \begin{bmatrix} \hat{m}^2_{yci} & \hat{m}_{yci} & 2\hat{m}_{\underline{yci}}\hat{k}_{\underline{yci}} & \hat{k}_{yci} \end{bmatrix}$$

$$A_{ci} = \begin{bmatrix} A_{xci} & 0 \\ 0 & A_{yci} \end{bmatrix}$$

$$\begin{bmatrix} y_{xci} \\ y_{yci} \end{bmatrix} = A_{ci} \begin{bmatrix} q_x \\ q_y \end{bmatrix} + \begin{bmatrix} b_{xc} \\ b_{yc} \end{bmatrix} + \begin{bmatrix} v_{xci} \\ v_{cyi} \end{bmatrix}$$

$$y_{ci} = A_{ci}q + b_{ci} + v_{ci}$$

The measurements from all chromosomes, contexts and channels may be combined into a single matrix equation with parameters q in $R^8$ as follows:

$$\begin{bmatrix} y_1 \\ \vdots \\ y_N \end{bmatrix} = \begin{bmatrix} A_1 \\ \vdots \\ A_N \end{bmatrix} + \begin{bmatrix} b_1 \\ \vdots \\ b_N \end{bmatrix} + \begin{bmatrix} v_1 \\ \vdots \\ v_N \end{bmatrix} \quad (7)$$

$$y = Aq + b + v$$

Recall that y are the context mean measurements, A is the set of known coefficients, q is the set of parameters to be estimated, b is the known bias vector, and v is assumed zero-mean Gaussian noise.

Parameter Estimation

In one embodiment, the strategy for parameter estimation is to assume a subset of the child's chromosomes are disomic (having one copy from each parent) and use these to learn the model parameters for the child sample. These sample model parameters are then used to classify the remaining chromosomes, determining how many copies are present from each parent. Thus, the child allele contributions $\hat{m}_{xci}$, $\hat{m}_{yci}$ may be calculated from (1) at the parameter estimation step under the assumption that the mother and father copy number contributions $n_m$ and $n_f$ are both one. If D is the number of assumed disomic chromosomes, then the measurement vector y for parameter estimation has size 18D (from nine context means measured on two channels).

Linearized Quadratic Sensor Model

The linearized quadratic model (7) leads to straightforward least-squares (LS) or maximum likelihood (ML) solutions for the best estimate of q. The maximum likelihood solution depends on the number of SNPs incorporated in each measurement, given in the diagonal matrix N. In an embodiment, the maximum likelihood solution is used because the informativeness of the different measurement components varies widely, and the matrix N which determines this variation is known.

$$q^*_{LS} = \text{argmin}\|y - (Aq + b)\|^2$$
$$= (A^T A)^{-1} A^T (y - b)$$

$$q^*_{ML} = \text{argmax} P(y; q)$$
$$= \text{argmin} \|N^{-0.5}(y - Aq - b)\|^2$$
$$= (A^T N^{-1} A)^{-1} A^T N^{-1} (y - b)$$

Quadratic Sensor Model

The quadratic sensor model may not lead to closed form solutions for the parameter estimate p which best fits the measurements. In another embodiment, a gradient descent optimization method may be applied which iteratively improves on an initial guess for p in order to minimize a cost function. A non-linear least squares formulation for p minimizes the mean square difference between the measured data and the values predicted by the model.

$$p^* = \text{argmin}\|y - g(p) - b\|^2$$

Commercial non-linear optimization functions, such as MATLAB's FMINCON, use iterative methods to find a local minimum of a user-provided cost function by numerically approximating the function's gradient.

The parameter estimate q* based on the linearized model may provide a convenient initial condition for the non-linear optimization because it solves an approximation of the same problem but can be calculated in closed form at little computational cost. Comparison of the linearized (q) and non-linear (p) parameters below shows that the mapping from p to q is not invertible.

$$q = \begin{bmatrix} q_{1x} \\ q_{2x} \\ q_{3x} \\ q_{4x} \\ q_{1y} \\ q_{2y} \\ q_{3y} \\ q_{4y} \end{bmatrix} = \begin{bmatrix} f_{1x}\alpha^2 \\ f_{2x}\alpha \\ f_{1x}\alpha^2\delta \\ f_{2x}\alpha\delta \\ f_{1y}\alpha^2 \\ f_{2y}\alpha \\ f_{1y}\alpha^2\delta \\ f_{2y}\alpha\delta \end{bmatrix}, p = \begin{bmatrix} p_{1x} \\ p_{2x} \\ p_{1y} \\ p_{2y} \\ \delta \end{bmatrix} = \begin{bmatrix} f_{1x}\alpha^2 \\ f_{2x}\alpha^2 \\ f_{1y}\alpha^2 \\ f_{2y}\alpha^2 \\ \delta \end{bmatrix}$$

The mapping from p to q will be written q(p) and is as follows.

$$q(p) = [p_{1x}, p_{2x}, p_{1x}\delta, p_{2x}\delta, p_{1y}, p_{2y}, p_{1y}, p_{2y}\delta]^T$$

Given $q = q^*_{MLE}$, select $p_0 = \text{argmin}\|q - q(p)\|_2$, which has a closed form polynomial solution. Then $p_0$ may be used as an initial condition for an iterative solution of $p^* = \text{arg min}\|y - g(p) - b\|$.

An estimate of the distribution of the noise vector v may be used in the calculation of observation likelihoods. The fit error vector $e = y - g(p^*) - b$ is a sample from the distribution of v. Recall that the assumption of i.i.d. SNPs implies that the context means will have variance proportional to the included number of SNPs. Thus, the covariance V of v has the form $\gamma N^{-1}$ where $\gamma$ is scalar and N is the diagonal matrix defining the number of SNPs measured in each context mean. The matrix N is known, and $\gamma$ is estimated as the variance of the components of $N^{0.5}e$.

Copy Number Determination

After estimating the model parameters for a particular sample based on a set of known disomic chromosomes, the task is to estimate the copy number for the chromosome of interest, or for the remainder of the chromosomes. Recall that a child copy number hypothesis has the form $Hn_m n_f$ where $(n_m, n_f)$ represent the number of copies contributed by the mother and father, respectively. In an embodiment, the focus is placed on detection of trisomies, where one parent contributes an extra copy, because these errors may result in a viable fetus, and conditions such as Down Syndrome. The copy number hypothesis predicts the expected number of child alleles present at a SNP with a particular parent context, according to (1). For example, consider the context AA|BB where the mother has genotype AA and the father has genotype BB. Under the disomy hypothesis H11, the child's genotype will be AB, but under the maternal trisomy hypothesis H21 the child's genotypes will be AAB, and a higher signal on the x channel can be detected due to the extra A. The number of child alleles present appears in the matrix A in the linearized model and in the function g(p) in the quadratic model, and depends on the assumed hypothesis in this manner. Thus, the assumption of a particular copy number hypothesis h results in a corresponding model $A^h q$ or $g^h(p)$. The various hypotheses will be evaluated by considering the likelihood of the observed data under the different models.

Consider the measurement vector $y_c \in R^{18}$ from a chromosome c. Recall that $y_c$ contains the 18 context mean measurements from the chromosome, where each is an average of the measurements from SNPs in a parent genotype context. Substitution of a hypothesis into the learned model results in a distribution $p(y_c|h)$ which is implicitly dependent on the learned model parameters. The probabilities of the various hypotheses h can be solved for from the likelihoods $\{p(y_c|h)\}$ by incorporating priors using Bayes rule. Classification is possible when the distributions $p(y_c|h_i)$ and $p(y_c|h_j)$ are distinguishable for different hypotheses $h_i$ and $h_j$. For a single chromosome, define $d_{ij}$ as the mean square difference in model output comparing hypotheses $h_i$ and $h_j$.

$$\underline{d_{ij}} = \frac{1}{18}\sum_{i=1}^{18} (g^i(p^*) - g^j(p^*))^2$$

A high-confidence call between hypotheses $h_i$ and $h_j$ can be expected when $d_{ij}$ is large compared to the sensor noise variance.

Estimation may be based on the quadratic sensor model, $y=g(p)+b+v$. Conditioned on a set of model parameters and a hypothesis, the measurement vector $y_c$ is normally distributed with mean $g^h(p^*)+b$ and covariance $V=\gamma N^{-1}$. By defining the error vector $e_c^h = y_c - g^h(p^*) - b$ for a hypothesis h and chromosome c, it is possible to see that $e_c^h$ is normally distributed with zero mean and covariance V and $e_c^{hT}V^{-1}e_c^h$ has the chi-squared distribution with 18 degrees of freedom.

$$p(y_v|h) = p_{x_{18}^2}\left((y_c - g^h(p^*) - b)\frac{1}{\gamma}N(y_c - g^h(p^*) - b)\right)$$

Copy Number Calling with Phased Paternal Genetic Data

In an embodiment of the invention, phased father genotype data may be used. In this section is described an embodiment that takes advantage of the phased parental data. This section discloses an extension of an embodiment described earlier; it is designed for the case where phased father genotypic data is available, and allows for more accurate parameter estimation and hypothesis fitting.

When the genotype data is phased, then the AB genotype can be distinguished from the BA genotype. Therefore, in the AB genotype, the first haplotype has the A allele at a given locus, and the second haplotype has the B allele at the locus, whereas, in the BA genotype, the first haplotype has the B allele at the locus, and the second haplotype has the A allele at the locus. When genotype is unphased, or unordered no distinction is made between AB and BA, and it is typically referred to as AB.

Phasing of father genotype may be done by various methods, including several that may be found in the three patent applications Rabinowitz 2006, 2008 and 2009 that are incorporated by reference. It is assumed, in this section, that phased father genotypic data is available, meaning, on all chromosomes, the ordered father genotype is known on all SNPs, i.e. one can distinguish between first and second haplotype of the father's genotype. If the father's genotypic data is phased, and thus AB BA for father, while mother data is not phased, i.e. AB=BA for mother, then there are twelve different possible parental contexts: AA|AA, AA|AB, AA|BA, AA|BB, AB|AA, AB|AB, AB|BA, AB|BB, BB|AA, BB|AB, BB|BA, and BB|BB.

Measurements may be initially aggregated over SNPs from the same parental context based on phased father genotypes. Each context may be defined by the number of A and number of B alleles from the mother, from the first father strand and from the second father strand: $[a_m\ b_m\ a_{f1}\ b_{f1}\ a_{f2}\ b_{f2}]$ where $a_m+b_m=2$ and $a_{f1}+b_{f1}=1$, $a_{f2}+b_{f2}=1$. The combination of 3 possible mother genotypes and 4 possible father genotypes means that the measurements from a single chromosome will consist of 24 context means, 12 on each channel.

Consider a copy number hypothesis for the child, for a particular chromosome, of the form $(n_m, n_f)$ where $n_m$ is the number of mother copies and $n_f$ is the number of father copies of the chromosome. For the phased paternal genotype this hypothesis may be written in a form $(n_m, n_{f1}, n_{f2})$ where $n_m$ is the number of mother copies and $n_{f1}$ is the number of father copies of first strand, $n_{f2}$ is the number of father copies of second strand of the chromosome, where $n_f=n_{f1}+n_{f2}$. (Note: this is different notation than mentioned elsewhere in this disclosure, which is in the form $(m,f_x,f_y)$, and that takes into account the sex chromosome.) Thus the normal disomy hypothesis, previously written in the form $(n_m, n_f)=(1,1)$ can be extended into two sub-hypotheses $(n_m, n_{f1}, n_{f2})=(1,1,0)$ and $(n_m, n_{f1}, n_{f2})=(1,0,1)$, where the two paternal haplotypes are differentiated. Maternal trisomy, previously written in form (2,1), can be extended into sub-hypotheses (2,1,0) and (2,0,1). Paternal trisomy can be extended into sub-hypotheses including paternal mitotic trisomies (1,2,0), (1,0,2) and paternal meiotic trisomy (1,1,1).

Due to possible crossovers between paternal strands, the child hypothesis, written in the form $(n_m, n_{f1}, n_{f2})$, does not have to stay the same throughout the chromosome. For example suppose that a chromosome has normal disomy with first paternal strand (1,1,0), on a set of adjacent SNPs. If there is a crossover of paternal strands on the following SNP, the copy number hypothesis of the child changes to (1,0,1), now involving second father strand.

In order to keep a hypothesis constant over a given set of SNPs for the purpose of calculation, divide the chromosome into N segments of adjacent SNPs. One may divide the chromosomes into segments in a number of ways, for example, to keep the number of SNPs per segment constant, or to keep number of segments per chromosomes constant. Assume here that the copy number hypothesis is constant throughout the segment, with no crossovers present. Ambiguous segments with possible paternal crossovers are omitted in this explanation for clarity.

For each segment, group the measurements by parental context, and aggregate the intensity measurements over each group of SNPs. Therefore, in this case, the measurements from a single chromosome will consist of 24*N context means, 12*N on each channel (for each of N segments on a chromosome).

Let the expected number of As (averaged over SNPs) in the child be $k_x$ and the expected number of Bs be $k_y$ (for a particular context, conditioned on a hypothesis). The expected number of alleles depends on the context and the hypothesis. For each segment of the chromosome, for each ordered parental context:

$k_x = 0.5a_m n_m + a_{f1} n_{f1} + a_{f2} n_{f2}$ $k_y = 0.5b_m n_m + b_{f1} n_{f1} + b_{f2} n_{f2}$

The model is similar to the model for unordered parental contexts:

$$x_x = \alpha(m_x + \delta k_x)$$

$$x_y = \alpha(m_y + \delta k_y)$$

$$y_x = f_x(x_x) + b_x + v_x$$

$$y_y = f_y(x_y) + b_y + v_y$$

and one may use the model $f(x) = f_1 x^2 + f_2 x$

Chromosomes that are assumed to be disomic may be used for fitting the parameters of the model ('training' chromosomes), i.e. assume that $(n_m, n_f) = (1,1)$. One may determine the exact disomy sub-hypothesis, $(n_m, n_{f1}, n_{f2})$, either (1,1,0) or (1,0,1) on each segment of each 'train' chromosome, by looking at the intensity responses for different ordered parental contexts, for each segment separately, as follows:

First, determine the noise level for x channel response by looking at the x channel response for parental context BB|BB, and determine the noise level for y channel by looking at the y channel response for parental context AA|AA, (where the x channel measures A alleles, and the y channel measures the B alleles). Then, if the hypothesis is (1,1,0), the y channel responses for ordered parental context AA|AB are expected to only be noise, with no signal, and have the same behavior as the responses for context AA|AA. Similarly, x channel responses for ordered parental context BB|BA are expected to only be noise, with no signal, and have the same behavior as the responses for context BB|BB.

If the hypothesis is (1,0,1), the y channel responses for ordered parental context AA|BA should only be noise, with no signal, and have the same behavior as the responses for context AA|AA. Similarly, the x channel responses for ordered parental context BB|AB should only be noise, with no signal, and have the same behavior as the responses for context BB|BB.

Choose, as the most likely sub-hypothesis on this segment, whichever one of hypothesis (1,1,0) or (1,0,1), that fits the data better. One may omit from further analysis segments where the choice is ambiguous, i.e. segments where crossover probably occurred.

In order to train the model using disomic chromosomes, fit the parameters $(\alpha, \delta, f_1, f_2)$ for this model from the $12 \times 2 \times N \times n_t$ observations, where $n_t$ is the number of 'training' chromosomes used.

In an embodiment, the focus is placed on detection of trisomies, where one parent contributes an extra copy. Note that most viable aneuploidy births are as a result of trisomies. Hypothesis fitting on 'test' chromosomes (the chromosome of interest) may be done similarly as for unordered genotypes, except that each trisomy sub-hypothesis (for example (101) vs. (110)) may be fit separately for each segment, and the hypothesis for the ploidy state of the segments may be aggregated, only focusing on the overall ploidy state (now considering (101) and (110) to be the same, both disomy; focusing on, for example, disomy vs. maternal trisomy vs. paternal trisomy) and statistics may be calculated for whole chromosomes.

In particular suppose that, on segment i, the probability of a particular sub-hypothesis in ordered hypothesis format is $P_i(n_m, n_{f1}, n_{f2})$. In unordered hypothesis format, calculate the probability of the disomy hypothesis as $P_i(n_m, n_f) = P_i(1,1) = P_i(1,1,0) + P_i(1,0,1)$. For maternal trisomy $P_i(2,1) = P_i(2,1,0) + P_i(2,0,1)$. For paternal trisomy $P_i(1,2) = N_t^*(P_i(1,2,0) + P_i(1,0,2)) + p_{me}^* P_i(1,1,1)$, where $p_{mt}$ is the probability of mitotic paternal trisomy given that paternal trisomy occurred, and $p_m$ is the probability of mitotic paternal trisomy given that paternal trisomy occurred, determined from literature and general practice. Note that mitotic trisomies and meiotic trisomies may be differentiated, or they may not be differentiated.

Given the hypothesis probability $P_i(n_m, n_f)$ for each segment i=1, ..., N, calculate the probability over the whole chromosome as $P(n_m, n_f) = \Pi_{i=1, ..., N} P_i(n_m, n_f)$. The hypothesis call for each chromosome is made selecting the hypothesis with highest probability.

It should be obvious, given the benefit of this disclosure, how to modify the method for a case where the maternal genotype is phased, and the paternal genotype is not phased. It should also be obvious, given the benefit of this disclosure, how to modify the method for a case where both the paternal and the maternal genotypes are phased.

Experimental Section

The experimental aspect of the invention is described here. In order to demonstrate the reduction of practice of the invention, a mixture of cells from multiple individuals was made, where the ploidy state of the individuals was known, and the algorithms described above were used to determine the ploidy state of one of the individuals.

Genomic samples were prepared from a maternal (AG16778, CORIELL) and an offspring (AG16777, CORIELL) tissue culture cell line. Cells were grown under standard conditions (1×RPMI Medium 1640, 15% Fetal Bovine Serum (FBS), 0.85% Streptomycin), and genomic DNA was purified using a QIAAMP DNA Micro Kit (QIAGEN) according to manufacturer's recommendations. Purified DNA was quantified using a NANODROP instrument (THERMO SCIENTIFIC) and diluted to appropriate concentrations in 1×Tris-EDTA buffer. A series of three mixed genomic samples (a-c) were prepared by combining (a) 59.4 ng AG16777 DNA with 132.6 ng AG16778 DNA (30% AG16777), (b) 76.8 ng AG16777 DNA with 115.2 ng AG16778 DNA (40% AG16777), and (c) 115.2 ng AG16777 DNA with 76.8 ng AG16778 DNA (60% AG16777). The three samples were diluted in $H_2O$ for a total DNA concentration of 3 ng/ul. Samples were stored at −20 C, and then analyzed on the INFINIUM array platform (ILLUMINA), which was performed according to manufacturer's recommendations.

This method is appropriate for any nucleic acids which may be used for the ILLUMINA INFINIUM array platform, or any other SNP based genotyping method, for example isolated free-floating DNA from plasma or amplifications (e.g. whole genome amplification, PCR) of the same, isolated genomic DNA from other cell types (e.g. lymphocytes) or amplifications of the same. Any method that generates genomic DNA (e.g. extraction of DNA, purification) may be used for sample preparation.

The genomic DNA used here was premixed to simulate a mix of fetal and maternal DNA, however, the method is also applicable to DNA (or amplifications thereof) as such (i.e. not premixed). Three samples were prepared from these cell lines, having 30, 40 and 60 percent of offspring DNA (relative to the mother). The offspring cell line has trisomy on chromosome 21.

Figure 1B:
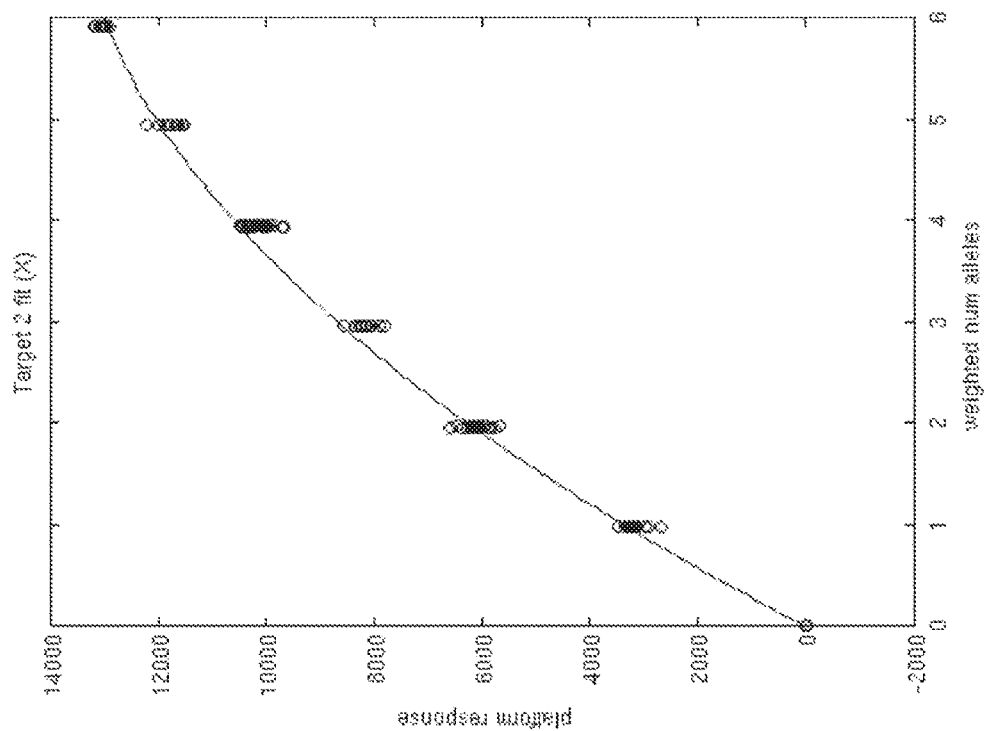

FIGS. 1A and 1B show the model parameter fit for (b), the 40 percent sample. The x-axis shows the total number of alleles on the channel of interest, $\hat{m} + \delta \hat{k}$, These values range from zero to four. Considering the x channel, there are no expected alleles in the BB|BB context, ranging to four expected alleles in the AA|AA context, with two from the mother's DNA and two from the child's DNA. The y-axis measures platform response as a function of the number of alleles. Circles are the measured context means (9 on each channel from each of the assumed disomic chromosomes) and the line shows the corresponding value predicted by the model parameters p*, for the same number of alleles. Note that the y-axis values on the two plots are quite different, showing that the x and y channel responses must be modeled separately.

Figure 2:
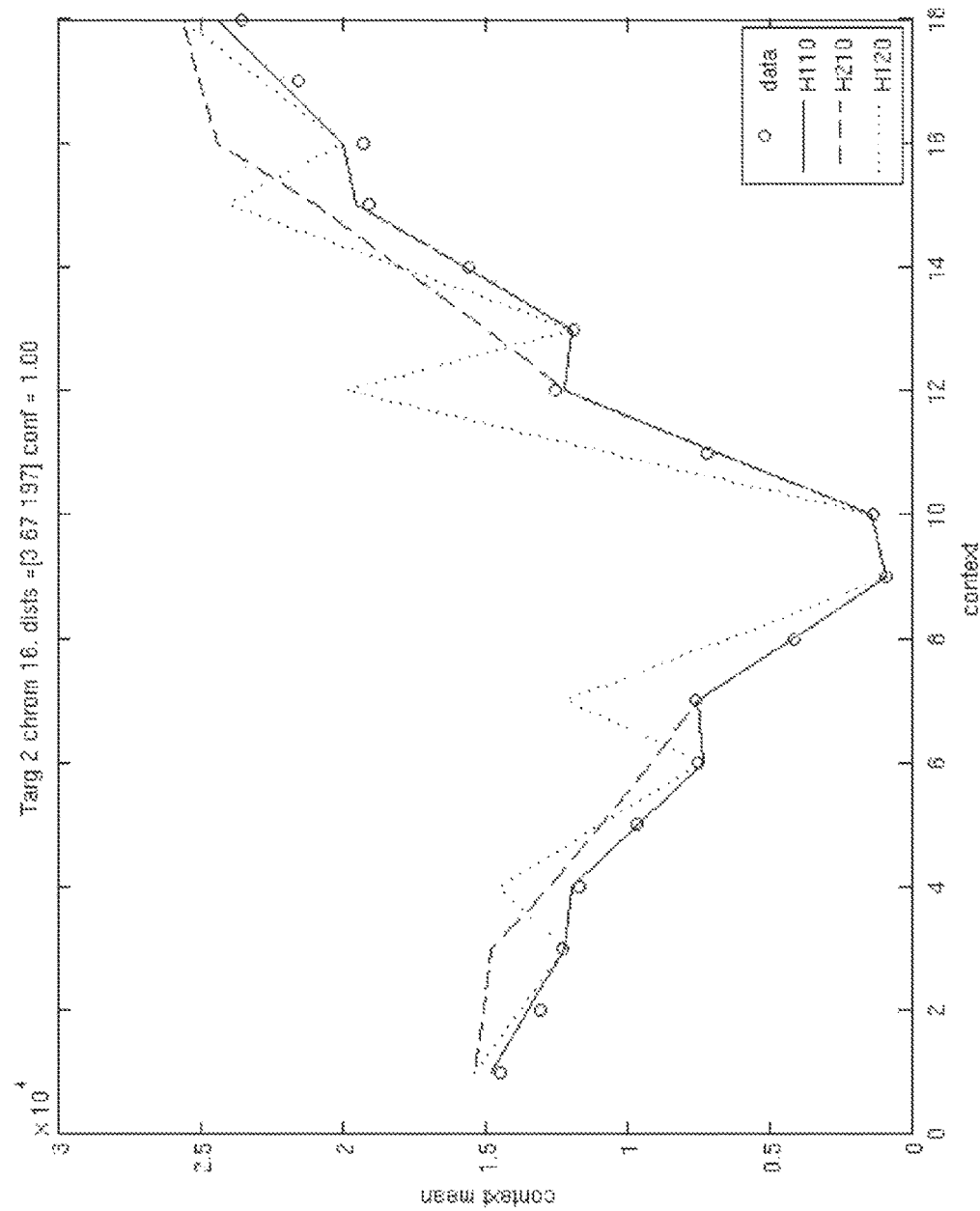
FIG. 2 shows components of the measurement vector compared against the predictions under three hypotheses. This plot is from chromosome 16 of a sample which is 40 percent target DNA and 60 percent mother DNA. The true hypothesis is H110.

FIG. 2 shows the 18 components of the measurement $y_{16}$ from chromosome 16 on the sample with 40 percent fetal DNA. The first nine measurements are from the x channel and the next nine measurements are from the y channel. The contexts are ordered as follows: AA|AA, AA|AB, AA|BB, AB|AA, AB|AB, AB|BB, BB|AA, BB|AB, BB|BB. The 18 measurements are compared to the predicted values for the three hypotheses H11, H12 and H21. It is clear that the data most closely matches the H11 hypothesis (disomy). The correct call was produced by the algorithm, with assigned probability of 1.0 based on a uniform prior distribution.

Figure 3:
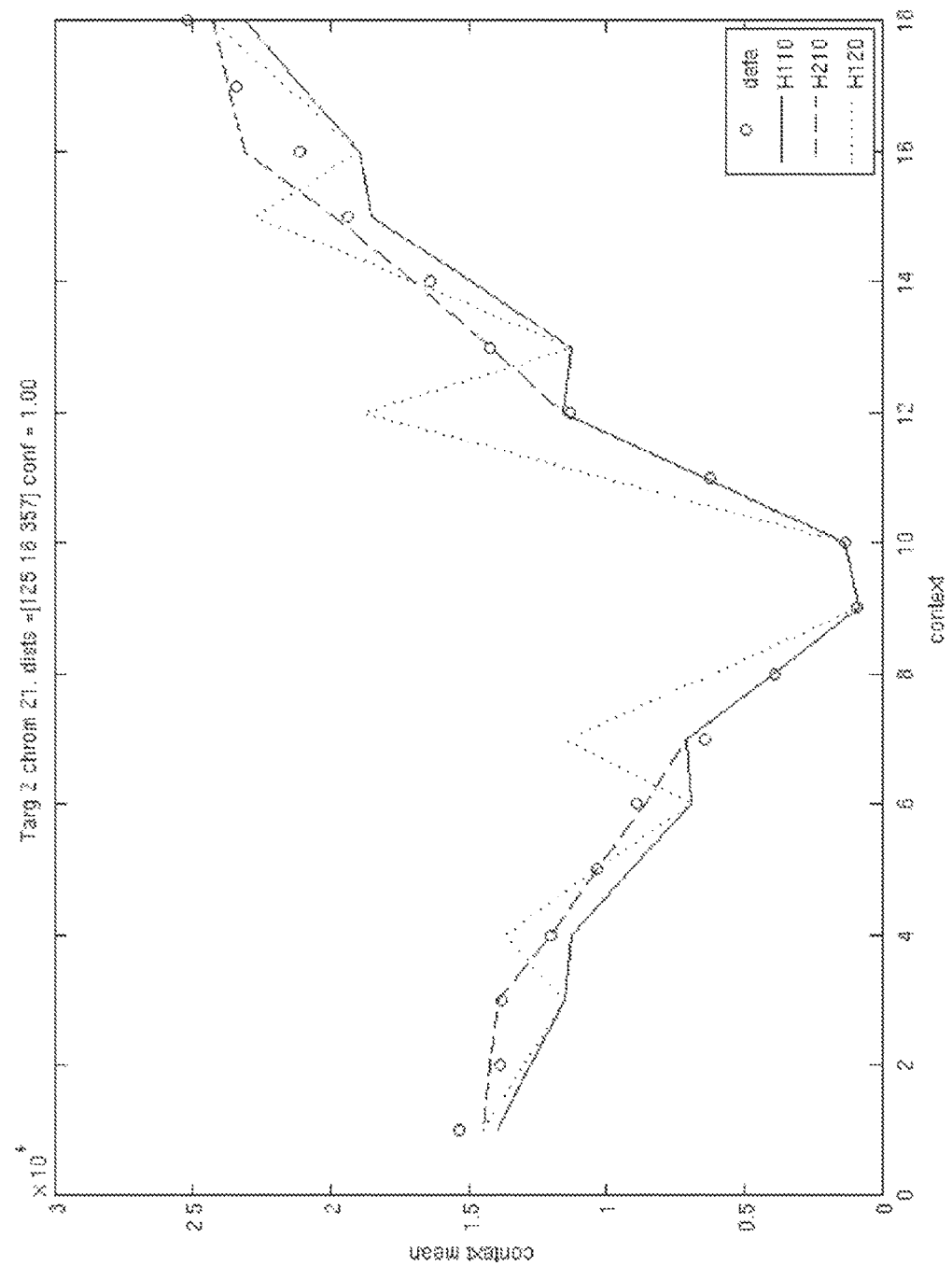
FIG. 3 shows components of the measurement vector compared against the predictions under three hypotheses.

FIG. 3 shows chromosome 21, which has a truth of H21. The correct call was also made with assigned probability 1.0. The complete set of hypothesis calls and assigned probabilities is shown in Table 1. The context mean measurements for the classified chromosomes for samples (a), (b), and (c), are shown in Tables 2, 3 and 4, respectively. In these tables, columns correspond to the chromosomes and rows correspond to the context mean measurements, ordered as described for FIG. 2 by channel and then by context.

TABLE 1

Algorithm hypothesis calls and assigned probabilities for each classified chromosome. The correct hypothesis for each chromosome is shown in the column header.

| Sample | ch16 (H11) | ch17 (H11) | ch18 (H11) | ch19 (H11) | ch20 (H11) | ch21 (H21) | ch22 (H11) |
|---|---|---|---|---|---|---|---|
| 30% child | H11 (1.0) | H11 (1.0) | H11 (1.0) | H11 (1.0) | H11 (1.0) | H21 (1.0) | H11 (1.0) |
| 40% child | H11 (1.0) | H11 (1.0) | H11 (1.0) | H11 (1.0) | H11 (1.0) | H21 (1.0) | H11 (1.0) |
| 60% child | H11 (1.0) | H11 (1.0) | H11 (1.0) | H11 (1.0) | H11 (1.0) | H21 (1.0) | H11 (1.0) |

TABLE 2

Context means from sample (a) with 30 percent child DNA

| ch16 (H11) | ch17 (H11) | ch18 (H11) | ch19 (H11) | ch20 (H11) | ch21 (H21) | ch22 (H11) |
|---|---|---|---|---|---|---|
| 13391.0 | 13396.3 | 12737.6 | 12610.0 | 14139.3 | 13669.2 | 13319.9 |
| 12720.2 | 12986.3 | 12257.6 | 11849.5 | 13484.8 | 12696.4 | 13033.4 |
| 12474.1 | 12259.0 | 11153.3 | 11295.9 | 13145.1 | 13000.0 | 11616.9 |
| 10096.4 | 10076.4 | 9118.7 | 10133.4 | 10396.8 | 10062.3 | 10119.0 |
| 9231.1 | 9342.0 | 8880.2 | 8523.3 | 9370.7 | 9120.1 | 8874.9 |
| 8133.1 | 7753.6 | 7552.1 | 7611.9 | 8629.2 | 8504.7 | 7635.7 |
| 4809.1 | 4907.5 | 4522.1 | 4103.8 | 4723.6 | 4222.9 | 4482.7 |
| 2778.9 | 2989.5 | 2708.7 | 2926.5 | 3029.2 | 2678.2 | 2813.7 |
| 932.0 | 924.6 | 915.3 | 930.7 | 936.7 | 955.1 | 921.0 |
| 1530.8 | 1520.7 | 1452.7 | 1514.7 | 1557.4 | 1467.0 | 1507.1 |
| 4897.6 | 4880.0 | 4428.4 | 4652.7 | 5139.2 | 4370.2 | 4880.5 |
| 7991.4 | 7858.6 | 7259.3 | 7149.2 | 8376.7 | 7583.1 | 7284.4 |
| 12680.9 | 12625.4 | 12151.6 | 12257.1 | 13690.0 | 13237.8 | 12740.3 |
| 14408.8 | 14339.7 | 14093.1 | 13331.4 | 14892.0 | 14312.9 | 14088.5 |
| 15857.3 | 15468.9 | 14785.9 | 15413.2 | 16198.5 | 15942.9 | 15458.1 |
| 19034.9 | 19216.9 | 18527.3 | 17459.5 | 19282.5 | 19296.2 | 18271.1 |
| 19949.6 | 20399.3 | 19282.9 | 19156.4 | 21229.8 | 20667.8 | 20356.4 |
| 20759.7 | 20659.5 | 19992.0 | 19859.9 | 21461.8 | 21454.6 | 20586.5 |

TABLE 3

Context means from sample (b) with 40 percent child DNA

| ch16 (H11) | ch17 (H11) | ch18 (H11) | ch19 (H11) | ch20 (H11) | ch21 (H21) | ch22 |
|---|---|---|---|---|---|---|
| 12550.6 | 12579.9 | 11992.0 | 11803.7 | 13301.4 | 13019.7 | 12486.2 |
| 11761.7 | 12087.9 | 11409.0 | 10959.7 | 12553.3 | 11961.6 | 12050.4 |
| 11470.2 | 11190.0 | 10345.8 | 10184.9 | 11997.4 | 12311.9 | 10620.9 |
| 9730.8 | 9724.5 | 8820.5 | 9744.3 | 10006.4 | 9796.9 | 9635.1 |
| 8663.3 | 8788.1 | 8336.2 | 8028.7 | 8812.4 | 8652.7 | 8313.7 |
| 7374.2 | 6921.7 | 6858.2 | 6788.7 | 7869.5 | 7931.6 | 6872.3 |
| 5240.3 | 5318.0 | 4882.5 | 4355.9 | 5226.3 | 4499.0 | 4848.2 |
| 2876.9 | 3081.3 | 2786.8 | 3032.0 | 3133.0 | 2721.5 | 2884.9 |
| 747.0 | 739.0 | 725.6 | 742.6 | 754.5 | 775.7 | 735.5 |
| 1215.7 | 1202.2 | 1139.8 | 1195.3 | 1247.6 | 1162.4 | 1195.4 |
| 5141.4 | 5141.1 | 4647.9 | 4884.0 | 5419.2 | 4491.4 | 5066.3 |
| 8788.4 | 8589.7 | 8054.1 | 7676.0 | 9180.7 | 8239.9 | 7860.0 |

TABLE 3-continued

Context means from sample (b) with 40 percent child DNA

| ch16 (H11) | ch17 (H11) | ch18 (H11) | ch19 (H11) | ch20 (H11) | ch21 (H21) | ch22 |
|---|---|---|---|---|---|---|
| 11789.9 | 11721.3 | 11387.4 | 11299.3 | 12930.0 | 12800.3 | 11749.7 |
| 14003.2 | 13876.2 | 13700.7 | 12946.6 | 14557.5 | 14022.1 | 13684.1 |
| 15911.6 | 15468.6 | 14791.0 | 15421.7 | 16203.6 | 16097.6 | 15506.3 |
| 18219.5 | 18507.0 | 17671.1 | 16562.4 | 18738.9 | 18920.1 | 17571.3 |
| 19453.4 | 19745.8 | 18751.0 | 18557.6 | 20749.5 | 20360.6 | 19775.2 |
| 20405.2 | 20347.0 | 19747.6 | 19406.0 | 21205.3 | 21409.5 | 20303.8 |

TABLE 4

Context means from sample (c) with 40 percent child DNA

| ch16 (H11) | ch17 (H11) | ch18 (H11) | ch19 (H11) | ch20 (H11) | ch21 (H21) | ch22 |
|---|---|---|---|---|---|---|
| 14453.4 | 14433.9 | 13747.4 | 13574.8 | 15284.4 | 15340.9 | 14299.5 |
| 13022.7 | 13352.4 | 12687.0 | 11874.1 | 13907.0 | 13834.7 | 13265.3 |
| 12211.6 | 11774.2 | 10772.2 | 10840.1 | 12664.4 | 13763.4 | 11278.3 |
| 11674.6 | 11651.0 | 10614.0 | 11718.0 | 11951.0 | 11943.3 | 11750.2 |
| 9652.1 | 9865.7 | 9356.0 | 9078.6 | 9857.3 | 10296.7 | 9339.5 |
| 7456.1 | 6979.7 | 7149.0 | 6720.3 | 8212.8 | 8899.0 | 6930.3 |
| 7521.5 | 7710.6 | 7260.6 | 6449.0 | 7607.0 | 6434.7 | 7132.0 |
| 4117.2 | 4415.2 | 4005.3 | 4324.8 | 4473.7 | 3862.9 | 4128.1 |
| 860.4 | 849.9 | 833.1 | 864.3 | 863.7 | 894.7 | 846.3 |
| 1360.4 | 1364.5 | 1275.6 | 1349.8 | 1398.1 | 1353.4 | 1345.3 |
| 7185.7 | 7019.5 | 6493.3 | 6789.4 | 7586.5 | 6193.1 | 6964.6 |
| 12481.0 | 12200.9 | 11442.4 | 11061.2 | 13030.5 | 11304.5 | 11423.5 |
| 11840.0 | 11758.5 | 11671.3 | 11148.7 | 13512.2 | 14165.6 | 11967.1 |
| 15575.7 | 15291.0 | 15286.0 | 14449.9 | 16439.0 | 16386.7 | 15302.0 |
| 19001.6 | 18522.8 | 17684.2 | 18689.6 | 19325.3 | 19377.0 | 18569.2 |
| 19158.2 | 19308.5 | 18786.6 | 17259.8 | 19780.8 | 21111.1 | 18409.1 |
| 21537.7 | 21797.0 | 20716.9 | 20383.8 | 23039.6 | 23429.0 | 21894.6 |
| 23523.5 | 23412.2 | 22665.6 | 22280.1 | 24448.8 | 25148.6 | 23313.8 |

In one embodiment, identification of parent haplotypes (parent phase) may be used to estimate the recombination locations that determine which haplotypes are present in the child. Identification of which parent haplotype is present at each position in the child determines the child genotype. This may result in lower model variances because positions with different child genotypes will no longer be averaged. Certain methods disclosed herein can be modified to detect meiotic trisomies when both of a parent's haplotypes are present.

Some Embodiments

In some embodiments of the present disclosure, a method for determining the ploidy state of one or more chromosome in a target individual may include any of the following steps, and combinations thereof:

In some embodiments, genetic data from the target individual and from one or more related individuals may be obtained. In one embodiment, the related individuals include both parents of the target individual. In one embodiment, the related individuals include siblings of the target individual. In one embodiment, the related individuals may include the parents and one or more grandparents. This genetic data for individuals may be obtained from data in silico; it may be output data from an informatics method designed to clean genetic data, or it may be from other sources. In some embodiments of the invention, the genotypic data of the parents can be obtained and optionally phased using methods found in the three patent applications, Rabinowtiz 2006, 2008 and 2009, referenced elsewhere in this application.

Any number of methods may be used to obtain the parental genotypic data provided that the set of SNPs measured on the mixed sample of fetal and maternal DNA is sufficiently overlapping with the set of SNPs for which that parental genotype is known.

Amplification of the DNA, a process which transforms a small amount of genetic material to a larger amount of genetic material that contains a similar set of genetic data, can be done by a wide variety of methods, including, but not limited to, Polymerase Chain Reaction (PCR), ligand mediated PCR, degenerative oligonucleotide primer PCR, Multiple Displacement Amplification, allele-specific amplification techniques, Molecular Inversion Probes (MIP), padlock probes, other circularizing probes, and combination thereof. Many variants of the standard protocol may be used, for example increasing or decreasing the times of certain steps in the protocol, increasing or decreasing the temperature of certain steps, increasing or decreasing the amounts of various reagents, etc. The DNA amplification transforms the initial sample of DNA into a sample of DNA that is similar in the set of sequences, but of much greater quantity. In some cases, amplification may not be required.

The genetic data of the target individual and/or of the related individual can be transformed from a molecular state to an electronic state by measuring the appropriate genetic material using tools and or techniques taken from a group including, but not limited to: genotyping microarrays, APPLIED BIOSCIENCE'S TAQMAN SNP genotyping assay, the ILLUMINA genotyping system, for example the ILLUMINA BEADARRAY platform using, for example, the 1M-DUO chip, an AFFYMETRIX GENOTYPING PLATFORM, such as the AFFYMETRIX 6.0 GENECHIP, AFFYMETRIX'S GENFLEX TAG array, other genotyping microarrays. A high throughput sequencing method may be used, such as Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, or any other sequencing method, fluorescent in-situ hybridization (FISH), array comparative genomic hybridization (CGH), other high through-put genotyping platforms, and combinations thereof. All of these methods physically transform the genetic data stored in a sample of DNA into a set of genetic data that is typically stored in a memory device en route to being processed.

Any relevant individual's genetic data can be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof.

In some embodiments, a set of at least one ploidy state hypothesis may be created for each of the chromosomes of interest of the target individual. Each of the ploidy state hypotheses may refer to one possible ploidy state of the chromosome or chromosome segment of the target individual. The set of hypotheses may include some or all of the possible ploidy states that the chromosome of the target individual may be expected to have. Some of the possible ploidy states may include nullsomy, monosomy, disomy, uniparental disomy, euploidy, trisomy, matching trisomy, unmatching trisomy, maternal trisomy, paternal trisomy, tetrasomy, balanced (2:2) tetrasomy, unbalanced (3:1) tetrasomy, other aneuploidy, and they may additionally involve unbalanced translocations, balanced translocations, Robertsonian translocations, recombinations, deletions, insertions, crossovers, and combinations thereof.

In some embodiments, the set of determined probabilities may then be combined. This may entail, for each hypothesis, averaging or multiplying the probabilities as determined by each technique, and it also may involve normalizing the hypotheses. In some embodiments, the probabilities may be combined under the assumption that they are independent. The set of the products of the probabilities for each hypothesis in the set of hypotheses is then output as the combined probabilities of the hypotheses.

In some embodiments of the invention, the determined probabilities as determined by the method disclosed herein may be combined with probabilities of other hypotheses that are calculated by diagnostic methods that work on entirely different precepts. For example, some methods used for prenatal diagnosis involve measuring the levels of certain hormones in maternal blood, where those hormones are correlated with various genetic abnormalities. Some examples of this are the first trimester serum screen, the triple test, and the quad test. Some methods involve measuring dimensions and other qualities of the fetus that can be measured using ultrasound, for example, the nuchal translucency. Some of these methods can calculate a probability that the fetus is euploid, or is afflicted with trisomy, especially trisomy 18 and/or trisomy 21. In a case where multiple methods are used to determine the likelihood of a given outcome, where none of the methods are definitive in and of themselves, it is possible to combine the information given by those methods to make a prediction that is more accurate than any of the individual methods. For example, in the triple test, combining the information given by the three different hormones can result in a prediction of genetic abnormalities that is more accurate than any of the individual hormone levels may predict. In some embodiments, the method involves measuring maternal blood levels of alpha-fetoprotein (AFP). In some embodiments, the method may involve measuring maternal blood levels of unconjugated estriol ($UE_3$). In some embodiments, the method may involve measuring maternal blood levels of beta human chorionic gonadotropin ($\beta$-hCG). In some embodiments, the method may involve measuring maternal blood levels of invasive trophoblast antigen (ITA). In some embodiments, the method may involve measuring maternal blood levels of inhibin-A. In some embodiments, the method may involve measuring maternal blood levels of pregnancy-associated plasma protein A (PAPP-A). In some embodiments, the method may involve measuring maternal blood levels of other hormones or maternal serum markers. In some embodiments, some of the predictions may have been made using other methods. In some embodiments, some of the predictions may have been made using a fully integrated test such as one that combines ultrasound and blood test at about 10-14 weeks of pregnancy and a second blood test at about 15-20 weeks. In some embodiments, the method involves measuring the fetal nuchal translucency (NT) as measured by ultrasound. In some embodiments, the method involves using the measured levels of the aforementioned hormones for making predictions. In some embodiments the method involves a combination of the aforementioned methods.

The output of the method described herein can be combined with the output of one or a plurality of other methods. There are many ways to combine the predictions, for example, one could convert the hormone measurements into a multiple of the median (MoM) and then into likelihood ratios (LR). Similarly, other measurements could be transformed into LRs using the mixture model of NT distributions. The LRs for NT and the biochemical markers could be multiplied by the age and gestation-related risk to derive the risk for various conditions, such as trisomy 21. Detection rates (DRs) and false-positive rates (FPRs) could be calculated by taking the proportions with risks above a given risk threshold.

One embodiment may involve a situation with four measured hormone levels, where the probability distribution around those hormones is known: $p(x_1, x_2, x_3, x_4|e)$ for the euploid case and $p(x_1, x_2, x_3, x_4|a)$ for the aneuploid case. Then one could measure the probability distribution for the DNA measurements, $g(y|e)$ and $g(y|a)$ for the euploid and aneuploid cases respectively. Assuming they are independent, given the assumption of euploid/aneuploid, one could combine as $p(x_1, x_2, x_3, x_4|a)g(y|a)$ and $p(x_1, x_2, x_3, x_4|e)g(y|e)$ and then multiply each by the prior $p(a)$ and $p(e)$ given the maternal age. One could then choose the case that is highest probability. In one embodiment it is possible to evoke the central limit theorem to assume distribution on $g(y|a \text{ or } e)$ is Gaussian, and measure mean and standard deviations by looking at multiple samples. In another embodiment, one could assume they are not independent given the outcome and collect enough samples to estimate the joint distribution $p(x_1, x_2, x_3, x_4|a \text{ or } e)$.

In one embodiment, the ploidy state for the target individual is determined to be the ploidy state that is associated with the hypothesis whose probability is the greatest. In some cases, one hypothesis will have a normalized, combined probability greater than 90%. Each hypothesis is associated with one, or a set of, ploidy states, and the ploidy state associated with the hypothesis whose normalized, combined probability is greater than 90%, or some other threshold value, such as 50%, 80%, 95%, 98%, 99%, or 99.9%, may be chosen as the threshold required for a hypothesis to be called as the determined ploidy state.

In some embodiments, the knowledge of the determined ploidy state may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy. In some embodiments the clinical decision may involve an intervention designed to decrease the severity of the phenotypic presentation of a genetic disorder.

In some cases, it may be desirable to include a large number of related individuals into the calculation to determine the most likely genetic state of a target. In some cases, running the algorithm with all of the desired related individuals may not be feasible due to limits of computational power or time. The computing power needed to calculate the most likely allele values for the target may increase exponentially with the number of sperm, blastomeres, and other input genotypes from related individuals. In one embodiment, these problems may be overcome by using a method termed "subsetting", where the computations may be divided into smaller sets, run separately, and then combined. In one embodiment of the present disclosure, one may have the genetic data of the parents along with that of ten embryos and ten sperm. In this embodiment, one could run several smaller sub-algorithms with, for example three embryos and three sperm, and then pool the results. In one embodiment the number of sibling embryos used in the determination may be from one to three, from three to five, from five to ten, from ten to twenty, or more than twenty. In one embodiment the number of sperm whose genetic data is known may be from one to three, from three to five, from five to ten, from ten to twenty, or more than twenty. In one embodiment each chromosome may be divided into two to five, five to ten, ten to twenty, or more than twenty subsets.

In one embodiment of the invention, any of the methods described herein may be modified to allow for multiple targets to come from same target individual, for example, multiple blood draws from the same pregnant mother. This may improve the accuracy of the model, as multiple genetic measurements may provide more data with which the target genotype may be determined. In one embodiment, one set of target genetic data served as the primary data which was reported, and the other served as data to double-check the primary target genetic data. In one embodiment, a plurality of sets of genetic data, each measured from genetic material taken from the target individual, are considered in parallel, and thus both sets of target genetic data serve to help determine which sections of parental genetic data, measured with high accuracy, composes the fetal genome.

In some embodiments the source of the genetic material to be used in determining the genetic state of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cell, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells.

In one embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoll gradients with different osmolalities, or galactose specific lectin method.

In one embodiment of the present disclosure, the target individual is a fetus, and the different genotype measurements are made on a plurality of DNA samples from the fetus. In some embodiments of the invention, the fetal DNA samples are from isolated fetal cells where the fetal cells may be mixed with maternal cells. In some embodiments of the invention, the fetal DNA samples are from free floating fetal DNA, where the fetal DNA may be mixed with free floating maternal DNA. In some embodiments, the fetal DNA may be mixed with maternal DNA in ratios ranging from 99.9:0.1% to 90:10%; 90:10% to 50:50%; 50:50% to 10:90%; or 10:90% to 0.1:99.9%.

In one embodiment of the present disclosure, one may use an informatics based technique such as the ones described in this disclosure to determine whether or not the cells are in fact fetal in origin. In one embodiment of the present disclosure, one may then use an informatics based technique such as the ones described in this disclosure to determine the ploidy state of one or a set of chromosomes in those cells. In one embodiment of the present disclosure, one may then use an informatics based technique such as the ones described in this disclosure to determine the genetic state of the cells. When applied to the genetic data of the cell, PARENTAL SUPPORT™ could indicate whether or not a nucleated red blood cell is fetal or maternal in origin by identifying whether the cell contains one chromosome from the mother and one from the father, which would indicate that it is fetal, or two chromosomes from the mother, which would indicate that it is maternal.

In one embodiment, the method may be used for the purpose of paternity testing. For example, given the SNP-based genotypic information from the mother, and from a man who may or may not be the genetic father, and the measured genotypic information from the mixed sample, it is possible to determine if the genotypic information of the male indeed represents that actual genetic father of the gestating fetus. A simple way to do this is to simply look at the contexts where the mother is AA, and the possible father is AB or BB. In these cases, one may expect to see the father contribution half (AA|AB) or all (AA|BB) of the time, respectively. Taking into account the expected ADO, it is straightforward to determine whether or not the fetal SNPs that are observed are correlated with those of the possible father.

One embodiment of the present disclosure could be as follows: a pregnant woman wants to know if her fetus is afflicted with Down Syndrome, and/or if it will suffer from Cystic Fibrosis, and she does not wish to bear a child that is afflicted with either of these conditions. A doctor takes her blood, and stains the hemoglobin with one marker so that it appears clearly red, and stains nuclear material with another marker so that it appears clearly blue. Knowing that maternal red blood cells are typically anuclear, while a high proportion of fetal cells contain a nucleus, he is able to visually isolate a number of nucleated red blood cells by identifying those cells that show both a red and blue color. The doctor picks up these cells off the slide with a micromanipulator and sends them to a lab which amplifies and genotypes ten individual cells. By using the genetic measurements, the PARENTAL SUPPORT™ method is able to determine that six of the ten cells are maternal blood cells, and four of the ten cells are fetal cells. If a child has already been born to a pregnant mother, PARENTAL SUPPORT™ can also be used to determine that the fetal cells are distinct from the cells of the born child by making reliable allele calls on the fetal cells and showing that they are dissimilar to those of the born child. Note that this method is similar in concept to the paternal testing embodiment of the invention. The genetic data measured from the fetal cells may be of very poor quality, containing many allele drop outs, due to the difficulty of genotyping single cells. The clinician is able to use the measured fetal DNA along with the reliable DNA measurements of the parents to infer aspects of the genome of the fetus with high accuracy using PARENTAL SUPPORT™, thereby transforming the genetic data contained on genetic material from the fetus into the predicted genetic state of the fetus, stored on a computer. The clinician is able to determine both the ploidy state of the fetus, and the presence or absence of a plurality of disease-linked genes of interest. It turns out that the fetus is euploidy, and is not a carrier for cystic fibrosis, and the mother decides to continue the pregnancy.

In another embodiment, a couple where the mother, who is pregnant, and is of advanced maternal age wants to know whether the gestating fetus has Down syndrome or some other chromosomal abnormality. The obstetrician takes a blood draw from the mother and father. A technician centrifuges the maternal sample to isolate the plasma and the buffy coat. The DNA in the buffy coat and the paternal blood sample are transformed through amplification and the genetic data encoded in the amplified genetic material is further transformed from molecularly stored genetic data into electronically stored genetic data by running the genetic material on a SNP array to measure the parental genotypes. The plasma sample is may be further processed by a method such as running a gel, or using a size exclusion column, to isolate specific size fractions of DNA. Other methods may be used to enrich the fraction of fetal DNA in the sample. An informatics based technique that includes the invention described herein, such as PARENTAL SUPPORT™, may be used to determine the ploidy state of the fetus. It is determined that the fetus has Down syndrome. A report is printed out, or sent electronically to the pregnant woman's obstetrician, who transmits the diagnosis to the woman. The woman, her husband, and the doctor sit down and discuss the options. The couple decides to terminate the pregnancy based on the knowledge that the fetus is afflicted with a trisomic condition.

In another embodiment, a pregnant woman, hereafter referred to as 'the mother' may decide that she wants to know whether or not her fetus(es) are carrying any genetic abnormalities or other conditions. She may want to ensure that there are not any gross abnormalities before she is confident to continue the pregnancy. She may go to her obstetrics doctor, who may take a sample of her blood. He may also take a genetic sample, such as a buccal swab, from her cheek. He may also take a genetic sample from the father of the fetus, such as a buccal swab, a sperm sample, or a blood sample. The doctor may enrich the fraction of free floating fetal DNA in the maternal blood sample. The doctor may enrich the fraction of enucleated fetal blood cells in the maternal blood sample. The doctor may use various aspects of the method described herein to determine genotypic data of the fetus. That genotypic data may include the ploidy state of the fetus, and/or the identity of one or a number of alleles in the fetus. A report may be generated summarizing the results of the prenatal diagnosis. The doctor may tell the mother the genetic state of the fetus. The mother may decide to discontinue the pregnancy based on the fact that the fetus has one or more chromosomal, or genetic abnormalities, or undesirable conditions. She may also decide to continue the pregnancy based on the fact that the fetus does not have any gross chromosomal or genetic abnormalities, or any genetic conditions of interest.

Another example may involve a pregnant woman who has been artificially inseminated by a sperm donor, and is pregnant. She is wants to minimize the risk that the fetus she is carrying has a genetic disease. She has blood drawn at a phlebotomist, and techniques described in this disclosure are used to isolate three nucleated fetal red blood cells, and a tissue sample is also collected from the mother and genetic father. The genetic material from the fetus and from the mother and father are amplified as appropriate and genotyped using the ILLUMINA INFINIUM BEADARRAY, and the methods described herein clean and phase the parental and fetal genotype with high accuracy, as well as to make ploidy calls for the fetus. The fetus is found to be euploid, and phenotypic susceptibilities are predicted from the reconstructed fetal genotype, and a report is generated and sent to the mother's physician so that they can decide what clinical decisions may be best.

Another example may involve a woman who is pregnant but, owing to having had more than one sexual partner, is not certain of the paternity of her fetus. The woman wants to know who is the genetic father of the fetus she is carrying. She and one of her sexual partners go to the hospital and both donate a blood sample. The clinician, using the methods described in this disclosure, is able to determine the paternity of the fetus. It turns out that the biological father of the fetus is not her favored partner, and based on this information, the woman decides to terminate her pregnancy.

In some embodiments of the present disclosure, a plurality of parameters may be changed without changing the essence of the present disclosure. For example, the genetic data may be obtained using any high throughput genotyping platform, or it may be obtained from any genotyping method, or it may be simulated, inferred or otherwise known. A variety of computational languages could be used to encode the algorithms described in this disclosure, and a variety of computational platforms could be used to execute the calculations. For example, the calculations could be executed using personal computers, supercomputers, and parallel computers.

In some embodiments of the invention, the method may be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits). The results may be output in the form of a printed report, a display on a screen, or may be saved by way of a memory device that involves storage of information by way of a physical change in the substrate of the memory device, such as those listed above. A report describing the determination of the ploidy state of the fetus, either in print, or electronically, may be generated that transmits the information to a heath care practitioner, and/or the parent. A clinical decision may be made based on the determination. In some embodiments, the clinical decision to terminate a pregnancy may be made contingent upon that the fetus is aneuploid; the undesirability of the condition of aneuploidy in the fetus provides the basis for the decision to terminate the pregnancy. In some embodiments of the invention, the method includes the decision to terminate or to not terminate a pregnancy, and may also include the execution of that decision.

In one embodiment, the raw genetic material of the mother and father is transformed by way of amplification to an amount of DNA that is similar in sequence, but larger in quantity. Then, by way of a genotyping method the genotypic data that is encoded by nucleic acids is transformed into genetic measurements that may be stored physically and/or electronically on a memory device, such as those described above. The relevant algorithms that makeup the PARENTAL SUPPORT™ algorithm, relevant parts of which are discussed in detail in this disclosure, are translated into a computer program, using a programming language. Then, through the execution of the computer program on the computer hardware, instead of being physically encoded bits and bytes, arranged in a pattern that represents raw measurement data, they become transformed into a pattern that represents a high confidence determination of the ploidy state of the fetus. The details of this transformation will rely on the data itself and the computer language and hardware system used to execute the method described herein, but is predictable if those contexts are known. Then, the data that is physically configured to represent a high quality ploidy determination of the fetus is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue the pregnancy, in which case a gestating fetus with a genetic abnormality is transformed into non-living fetus. The transformations listed herein may be aggregated, such that, for example, one may transform the genetic material of a pregnant mother and the father, through a number of steps outlined in this disclosure, into a medical decision consisting of aborting a fetus with genetic abnormalities, or consisting of continuing the pregnancy. Alternately, one may transform a set of genotypic measurements into a report that helps a physician treat his pregnant patient.

In one embodiment of the invention, the method described herein can be used to determine the ploidy state of a fetus even when the host mother, i.e. the woman who is pregnant, is not the biological mother of the fetus she is carrying.

Some of the math in this disclosure makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, hexasomy etc., without changing the fundamental concepts of the present disclosure. At the same time, it is possible to focus on a smaller number of ploidy states, for example, only trisomy and disomy. Note that ploidy determinations that indicate a non-whole number of chromosomes may indicate mosaicism in a sample of genetic material.

In some embodiments of the present disclosure, a related individual may refer to any individual who is genetically related, and thus shares haplotype blocks with the target individual. Some examples of related individuals include: biological father, biological mother, son, daughter, brother, sister, half-brother, half-sister, grandfather, grandmother, uncle, aunt, nephew, niece, grandson, granddaughter, cousin, clone, the target individual himself/herself/itself, and other individuals with known genetic relationship to the target. The term 'related individual' also encompasses any embryo, fetus, sperm, egg, blastomere, blastocyst, or polar body derived from a related individual.

In some embodiments of the present disclosure, the target individual may refer to an adult, a juvenile, a fetus, an embryo, a blastocyst, a blastomere, a cell or set of cells from an individual, or from a cell line, or any set of genetic material. The target individual may be alive, dead, frozen, or in stasis. In some embodiments of the present disclosure, as all living or once living creatures contain genetic data, the methods are equally applicable to any live or dead human, animal, or plant that inherits or inherited chromosomes from other individuals.

It is also important to note that the fetal genetic data that can be generated by measuring the amplified DNA from a small sample of fetal DNA can be used for multiple purposes. For example, it can be used for detecting aneuploidy, uniparental disomy, unbalanced translocations, sexing the individual, as well as for making a plurality of phenotypic predictions based on phenotype-associated alleles. In some embodiments, particular genetic conditions may be focused on before screening, and if certain loci are especially relevant to those genetic conditions, then a more appropriate set of SNPs which are more likely to co-segregate with the locus of interest, can be selected, thus increasing the confidence of the allele calls of interest.

In some embodiments, the genetic abnormality is a type of aneuploidy, such as Down syndrome (or trisomy 21), Edwards syndrome (trisomy 18), Patau syndrome (trisomy 13), Turner Syndrome (45X0) and Klinefelter's syndrome (a male with 2 X chromosomes). Congenital disorders, such as those listed in the prior sentence, are commonly undesirable, and the knowledge that a fetus is afflicted with one or more phenotypic abnormalities may provide the basis for a decision to terminate the pregnancy.

In some embodiments, the phenotypic abnormality may be a limb malformation, or a neural tube defect. Limb malformations may include, but are not limited to, amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis.

In some embodiments, the phenotypic abnormality may be a congenital malformation of the heart. Congenital malformations of the heart may include, but are not limited to, patent ductus arteriosus, atrial septal defect, ventricular septal defect, and tetralogy of fallot.

In some embodiments, the phenotypic abnormality may be a congenital malformation of the nervous system. Congenital malformations of the nervous system include, but are not limited to, neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

In some embodiments, the phenotypic abnormality may be a congenital malformation of the gastrointestinal system. Congenital malformations of the gastrointestinal system include, but are not limited to, stenosis, atresia, and imperforate anus.

In some embodiments, the genetic abnormality is either monogenic or multigenic. Genetic diseases include, but are not limited to, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease—juvenile, Connexin26, SMA, Rett syndrome, Phenylketonuria, Becker Muscular Dystrophy, Duchennes Muscular Dystrophy, Fragile X syndrome, Hemophilia A, Alzheimer dementia—early onset, Breast/Ovarian cancer, Colon cancer, Diabetes/MODY, Huntington disease, Myotonic Muscular Dystrophy, Parkinson Disease—early onset, Peutz-Jeghers syndrome, Polycystic Kidney Disease, Torsion Dystonia.

In some embodiments, the systems, methods, and techniques of the present disclosure are used in methods to increase the probability of implanting an embryo obtained by in vitro fertilization that is at a reduced risk of carrying a predisposition for a genetic disease.

In an embodiment of the present disclosure, methods are disclosed for the determination of the ploidy state of a target individual where the measured genetic material of the target is contaminated with genetic material of the mother, by using the knowledge of the maternal genetic data. This is in contrast to methods that are able to determine the ploidy state of a target individual from genetic data that is noisy due to poor measurements; the contamination in this data is random. This is also in contrast to methods that are able to determine the ploidy state of a target individual from genetic data that is difficult to interpret because of contamination by DNA from unrelated individuals; the contamination in that data is genetically random. In an embodiment, the methods disclosed herein are able to determine the ploidy state of a target individual when the difficulty of interpretation is due to contamination of DNA from a parent; the contamination in this data is at least half identical to the target data, and is therefore difficult to correct for. In order to achieve this end, in an embodiment a method of the present disclosure uses the knowledge of the contaminating maternal genotype to create a model of the expected genetic measurements given a mixture of the maternal and the target genetic material, wherein the target genetic data is not known a priori. This step is not necessary where the uncertainty in the genetic data is due to random noise.

In an embodiment, a method for determining the copy number of a chromosome of interest in a target individual, using genotypic measurements made on genetic material from the target individual, wherein the genetic material of the target individual is mixed with genetic material from the mother of the target individual, comprises obtaining genotypic data for a set of SNPs of the parents of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and of the genetic data of the parents of the target individual; and using the determined probabilities of each hypothesis to determine the most likely copy number of the chromosome of interest in the target individual. In an embodiment, the target individual and the parents of the target individual are human test subjects.

In an embodiment, a computer implemented method for determining the copy number of a chromosome of interest in a target individual, using genotypic measurements made on genetic material from the target individual, where the genetic material of the target individual is mixed with genetic material from the mother of the target individual, comprises obtaining genotypic data for a set of SNPs of the parents of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and of the genetic data of the parents of the target individual; and using the determined probabilities of each hypothesis to determine the most likely copy number of the chromosome of interest in the target individual.

In an embodiment, a method for determining the copy number of a chromosome of interest in a target individual, using genotypic measurements made on genetic material from the target individual, wherein the genetic material of the target individual is mixed with genetic material from the mother of the target individual, comprises obtaining genotypic data for a set of SNPs of the mother of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and of the genetic data of the mother of the target individual; and using the determined probabilities of each hypothesis to determine the most likely copy number of the chromosome of interest in the target individual.

In an embodiment, a computer implemented method for determining the copy number of a chromosome of interest in a target individual, using genotypic measurements made on genetic material from the target individual, where the genetic material of the target individual is mixed with genetic material from the mother of the target individual, comprises obtaining genotypic data for a set of SNPs of the mother of the target individual; making genotypic measurements for the set of SNPs on a mixed sample that comprises DNA from the target individual and also DNA from the mother of the target individual; creating, on a computer, a set of ploidy state hypothesis for the chromosome of interest of the target individual; determining, on the computer, the probability of each of the hypotheses given the genetic measurements of the mixed sample and of the genetic data of the mother of the target individual; and using the determined probabilities of each hypothesis to determine the most likely copy number of the chromosome of interest in the target individual.

Combinations of the Aspects of the Present Disclosure

As noted previously, given the benefit of this disclosure, there are more aspects and embodiments that may implement one or more of the systems, methods, and features, disclosed herein. All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for determining the number of copies of a chromosome or chromosome segment of interest in the genome of a gestating fetus, the method comprising:
    measuring genetic data at a plurality of polymorphic loci on at least one chromosome that is expected to be disomic in both the mother and the fetus and a plurality of polymorphic loci on at least chromosome or chromosome segment of interest, which comprises amplifying at least 500 polymorphic loci from a mixed sample comprising DNA derived from the fetus and DNA derived from the mother, wherein the mixed sample is prepared from a maternal blood or plasma sample that comprises free floating fetal and maternal DNA;
    determining a ratio of DNA derived from the fetus to DNA derived from the mother from the measured genetic data at the plurality of polymorphic loci on the at least one chromosome that is expected to be disomic in both the mother and the fetus;
    creating hypotheses specifying the number of copies of the chromosome or chromosome segment of interest in the genome of the fetus;
    determining, on a computer, the probability of each of the hypotheses using the measured genetic data for the chromosome or chromosome segment of interest and the ratio of DNA derived from the fetus to DNA derived from the mother; and
    selecting the hypothesis with the greatest probability, thereby determining the number of copies of the chromosome or chromosome segment of interest in the genome of the fetus.

2. The method of claim 1, further comprising obtaining measured genetic data at the plurality of polymorphic loci on the chromosome or chromosome segment of interest from genetic material from the mother and/or father of the fetus, wherein the probability of each of the hypotheses is determined using the measured genetic data of the mother and/or father for the chromosome or chromosome segment of interest, the measured genetic data of the mixed sample for the chromosome or chromosome segment of interest, and the ratio of DNA derived from the fetus to DNA derived from the mother.

3. The method of claim 1, wherein the method comprises measuring genetic data at (i) a plurality of single nucleotide polymorphisms (SNPs) from the chromosome or chromosome segment of interest and (ii) a plurality of SNPs from at least one chromosome or chromosome segment that is expected to be disomic in the fetus.

4. The method of claim 3, wherein the method comprises:
    measuring the amount of each allele at each of the SNPs from genetic material from the mother to obtain genotypic data for the mother;

using the genotypic data of the mother to determine parental contexts for each of the SNPs;
grouping the genotypic measurements of the mixed sample into the parental contexts; using the grouped genotypic measurements from the at least one chromosome that is expected to be disomic to determine a platform response;
using the grouped genotypic measurements from the at least one chromosome that is expected to be disomic to determine a ratio of DNA derived from the fetus to DNA derived from the mother;
using the determined platform response and the determined ratio to calculate expected SNP measurements for the set of SNPs in at least one parental context under each hypothesis; and
calculating the probability that each of the hypotheses is true from the platform response, the determined ratio, the grouped genotypic measurements of the mixed sample, and the expected SNP measurements for the at least one parental context.

5. The method of claim 1, comprising:
estimating expected data for the mixed sample for the case where the chromosome or chromosome segment of interest is euploid;
estimating expected data for the mixed sample for the case where the chromosome or chromosome segment of interest is aneuploid using the ratio of DNA derived from the fetus to DNA derived from the mother in the mixed sample;
calculating (i) a data fit between the measured genetic data and the expected data for the euploid case and (ii) a data fit between the measured genetic data and the expected data for the aneuploid case; and
selecting the case for which the data fit is best, thereby determining whether the chromosome or chromosome segment of interest in the fetus is euploid or aneuploid.

6. The method of claim 5, further comprising obtaining measured genetic data at the plurality of polymorphic loci from genetic material from the mother and/or father of the fetus for the chromosome or chromosome segment of interest, wherein the expected data for the aneuploidy case is determined using the measured genetic data of the mother and/or father, the measured genetic data for the chromosome or chromosome segment of interest of the mixed sample, and the ratio of DNA derived from the fetus to DNA derived from the mother.

7. The method of claim 1, further comprising aggregating the measured data on the chromosome or chromosome segment of interest before determining the number of copies of the chromosome or chromosome segment of interest.

8. The method of claim 7, wherein determining the number of copies of the chromosome or chromosome segment of interest in the genome of the fetus comprises comparing an aggregated value for the chromosome or chromosome segment of interest to the aggregated value for one or more chromosomes expected to be disomic.

9. The method of claim 1, wherein determining the number of copies of the chromosome or chromosome segment of interest in the genome of the fetus comprises comparing a mean value for the measured data for the chromosome or chromosome segment of interest to a mean value for the measured data for one or more other chromosomes.

10. The method of claim 1, comprising calculating a maximum likelihood estimate of the ratio of DNA derived from the fetus to DNA derived from the mother, thereby determining the ratio of DNA derived from the fetus to DNA derived from the mother.

11. The method of claim 1, wherein determining the ratio of DNA derived from the fetus to DNA derived from the mother comprises:
obtaining measured genetic data from the mixed sample by measuring the quantity of each allele at a plurality of polymorphic loci on at least one chromosome that is expected to be disomic in both the mother and the fetus;
estimating expected allele measurements in the mixed sample at the plurality of polymorphic loci on the at least one chromosome for possible ratios of DNA derived from the fetus to DNA derived from the mother;
calculating a relative probability of each of the possible ratios using the model and the measured quantity of each allele at the plurality of polymorphic loci on the at least one chromosome that is expected to be disomic in both the mother and the fetus from the mixed sample; and
selecting the possible ratio with the greatest probability, thereby determining the ratio of DNA derived from the fetus to DNA derived from the mother.

12. The method of claim 11, further comprising
obtaining measured genetic data from the mother by measuring the quantity of each allele at the plurality of polymorphic loci on the at least one chromosome that is expected to be disomic in both the mother and the fetus in genetic material from the mother;
optionally obtaining measured genetic data from the father of the fetus by measuring the quantity of each allele at the plurality of polymorphic loci on the at least one chromosome that is expected to be disomic in both the mother and the fetus in genetic material from the father; and
determining the ratio of DNA derived from the fetus to DNA derived from the mother given the measured genetic data of the mixed sample for the at least one chromosome that is expected to be disomic in both the mother and the fetus, the measured genetic data of mother for the at least one chromosome that is expected to be disomic in both the mother and the fetus.

13. The method of claim 11, wherein the polymorphic loci comprise SNPs.

14. The method of claim 1, wherein the ratio of DNA derived from the fetus to DNA derived from the mother is determined by measuring the amount of an allele at one or more polymorphic loci on the at least one chromosome that is expected to be disomic in both the mother and the fetus in which the fetus has the allele and the mother does not have the allele.

15. The method of claim 1, wherein the ratio of DNA derived from the fetus to DNA derived from the mother in the mixed sample is determined by:
identifying one or more polymorphic loci on the at least one chromosome that is expected to be disomic in both the mother and the fetus where the mother is homozygous for a first allele at the polymorphic locus; and
using the amount of the second allele in the mixed sample for each of the identified polymorphic loci to determine the ratio of DNA derived from the fetus to DNA derived from the mother.

16. The method of claim 1, wherein the ratio of DNA derived from the fetus to DNA derived from the mother is determined by:

identifying one or more polymorphic loci on the at least one chromosome that is expected to be disomic in both the mother and the fetus where the mother is homozygous for a first allele at the polymorphic locus, and the father is (i) heterozygous for the first allele and a second allele or (ii) homozygous for a second allele at the polymorphic locus; and using the amount of the second allele in the mixed sample for each of the identified polymorphic loci to determine the ratio of DNA derived from the fetus to DNA derived from the mother.

17. The method of claim 1, wherein the method further comprises measuring the difference in methylation between one or more maternal and fetal alleles.

18. The method of claim 1, further comprising:
determining the likelihood that the fetal genome contains three copies of a chromosome or chromosome segment of interest using the ratio of DNA derived from the fetus to DNA derived from the mother.

19. The method of claim 1, wherein a confidence is computed for the determination of the number of copies of the chromosome or chromosome segment of interest in the genome of the target individual.

20. The method of claim 1, wherein the ratio of DNA derived from the fetus to DNA derived from the mother is determined for individual chromosomes.

21. The method of claim 1, wherein the step of measuring genetic data is performed by measuring genetic material using a technique selected from the group consisting of padlock probes, circularizing probes, genotyping microarrays, SNP genotyping assays, chip based microarrays, bead based microarrays, other SNP microarrays, other genotyping methods, Sanger DNA sequencing, pyrosequencing, high throughput sequencing, reversible dye terminator sequencing, sequencing by ligation, sequencing by hybridization, other methods of DNA sequencing, other high throughput genotyping platforms, fluorescent in situ hybridization (FISH), comparative genomic hybridization (CGH), array CGH, and combinations thereof.

22. The method of claim 1 wherein the chromosome of interest is selected from the group consisting of chromosome 13, chromosome 18, chromosome 21, the X chromosome, the Y chromosome, and combinations thereof.

23. A method for determining the number of copies of a chromosome or chromosome segment of interest in the genome of a gestating fetus, the method comprising:
obtaining a plurality primers to a locus (i) that is known to be polymorphic in the human population and (i) that is likely to be informative based on the rate of SNP heterozygosity in the human population for the locus; wherein an informative polymorphic loci is a SNP locus on at least one chromosome that is expected to be disomic in both the mother and the fetus where the mother is homozygous for a first allele at that locus, and the father is (i) heterozygous for the first allele and a second allele or (ii) homozygous for a second allele at that locus;
amplifying at least 500 SNPs from DNA in a mixed sample comprising DNA derived from the fetus and DNA derived from the mother by using the plurality of primers to obtain amplified products comprising the plurality of polymorphic loci on the at least one chromosome that is expected to be disomic, wherein the mixed sample is prepared from a maternal blood or plasma sample that comprises free floating fetal and maternal DNA;
measuring an amount of the amplified products to obtain a measured quantity of each allele at the plurality of polymorphic loci on the at least one chromosome that is expected to be disomic;
determining a ratio of DNA derived from the fetus to DNA derived from the mother using (i) the measured quantity of the second allele or (ii) the measured quantity of the first and second alleles for each of the polymorphic loci on the at least one chromosome that is expected to be disomic;
measuring genetic data at a plurality of loci on a chromosome or chromosome segment of interest in the mixed sample;
creating one or more hypotheses specifying the number of copies of the chromosome or chromosome segment of interest in the genome of the fetus;
determining, on a computer, the probability of each of the hypotheses using the measured genetic data for the chromosome or chromosome segment of interest and the ratio of DNA derived from the fetus to DNA derived from the mother; and
selecting the hypothesis with the greatest probability, thereby determining the number of copies of the chromosome or chromosome segment of interest in the genome of the fetus.

24. The method of claim 1, wherein determining the number of copies of the chromosome or chromosome segment of interest in the genome of the fetus is used to determine whether the fetus has three copies of chromosome 21, three copies of chromosome 18, three copies of chromosome 13, two copies of chromosome X and one copy of chromosome Y, or one copy of chromosome X and no copies of chromosome Y.

25. The method of claim 23, wherein the plurality of primers comprises 1000 primers.

26. The method of claim 25, wherein the measuring steps are performed using high throughput sequencing.

* * * * *